US012773442B2

(12) United States Patent
Feng et al.

(10) Patent No.: US 12,773,442 B2
(45) Date of Patent: Oct. 27, 2026

(54) ULTRA-SENSITIVE STEP-FUNCTION OPSIN FOR MINIMALLY INVASIVE OPTOGENETIC STIMULATION

(71) Applicants: THE BROAD INSTITUTE, INC., Cambridge, MA (US); MASSACHUSETTS INSTITUTE OF TECHNOLOGY, Cambridge, MA (US)

(72) Inventors: Guoping Feng, Cambridge, MA (US); Xin Gong, Cambridge, MA (US); Jonathan Ting, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 917 days.

(21) Appl. No.: 17/997,306

(22) PCT Filed: Apr. 28, 2021

(86) PCT No.: PCT/US2021/029666

§ 371 (c)(1),
(2) Date: Oct. 27, 2022

(87) PCT Pub. No.: WO2021/222421

PCT Pub. Date: Nov. 4, 2021

(65) Prior Publication Data

US 2023/0241166 A1 Aug. 3, 2023

Related U.S. Application Data

(60) Provisional application No. 63/017,385, filed on Apr. 29, 2020.

(51) Int. Cl.

| | |
|---|---|
| ***A61K 38/17*** | (2006.01) |
| ***A61N 5/06*** | (2006.01) |
| ***C07K 14/72*** | (2006.01) |
| ***C12N 15/86*** | (2006.01) |

(52) U.S. Cl.

CPC .......... *A61K 38/177* (2013.01); *A61N 5/0622* (2013.01); *C07K 14/723* (2013.01); *C12N 15/86* (2013.01); *C12N 2740/15041* (2013.01); *C12N 2750/14141* (2013.01)

(58) Field of Classification Search

CPC ............................ A61K 38/177; C07K 14/723
See application file for complete search history.

(56) References Cited

U.S. PATENT DOCUMENTS

| | | | |
|---|---|---|---|
| 5,695,934 | A | 12/1997 | Brenner |
| 5,714,330 | A | 2/1998 | Brenner et al. |
| 5,846,946 | A | 12/1998 | Huebner et al. |
| 5,912,148 | A | 6/1999 | Eggerding |
| 5,994,136 | A | 11/1999 | Naldini et al. |
| 6,013,516 | A | 1/2000 | Verma et al. |
| 6,130,073 | A | 10/2000 | Eggerding |
| 6,210,891 | B1 | 4/2001 | Nyren et al. |
| 6,258,568 | B1 | 7/2001 | Nyren |
| 6,432,360 | B1 | 8/2002 | Church |
| 6,485,944 | B1 | 11/2002 | Church et al. |
| 6,511,803 | B1 | 1/2003 | Church et al. |
| 6,787,308 | B2 | 9/2004 | Balasubramanian et al. |
| 6,833,246 | B2 | 12/2004 | Balasubramanian |
| 6,969,488 | B2 | 11/2005 | Bridgham et al. |
| 7,115,400 | B1 | 10/2006 | Adessi et al. |
| 7,259,015 | B2 | 8/2007 | Kingsman et al. |
| 7,303,910 | B2 | 12/2007 | Bebbington et al. |
| 7,351,585 | B2 | 4/2008 | Mitrophanous et al. |
| 8,404,658 | B2 | 3/2013 | Hajjar et al. |
| 8,454,972 | B2 | 6/2013 | Nabel et al. |
| 2004/0013648 | A1 | 1/2004 | Kingsman et al. |
| 2005/0130173 | A1 | 6/2005 | Leamon et al. |
| 2007/0025970 | A1 | 2/2007 | Kingsman et al. |
| 2009/0026082 | A1 | 1/2009 | Rothberg et al. |
| 2009/0111106 | A1 | 4/2009 | Mitrophanous et al. |
| 2009/0127589 | A1 | 5/2009 | Rothberg et al. |
| 2010/0137143 | A1 | 6/2010 | Rothberg et al. |
| 2010/0188073 | A1 | 7/2010 | Rothberg et al. |
| 2010/0197507 | A1 | 8/2010 | Rothberg et al. |
| 2010/0301398 | A1 | 12/2010 | Rothberg et al. |
| 2011/0293571 | A1 | 12/2011 | Widdowson et al. |

(Continued)

FOREIGN PATENT DOCUMENTS

| | | | |
|---|---|---|---|
| WO | 0018957 | A1 | 4/2000 |
| WO | 2005105152 | A2 | 11/2005 |

(Continued)

OTHER PUBLICATIONS

Bergs et al. (2018) Rhodopsin optogenetic toolbox v2.0 for light-sensitive excitation and inhibition in Caenorhabditis elegans. (Year: 2018).*
Punta et al. The Rough Guide to In Silico Function Prediction, or How To Use Sequence and Structure Information To Predict Protein Function. PLoS Comput Biol 4(10): e1000160, 2008 (Year: 2008).*
Whisstock et al. Prediction of protein function from protein sequence and structure. Quarterly Reviews in Biophysics. 36(3):307-340, 2007 (Year: 2007).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*

(Continued)

*Primary Examiner* — Vanessa L. Ford
*Assistant Examiner* — Sandra Carter
(74) *Attorney, Agent, or Firm* — GTC Law Group PC & Affiliates

(57) ABSTRACT

The present disclosure provides compositions and methods for minimally invasive optogenetic stimulation. More particularly, the present disclosure provides compositions and methods for using an ultra-sensitive step-function opsin for minimally invasive optogenetic stimulation.

15 Claims, 50 Drawing Sheets

Specification includes a Sequence Listing.

(56) References Cited

U.S. PATENT DOCUMENTS

2012/0295960 A1 11/2012 Palfi et al.
2020/0332272 A1 10/2020 Zhang et al.

FOREIGN PATENT DOCUMENTS

WO 2006069782 A2 7/2006
WO 2007121947 A1 11/2007
WO WO-2014081449 A1 * 5/2014 ................ A61P 9/12
WO 2015082080 A1 6/2015
WO 2015116658 A1 8/2015
WO 2019/222569 A1 11/2019
WO 2020210655 A1 10/2020
WO 2021222421 A2 11/2021

OTHER PUBLICATIONS

Defeo-Jones et al. Substitution of Lysine for Arginine at Position 42 of Human Transforming Growth Factor-a Eliminates Biological Activity without Changing Internal Disulfide Bonds. Molecular and Cellular Biology, Sep. 1989, p. 4083-4086 (Year: 1989).*

Bork. Powers and Pitfalls in Sequence Analysis: The 70% Hurdle. Genome Research, 2000; 10:398-400 (Year: 2000).*

Bergs et al. ((2018) Rhodopsin optogenetic toolbox v2.0 for light-sensitive excitation and inhibition in Caenorhabditis elegans. PLoS ONE 13(2): e€0191802) (Year: 2018).*

Bergs et al. Rhodopsin optogenetic toolbox v2.0 for light-sensitive excitation and inhibition in Caenorhabitis elegans. Feb. 1, 2018.

Stahlberg et al. Investigating the feasibility of channelrhodopsin variants for nanoscale optogenetics. Jan. 2019.

International Search Report and Written Opinion in corresponding PCT application No. PCT/US2021/029666 dated Oct. 28, 2021.

Acker, Leah et al., "FEF inactivation with improved optogenetic methods", Proc Natl Acad Sci USA v. 113(46), Nov. 2016, pp. E7297-E7306.

Alexander, Georgia M. et al., "Remote control of neuronal activity in transgenic mice expressing evolved G protein-coupled receptors", Neuron, 63(1), Jul. 16, 2009, pp. 27-39.

Anikeeva, Polina et al., "Optetrode: a multichannel readout for optogenetic control in freely moving mice", Nat Neurosci., 15(1), 2012, pp. 163-170.

Aravanis, Alexander M. et al., "An optical neural interface: in vivo control of rodent motor cortex with integrated fiberoptic and optogenetic technology", J. Neural Eng., 4, 2007, pp. S143-S156.

Armbruster, Blaine N. et al., "Evolving the lock to fit the key to create a family of G protein-coupled receptors potently activated by an inert ligand", Proc. Natl. Acad. Sci., vol. 104, No. 12, Mar. 20, 2007, pp. 5163-5168.

Berndt, André et al., "Bi-stable neural state switches", Nature Neuroscience. Vol. 12, No. 2, Feb. 2009, pp. 229-234.

Berndt, André et al., "High-efficiency channel rhodopsins for fast neuronal stimulation at low light levels", Proc. Natl. Acad. Sci., vol. 108, No. 18, May 3, 2011, pp. 7595-7600.

Boyden, Edward S. et al., "Millisecond-timescale, genetically targeted optical control of neural activity", Nature Neuroscience, vol. 8. No. 9,, Sep. 2005, pp. 1263-1268.

Brunetti, Philip M. et al., "Design and Fabrication of Ultralight Weight, Adjustable Multi-electrode Probes for Electrophysiological Recordings in Mice", Journal of Visualized Experiments, 91, e51675, Sep. 2014, 10 pages.

Cavanaugh, James et al., "Optogenetic Inactivation Modifies Monkey Visuomotor Behavior", Neuron, 76(5):, Dec. 6, 2012, pp. 901-907.

Chen, Shuo et al., "Near-infrared deep brain stimulation via upconversion nanoparticle-mediated optogenetics", Science, vol. 359, Feb. 9, 2018, pp. 679-684.

Cheng, Michelle Y. et al., "Optogenetic neuronal stimulation promotes functional recovery after stroke", Proc Natl Acad Sci, vol. 111, No. 35, Sep. 2, 2014, pp. 12913-12918.

Chow, Brian Y. et al., "High-Performance Genetically Targetable Optical Neural Silencing via Light-Driven Proton Pumps", Nature, 463(7277), Jan. 7, 2010, pp. 98-102.

Chuong, Amy S. et al., "Noninvasive optical inhibition with a red-shifted microbial rhodopsin", Nat Neurosci., 17(8), Aug. 2014, pp. 1123-1129.

Dawydow, Alexej et al., "Channelrhodopsin-2-XXL, a powerful optogenetic tool for low-light applications", Proc Natl Acad Sci USA, vol. 111, No. 38, Sep. 23, 2014, pp. 13972-13977.

Diester, Ilka et al., "An optogenetic toolbox designed for primates", Nat Neurosci., 14(3), Mar. 2011, pp. 387-397.

Dziras, Kafui et al., "Persistent Hyperdopaminergia Decreases the Peak Frequency of Hippocampal Theta Oscillations during Quiet Waking and REM Sleep", PLoS ONE 4(4): e5238, Apr. 2009, 8 pages.

Dzirasa, Kafui et al., "How Does Deep Brain Stimulation Work?", Biol. Psychiatry, 72, 2012, pp. 892-894.

El-Shamayleh, Yasmine et al., "Selective optogenetic control of Purkinje cells in monkey cerebellum", Neuron, 95(1), Jul. 5, 2017, 51-62.e4, 29 pages.

Fries, Pascal , "Rhythms For Cognition: Communication Through Coherence", Neuron, 88(1), Oct. 7, 2015, pp. 220-235.

Frostig, Ron D. et al., "Cortical functional architecture and local coupling between neuronal activity and the microcirculation revealed by in vivo high-resolution optical imaging of intrinsic signals", Proc Natl Acad Sci USA, 87(16), Aug. 1990, pp. 6082-6086.

Galvan, Adriana et al., "Advances in Optogenetic and Chemogenetic Methods to Study Brain Circuits in Non-human Primates", J Neural Transm (Vienna), 125(3), Mar. 2018, pp. 547-563.

Gerits, Annelies et al., "Optogenetics in primates: a shining future?", Trends in Genetics, vol. 29, No. 7, Jul. 2013, pp. 403-411.

Gilbert, Frederic et al., "Controlling Brain Cells With Light: Ethical Considerations for Optogenetic Clinical Trials", AJOB Neuroscience, 5(3), 2014, pp. 3-11.

Gradinaru, Viviana et al., "Optical Deconstruction of Parkinsonian Neural Circuitry", Science, 324(5925), Apr. 17, 2009, pp. 354-359.

Han, Xue et al., "Millisecond-Timescale Optical Control of Neural Dynamics in the Nonhuman Primate Brain", Neuron, 62(2), Apr. 30, 2009, pp. 191-198.

Hauss-Wegrzyniak, B. et al., "Chronic Brain Inflammation Results in Cell Loss in the Entorhinal Cortex and Impaired LTP in Perforant Path-Granule Cell Synapses", Experimental Neurology, 176, 2002, pp. 336-341.

Hippenmeyer, Simon et al., "A Developmental Switch in the Response of DRG Neurons to ETS Transcription Factor Signaling", PLoS Biology, vol. 3, Issue 5, e159, May 2005, pp. 0878-0890.

Hira, Riichiro et al., "Transcranial optogenetic stimulation for functional mapping of the motor cortex", Journal of Neuroscience Methods, 179, 2009, pp. 258-263.

Hososhima, Shoko et al., "Kinetic Evaluation of Photosensitivity in Bi-Stable Variants of Chimeric Channelrhodopsins", PLoS ONE, DOI:10.1371/journal.pone.0119558, Mar. 19, 2015, 14 pages.

Iaccarino, Hunter F. et al., "Gamma frequency entrainment attenuates amyloid load and modifies microglia", Nature, 540(7632), Dec. 7, 2016, pp. 230-235.

Jennings, Joshua H. et al., "The Inhibitory Circuit Architecture of the Lateral Hypothalamus Orchestrates Feeding", Science, 341(6153), Sep. 27, 2013, pp. 1517-1521.

Kim, Jin H. et al., "High Cleavage Efficiency of a 2A Peptide Derived from Porcine Teschovirus-1 in Human Cell Lines, Zebrafish and Mice", PLoS ONE 6(4): e18556, Apr. 2011, 8 pages.

Klapoetke, Nathan C. et al., "Independent Optical Excitation of Distinct Neural Populations", Nat Methods, 11(3), Mar. 2014, pp. 338-346.

Kleinlogel, Sonja et al., "Ultra light-sensitive and fast neuronal activation with the Ca++ permeable Channelrhodopsin CatCh", Nature Neuroscience, 14(4), 2011, pp. 513-518.

Kreutzberg, Georg W. , "Microglia: a sensor for pathological events in the CNS", Trends Neurosci, 19, 1996, pp. 312-318.

Liang, Li et al., "Scalable, Lightweight, Integrated and Quick-to-Assemble (SLIQ) Hyperdrives for Functional Circuit Dissection", Frontiers in Neural Circuits, vol. 11, article 8, Feb. 2017, 11 pages.

(56) References Cited

OTHER PUBLICATIONS

Lin, John Y. et al., "Characterization of Engineered Channelrhodopsin Variants with Improved Properties and Kinetics", Biophysical Journal, vol. 96, Mar. 2009, pp. 1803-1814.
Lin, John Y. et al., "ReaChR: A red-shifted variant of channelrhodopsin enables deep transcranial optogenetic excitation", Nat Neurosci., 16(10), Oct. 2013, pp. 1499-1508.
Luo, Xiao-Guang et al., "The changing phenotype of microglia from homeostasis to disease", Translational Neurodegeneration, 1:9, 2012, 13 pages.
Madisen, Linda et al., "A toolbox of Cre-dependent optogenetic transgenic mice for light-induced activation and silencing", Nat Neurosci., 15(5), 2012, pp. 793-802.
Maimon, Benjamin E. et al., "Optogenetic Peripheral Nerve Immunogenicity", Scientific Reports, 8:14076, 2018, 17 pages.
Mattis, Joanna et al., "Principles for applying optogenetic tools derived from direct comparative analysis of microbial opsins", Nat Methods., 9(2), 2012, pp. 159-172.
Nandy, Anirvan et al., "Optogenetically induced low-frequency correlations impair perception", eLife, 8:e35123, 2019, 18 pages.
Nassi, Jonathan J. et al., "Optogenetic activation of normalization in alert macaque visual cortex", Neuron, 86(6), Jun. 17, 2015, pp. 1504-1517.
Nehme, Ralda et al., "Combining NGN2 Programming with Developmental Patterning Generates Human Excitatory Neurons with NMDAR-Mediated Synaptic Transmission", Cell Rep, 23(8), May 22, 2018, pp. 2509-2523.
PCT/US2021/029666, , "International Application Serial No. PCT/US2021/029666, International Preliminary Report on Patentability mailed Nov. 10, 2022", Broad Institute of MIT and Harvard, 9 pages.
Polikov, Vadim S. et al., "Response of brain tissue to chronically implanted neural electrodes", Journal of Neuroscience Methods, 148, 2005, pp. 1-18.
Prakash, Rohit et al., "Two-photon optogenetic toolbox for fast inhibition, excitation and bistable modulation", Nat Methods, 9(12), Dec. 2012, pp. 1171-1179.
Rossi, Jari et al., "Melanocortin-4-receptors Expressed by Cholinergic Neurons Regulate Energy Balance and Glucose Homeostasis", Cell Metab, 13(2), Feb. 2, 2011, pp. 195-204.
Ruiz, Octavio et al., "Optogenetics through windows on the brain in the nonhuman primate", J Neurophysiol, 110, 2013, pp. 1455-1467.
Schaich Borg, Jana et al., "Rat intersubjective decisions are encoded by frequency-specific oscillatory contexts", Brain and Behavior, 7:e00710, 2017, 25 pages.
Schiessl, Ingo et al., "Optical imaging of the retinotopic organization of V1 in the common marmoset", NeuroImage, 20, 2003, pp. 1857-1864.
Schindelin, Johannes et al., "Fiji—an Open Source platform for biological image analysis", Nat Methods, 9(7), Jun. 28, 2012, 15 pages.
Selimbeyoglu, Aslihan et al., "Modulation of prefrontal cortex excitation/inhibition balance rescues social behavior in CNTNAP2-deficient mice", Sci. Transl. Med. 9, eaah6733, Aug. 2, 2017, 10 pages.
Sorokin, Jordan M. , "Bidirectional control of generalized epilepsy networks via rapid real-time switching of firing mode", Neuron, 93(1), Jan. 4, 2017, pp. 194-210.
Szarowski, D. H. et al., "Brain responses to micro-machined silicon devices", Brain Research, 983, 2003, pp. 23-35.
Tanaka, Kenji F. et al., "Expanding the Repertoire of Optogenetically Targeted Cells with an Enhanced Gene Expression System", Cell Reports, 2, Aug. 30, 2012, pp. 397-406.
Thyagarajan, Senthil et al., "Visual Function in Mice with Photoreceptor Degeneration and Transgenic Expression of Channelrhodopsin 2 in Ganglion Cells", The Journal of Neuroscience, 30(26), Jun. 30, 2010, pp. 8745-8758.
Ullrich, Sybille et al., "Degradation of channelopsin-2 in the absence of retinal and degradation resistance in certain mutants", Biol. Chem., 394(2), 2013, pp. 271-280.
Weaver, Frances M. et al., "Randomized trial of deep brain stimulation for Parkinson disease—Thirty-six-month outcomes", Neurology, 79, 2012, pp. 55-65.
Williams, Justin C. et al., "From Optogenetic Technologies to Neuromodulation Therapies", Science Translational Medicine, vol. 5 Issue 177, 177ps6, Mar. 20, 2013, 5 pages.
Xu, Hua-Tai et al., "Choice of cranial window type for in vivo imaging affects dendritic spine turnover in the cortex", Nature Neuroscience, vol. 10, No. 5, May 2007, pp. 549-551.
Yizhar, Ofer et al., "Neocortical excitation/inhibition balance in information processing and social dysfunction", Nature, 477(7363), Jul. 27, 2011, pp. 171-178.
Yizhar, Ofer et al., "Optogenetics in Neural Systems", Neuron, 71, Jul. 14, 2011, pp. 9-34.
Zhao, Shengli et al., "Cell-type Specific Optogenetic Mice for Dissecting Neural Circuitry Function", Nat Methods, 8(9), Sep. 2011, pp. 745-752.
Zhao, Yan-Jie et al., "Skull optical clearing window for in vivo imaging of the mouse cortex at synaptic resolution", Light: Science & Applications, 7, 17153, 2018, 9 pages.

* cited by examiner

SEQUENCE LISTING

```
<160> NUMBER OF SEQ ID NOS: 8

<210> SEQ ID NO 1
<211> LENGTH: 939
<212> TYPE: DNA
<213> ORGANISM: Artificial
<220> FEATURE:
<223> OTHER INFORMATION: synthetic

<400> SEQUENCE: 1

atggactatg gcggcgcttt gtctgccgtc ggacgcgaac ttttgttcgt tactaatcct      60

gtggtggtga acgggtccgt cctggtccct gaggatcaat gttactgtgc cggatggatt     120

gaatctcgcg gcacgaacgg cgctcagacc gcgtcaaatg tcctgcagtg gcttgcagca     180

ggattcagca ttttgctgct gatgttctat gcctaccaaa cctggaaatc tacatgcggc     240

tgggaggaga tctatgtgtg cgccattgaa atggttaagg tgattctcga gttctttttt     300

gagtttaaga atccctctat gctctacctt gccacaggac accgggtgca gtggctgcgc     360

tatgcagagt ggctgctcac ttctcctgtc atccttatcc acctgagcaa cctcaccggc     420

ctgagcaacg actacagcag gagaaccatg ggactccttg tctcagccat cgggactatc     480

gtgtgggggg ctaccagcgc catggcaacc ggctatgtta aagtcatctt cttttgtctt     540

ggattgtgct atggcgcgaa cacatttttt cacgccgcca aagcatatat cgagggttat     600

catactgtgc caaagggtcg gtgccgccag gtcgtgaccg gcatggcatg gctgtttttc     660

gtgagctggg gtatgttccc aattctcttc attttggggc ccgaaggttt tggcgtcctg     720

agcgtctatg gctccaccgt aggtcacacg attattgatc tgatgagtaa aaattgttgg     780

gggttgttgg gacactacct gcgcgtcctg atccacgagc acatattgat tcacggagat     840

atccgcaaaa ccaccaaact gaacatcggc ggaacggaga tcgaggtcga gactctcgtc     900

gaagacgaag ccgaggccgg agccgtgcca gttaactaa                            939


<210> SEQ ID NO 2
<211> LENGTH: 939
<212> TYPE: DNA
<213> ORGANISM: Artificial
<220> FEATURE:
<223> OTHER INFORMATION: synthetic

<400> SEQUENCE: 2

atggactatg gcggcgcttt gtctgccgtc ggacgcgaac ttttgttcgt tactaatcct      60

gtggtggtga acgggtccgt cctggtccct gaggatcaat gttactgtgc cggatggatt     120

gaatctcgcg gcacgaacgg cgctcagacc gcgtcaaatg tcctgcagtg gcttgcagca     180

ggattcagca ttttgctgct gatgttctat gcctaccaaa cctggaaatc tacatgcggc     240

tgggaggaga tctatgtgtg cgccattgaa atggttaagg tgattctcga gttctttttt     300

gagtttaaga atccctctat gctctacctt gccacaggac accgggtgca gtggctgcgc     360

tatgcagagt ggctgctcac ttctcctgtc atccttatcc acctgagcaa cctcaccggc     420
```

```
ctgagcaacg actacagcag gagaaccatg ggactccttg tctcagccat cgggtgtatc    480

gtgtgggggg ctaccagcgc catggcaacc ggctatgtta aagtcatctt cttttgtctt    540

ggattgtgct atggcgcgaa cacatttttt cacgccgcca aagcatatat cgagggttat    600

catactgtgc caaagggtcg gtgccgccag gtcgtgaccg gcatggcatg gctgtttttc    660

gtgagctggg gtatgttccc aattctcttc attttggggc ccgaaggttt tggcgtcctg    720

agcgtctatg gctccaccgt aggtcacacg attattgatc tgatgagtaa aaattgttgg    780

gggttgttgg gacactacct gcgcgtcctg atccacgagc acatattgat tcacggagat    840

atccgcaaaa ccaccaaact gaacatcggc ggaacggaga tcgaggtcga gactctcgtc    900

gaagacgaag ccgaggccgg agccgtgcca gttaactaa                           939
```

<210> SEQ ID NO 3
<211> LENGTH: 6739
<212> TYPE: DNA
<213> ORGANISM: Artificial
<220> FEATURE:
<223> OTHER INFORMATION: synthetic

<400> SEQUENCE: 3

```
cccccctatc tcgcgcctcg cgtggtgcgg tccggctggg ccggcggcgg cgcggacgcg     60

accaaggtgg ccgggaaggg gagtttgcgg gggaccggcg agtgacgtca gcgcgccttc    120

agtgctgagg cggcggtggc gcgcgccgcc aggcgggggc gaaggcactg tccgcggtgc    180

tgaagctggc agtgcgcacg cgcctcgccg catcctgttt cccctccccc tctctgatag    240

gggatgcgca atttggggaa tgggggttgg gtgcttgtcc agtgggtcgg ggtcggtcgt    300

caggtaggca cccccacccc gcctcatcct ggtcctaaaa cccacttgca ctcatacgca    360

gggccctctg cagtctagac acttaattaa acgcgtgcgg ccgcaggaac ccctagtgat    420

ggagttggcc actccctctc tgcgcgctcg ctcgctcact gaggccgggc gaccaaaggt    480

cgcccgacgc ccgggcggcc tcagtgagcg agcgagcgcg cagctgcctg caggacatgt    540

gagcaaaagg ccagcaaaag gccaggaacc gtaaaaaggc cgcgttgctg gcgtttttcc    600

ataggctccg cccccctgac gagcatcaca aaaatcgacg ctcaagtcag aggtggcgaa    660

acccgacagg actataaaga taccaggcgt ttccccctgg aagctccctc gtgcgctctc    720

ctgttccgac cctgccgctt accggatacc tgtccgcctt tctcccttcg ggaagcgtgg    780

cgctttctca tagctcacgc tgtaggtatc tcagttcggt gtaggtcgtt cgctccaagc    840

tgggctgtgt gcacgaaccc cccgttcagc ccgaccgctg cgccttatcc ggtaactatc    900

gtcttgagtc caacccggta agacacgact tatcgccact ggcagcagcc actggtaaca    960

ggattagcag agcgaggtat gtaggcggtg ctacagagtt cttgaagtgg tggcctaact   1020

acggctacac tagaagaaca gtatttggta tctgcgctct gctgaagcca gttaccttcg   1080

gaaaaagagt tggtagctct tgatccggca aacaaaccac cgctggtagc ggtggttttt   1140

ttgtttgcaa gcagcagatt acgcgcagaa aaaaaggatc tcaagaagat cctttgatct   1200

tttctacggg gtctgacgct cagtggaacg aaaactcacg ttaagggatt ttggtcatga   1260

gattatcaaa aaggatcttc acctagatcc ttttaaatta aaaatgaagt tttaaatcaa   1320

tctaaagtat atatgagtaa acttggtctg acagttacca atgcttaatc agtgaggcac   1380

ctatctcagc gatctgtcta tttcgttcat ccatagttgc ctgactcccc gtcgtgtaga   1440

taactacgat acgggagggc ttaccatctg gccccagtgc tgcaatgata ccgcgagacc   1500

cacgctcacc ggctccagat ttatcagcaa taaaccagcc agccggaagg gccgagcgca   1560
```

```
gaagtggtcc tgcaacttta tccgcctcca tccagtctat taattgttgc cgggaagcta   1620
gagtaagtag ttcgccagtt aatagtttgc gcaacgttgt tgccattgct acaggcatcg   1680
tggtgtcacg ctcgtcgttt ggtatggctt cattcagctc cggttcccaa cgatcaaggc   1740
gagttacatg atcccccatg ttgtgcaaaa aagcggttag ctccttcggt cctccgatcg   1800
ttgtcagaag taagttggcc gcagtgttat cactcatggt tatggcagca ctgcataatt   1860
ctcttactgt catgccatcc gtaagatgct tttctgtgac tggtgagtac tcaaccaagt   1920
cattctgaga atagtgtatg cggcgaccga gttgctcttg cccggcgtca atacgggata   1980
ataccgcgcc acatagcaga actttaaaag tgctcatcat tggaaaacgt tcttcggggc   2040
gaaaactctc aaggatctta ccgctgttga gatccagttc gatgtaaccc actcgtgcac   2100
ccaactgatc ttcagcatct tttactttca ccagcgtttc tgggtgagca aaaacaggaa   2160
ggcaaaatgc cgcaaaaaag ggaataaggg cgacacggaa atgttgaata ctcatactct   2220
tcctttttca atattattga agcatttatc agggttattg tctcatgagc ggatacatat   2280
ttgaatgtat ttagaaaaat aaacaaatag gggttccgcg cacatttccc cgaaaagtgc   2340
cacctgacgt ctaagaaacc attattatca tgacattaac ctataaaaat aggcgtatca   2400
cgaggccctt tcgtctcgcg cgtttcggtg atgacggtga aaacctctga cacatgcagc   2460
tcccggagac ggtcacagct tgtctgtaag cggatgccgg gagcagacaa gcccgtcagg   2520
gcgcgtcagc gggtgttggc gggtgtcggg gctggcttaa ctatgcggca tcagagcaga   2580
ttgtactgag agtgcaccat aaaattgtaa acgttaatat tttgttaaaa ttcgcgttaa   2640
atttttgtta aatcagctca ttttttaacc aatagaccga aatcggcaaa atcccttata   2700
aatcaaaaga atagcccgag atagagttga gtgttgttcc agtttggaac aagagtccac   2760
tattaaagaa cgtggactcc aacgtcaaag ggcgaaaaac cgtctatcag ggcgatggcc   2820
cactacgtga accatcaccc aaatcaagtt ttttggggtc gaggtgccgt aaagcactaa   2880
atcggaaccc taaagggagc ccccgattta gagcttgacg gggaaagccg gcgaacgtgg   2940
cgagaaagga agggaagaaa gcgaaaggag cgggcgctaa ggcgctggca agtgtagcgg   3000
tcacgctgcg cgtaaccacc acacccgccg cgcttaatgc gccgctacag ggcgcgtact   3060
atggttgctt tgacgtatgc ggtgtgaaat accgcacaga tgcgtaagga gaaaataccg   3120
catcaggcgc ccctgcaggc agctgcgcgc tcgctcgctc actgaggccg cccgggcaaa   3180
gcccgggcgt cgggcgacct ttggtcgccc ggcctcagtg agcgagcgag cgcgcagaga   3240
gggagtggcc aactccatca ctaggggttc ctgcggccgc tcggtccgca cgtggttacc   3300
tacaaaatca gaaggacagg gaagggagca gtggttcacg cctgtaatcc cagcaatttg   3360
ggaggccaag gtgggtagat cacctgagat taggagttgg agaccagcct ggccaatatg   3420
gtgaaacccc gtctctacca aaaaaacaaa aattagctga gcctggtcat gcatgcctgg   3480
aatcccaaca actcgggagg ctgaggcagg agaatcgctt gaacccagga ggcggagatt   3540
gcagtgagcc aagattgtgc cactgcactc cagcttggtt cccaatagac cccgcaggcc   3600
ctacaggttg tcttcccaac ttgccccttg ctccatacca ccccccctcca ccccataata   3660
ttatagaagg acacctagtc agacaaaatg atgcaactta attttattag gacaaggctg   3720
gtgggcactg gagtggcaac ttccagggcc aggagaggca ctggggaggg gtcacaggga   3780
tgccacccgt agatctctcg agcagcgctc ggtatcgatg cggggaggcg gcccaaaggg   3840
agatccgact cgtctgaggg cgaaggcgaa gacgcggaag aggccgcaga gccggcagca   3900
```

ggccgcggga aggaaggtcc gctggattga gggccgaagg gacgtagcag aaggacgtcc 3960
cgcgcagaat ccaggtggca acataggcga gcagccaagg aaaggacgat gatttccccg 4020
acaacaccac ggaattgtca gtgcccaaca gccgagcccc tgtccagcag cgggcaaggc 4080
aggcggcgat gagttccgcc gtggcaatag ggagggggaa agcgaaagtc ccggaaagga 4140
gctgacaggt ggtggcaatg ccccaaccag tgggggttgc gtcagcaaac acagtgcaca 4200
ccacgccacg ttgcctgaca acgggccaca actcctcata aagagacagc aaccaggatt 4260
tatacaagga ggagaaaatg aaagccatac gggaagcaat agcatgatac aaaggcatta 4320
aagcagcgta tccacatagc gtaaaaggag caacatagtt aagaatacca gtcaatcttt 4380
cacaaatttt gtaatccaga ggttgattat cgataagctt gatatcgaat tccctgcagg 4440
ggcgcgccgt cgacttactt gtacagctcg tccatgccgt acaggaacag gtggtggcgg 4500
ccctcggagc gctcgtactg ttccacgatg gtgtagtcct cgttgtggga ggtgatgtcc 4560
agcttggtgt ccacgtagta gtagccgggc agttgcacgg gcttcttggc catgtagatg 4620
gtcttgaact ccaccaggta gtggccgccg tccttcagct tcagggcctg gtggatctcg 4680
cccttcagca cgccgtcgcg gggtacagg cgctcggtgg aggcctccca gcccatggtc 4740
ttcttctgca ttacggggcc gtcggggggg aagttggtgc cgcgcatctt caccttgtag 4800
atcagcgtgc cgtcctgcag ggaggagtcc tgggtcacgg tcaccagacc gccgtcctcg 4860
aagttcatca cgcgctccca cttgaagccc tcggggaagg acagcttctt gtaatcgggg 4920
atgtcggcgg ggtgcttcac gtacgccttg gagccgtaca tgaactgggg ggacaggatg 4980
tcccaggcga agggcagggg gccgcccttg gtcaccttca gcttggcggt ctgggtgccc 5040
tcgtaggggc ggccctcgcc ctcgccctcg atctcgaact cgtggccgtt catggagccc 5100
tccatgcgca ccttgaagcg catgaactct ttgatgacct cctcgccctt gctcaccacc 5160
ttcctcttct tcttgggggc cattctagat ggcccgggat tctcttcgac atcccctgct 5220
tgtttcaaca gggagaagtt agtggctccg cttccgttat ccttcgctgt catcatttgt 5280
acaaactctt cgtagtttac ctgaccatcc ccatcgatgt ctgcttccct gatcatttca 5340
tcaacctctt catctgttaa cttctctcca aggtttgtca tcacgtggcg aagctctgct 5400
gcactgatgt agccattgcc atccttatca aacacaccga acgcttctct aatttcttct 5460
tccgtgtccc tgtatttcat ttttcttgcc atcattgtca ggaactcagg gaagtcgatt 5520
gtgccgtcac cgtcggcatc tacttcattg atcatgtcct gcagctctgc ttctgtgggg 5580
ttctgcccca gagaccgcat caccgtcccc agctccttgg ttgttattgt cccatccccg 5640
tccttgtcaa atagggagaa agcctcttta aattctgcga tctgctcttc agtcagttgg 5700
tccggcaggt tgtactccag cttgtgcccc aggatgttgc cgtcctcctt gaagtcgatg 5760
cccttcagct cgatgcggtt caccagggtg tcgccctcga acttcacctc ggcgcgggtc 5820
ttgtagttgc cgtcgtcctt gaagaagatg gtgcgctcct ggatgtagcc ttcgggcatg 5880
gcggacttga agaagtcgtg ctgcttcatg tggtcggggt agcggctgaa gcactgcacg 5940
ccgtaggtca gggtggtcac gagggtgggc cagggcacgg gcagcttgcc ggtggtgcag 6000
atgaacttca gggtcagctt gccgtaggtg gcatcgccct caccctcgcc ggacacgctg 6060
aacttgtggc cgtttacgtc gccgtccagc tcgaccagga tgggcaccac cccggtgaac 6120
agctcctcgc ccttgctcac catgctccct ccggtaccgc ccttgtacag ctcgtccatg 6180
ccgagagtga tcccggcggc ggtcacgaac tccagcagga ccatgtgatc gcgcttctcg 6240
ttggggtctt tcgaaagttt ggactgcacg ctcaggtagt ggttgtcggg cagcagcacg 6300
gggccgtcgc cgatgggggt gttctgctgg tagtggtagg cgagctgcac gccgccgtcc 6360
tcgatgttgt ggcggatgtg gaagttcgcc ttgatgccgt tcttctgctt gtcggccttg 6420
atatagacgt tctcgagtga gctcagccga cctatagctc tgactgcgtg acctgtctta 6480
ttccacttac gacgtgatga gtcgaccatg gtggcgagat ccttatcgtc atcgtcgtac 6540
agatcccgac ccatttgctg tccaccagtc atgctagcca taccatgatg atgatgatga 6600
tgagaaccca tggtggcgcc ggatcctcta gccggtttct cgactgcgct ctcaggcacg 6660
acacgactcc tccgctgccc accgcagact gaggcagcgc tgagtcgccg gcgccgcagc 6720
gcagatggtc gcgcccgtg 6739

<210> SEQ ID NO 4
<211> LENGTH: 20
<212> TYPE: DNA
<213> ORGANISM: Artificial
<220> FEATURE:
<223> OTHER INFORMATION: synthetic

<400> SEQUENCE: 4
ttggtgcgtt tgcggggatg 20

<210> SEQ ID NO 5
<211> LENGTH: 20
<212> TYPE: DNA
<213> ORGANISM: Artificial
<220> FEATURE:
<223> OTHER INFORMATION: synthetic

<400> SEQUENCE: 5
gttatgtaac gcggaactcc 20

<210> SEQ ID NO 6
<211> LENGTH: 20
<212> TYPE: DNA
<213> ORGANISM: Artificial
<220> FEATURE:
<223> OTHER INFORMATION: synthetic

<400> SEQUENCE: 6
cacttgctct cccaaagtcg 20

<210> SEQ ID NO 7
<211> LENGTH: 20
<212> TYPE: DNA
<213> ORGANISM: Artificial
<220> FEATURE:
<223> OTHER INFORMATION: synthetic

<400> SEQUENCE: 7
tagtctaact cgcgacactg 20

<210> SEQ ID NO 8
<211> LENGTH: 20
<212> TYPE: DNA
<213> ORGANISM: Artificial
<220> FEATURE:
<223> OTHER INFORMATION: synthetic

<400> SEQUENCE: 8
gttatgtaac gcggaactcc 20

ULTRA-SENSITIVE STEP-FUNCTION OPSIN FOR MINIMALLY INVASIVE OPTOGENETIC STIMULATION

CROSS REFERENCE TO RELATED APPLICATIONS

This application is a national stage application, filed under 35 U.S.C. § 371, of International Application No. PCT/US2021/029666, filed Apr. 28, 2021, which claims priority to U.S. Provisional Application No. 63/017,385, filed Apr. 29, 2020, and entitled "Ultra-Sensitive Step-Function Opsin for Minimally Invasive Optogenetic Stimulation." The entire contents of the aforementioned application are incorporated herein by reference.

STATEMENT AS TO FEDERALLY SPONSORED RESEARCH

This invention was made with government support under Grant No. R01NS 113245 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Jun. 25, 2021, is named BN00007_1161_SeqList_ST25.txt and is 13 KB in size.

FIELD OF THE DISCLOSURE

The present disclosure relates to compositions and methods for minimally invasive optogenetic stimulation. More particularly, the present disclosure relates to compositions and methods for using an ultra-sensitive step-function opsin for minimally invasive optogenetic stimulation.

BACKGROUND OF THE DISCLOSURE

While advancements in optogenetics have made it an increasingly popular option for the treatment of neurological diseases through modulation of neuronal activity, such methods are disadvantageous because they tend to rely upon surgical implants, which cause permanent damage to neurons, glia, and capillaries. Furthermore, surgical implantation increases susceptibility to infection, which poses a significant health risk. Additionally, a major challenge in current applications of optogenetics is the lack of anatomical coverage of optogenetic stimulation because of the severe attenuation of light in the surrounding tissues. This attenuation makes it difficult to target internal regions of the brain (e.g., deep brain tissue). Therefore, a need exists for optogenetic compositions and methods that are minimally invasive without damage to surrounding tissues, and that are able to provide optogenetic stimulation over a wide spatial range of tissue types (e.g., deep brain tissue).

BRIEF SUMMARY OF THE DISCLOSURE

The current disclosure relates, at least in part, to the discovery of compositions and methods capable of modulating activities of living mammalian cells across a time course, via inducible vectors to incorporate living cells with target genetic materials. The target genetic material is then activated externally to modulate the activities of the living mammalian cells. In particular, the instant disclosure has identified compositions and methods through which a vector can be used to incorporate target genetic material into mammalian brain cells, which may then be optically activated (e.g., internally or externally) to modulate their activity. Advantageously, the techniques herein provide optogenetic compositions and methods that allow non-invasive optogenetic stimulation (e.g., transdural or transcranial) without the need for surgical implantation of fiber optic cables. A further advantage of the techniques herein is that they provide optogenetic stimulation of cells over a distance (e.g., stimulation of deep brain tissues).

In aspects, the disclosure provides a composition comprising a step-function opsin (SFO) polypeptide that includes at least two stabilized step function mutations and at least one peak amplitude increasing mutation.

In embodiments, the at least two stabilized step function mutations are C128S and/or D156A.

In embodiments, the at least one stabilized step function mutations is T159C.

In embodiment, the SFO polypeptide may be a triple mutant that includes the mutations C128S, D156A, and T159C.

In embodiments, the SFO polypeptide has an amino acid sequence having at least 95%, 96%, 97%, 98%, 99%, or 100% amino acid identity to SEQ ID NO:1 or SEQ ID NO: 2 or SEQ ID NO:3.

In embodiments, the SFO polypeptide induces a peak photocurrent amplitude between about 250 pA and about 450 pA.

In embodiments, the SFO polypeptide induces a peak photocurrent amplitude of about 320 pA, about 330 pA, about 340 pA, about 350 pA, about 360, about 370 pA, or about 380 pA.

In embodiments, the SFO polypeptide maintains a prolonged open state of between about 25 minutes and about 45 minutes, optionally the SFO polypeptide maintains a prolonged open state of about 25, about 30, about 35, about 40, or about 45 minutes.

In aspects, the disclosure provides an isolated nucleic acid comprising a nucleotide sequence that encodes a step-function opsin (SFO) polypeptide including at least two stabilized step function mutations and at least one peak amplitude increasing mutation.

In embodiments, the SFO polypeptide further includes a signal peptide.

In embodiments, the nucleic acid has the nucleotide sequence set forth in SEQ ID NO:6 or SEQ ID NO:8.

In aspects, the disclosure provides a recombinant expression vector comprising the above nucleic acid.

In embodiments, the isolated nucleic acid is operatively linked to a promoter specific for a cell type.

In embodiments, the cell type is selected from the group consisting of an embryonic stem cell, a sensory neuron, a motor neuron, an interneuron, an oligodendrocyte, and an astrocyte.

In embodiments, the promoter is selected from the group consisting of CAG, CMV immediate early, hSyn promoter, HSV thymidine kinase, early and late SV40, CamKII, LTRs from retrovirus, and mouse metallothionein I.

In embodiments, the expression vector is a viral expression vector, optionally an adeno-associated vector or a lentivirus vector.

In embodiments, the recombinant expression vector has a nucleotide sequence at least 95%, 96%, 97%, 98%, 99%, or 100% identical to the nucleotide sequence set forth in SEQ ID NO:6 or SEQ ID NO:8.

In aspects, the disclosure provides a method for modulating activity of a neuronal cell that includes exposing the neuronal cell to one or more wavelengths of light, wherein the neuronal cell expresses a step-function opsin (SFO) polypeptide including at least two stabilized step function mutations and at least one peak amplitude increasing mutation, and an activity of the neuronal cell is modulated in response to the one or more wavelengths of light.

In embodiments, the modulated activity is reversible, optionally the modulated activity is polarizing or depolarizing the neuronal cell.

In embodiments, a first wavelength of light polarizes the neuronal cell and a second wavelength of light depolarizes the cell.

In embodiments, the SFO polypeptide includes the mutations C128S, D156A, and T159C.

In embodiments, the neuronal cell is genetically modified to include a nucleic acid that encodes the SFO polypeptide.

In embodiments, the nucleic acid is present in a recombinant expression vector, optionally an adeno-associated viral vector or a lentivirus vector.

In embodiments, the neuronal cell is located in a region of the brain selected from the group consisting of an occipital lobe, a temporal lobe, a parietal lobe, a frontal lobe, a cerebral cortex, a cerebellum, a hypothalamus, a thalamus, a pituitary gland, a pineal gland, an amygdala, a hippocampus, and a mid-brain.

In embodiments, the one or more wavelengths are delivered by a fiber optic cable.

In embodiments, the one or more wavelengths are delivered transcranially to an internal region of the brain.

In embodiments, the internal region of the brain is between about 5 mm and about 7 mm below a skull surface.

In embodiments, the one or more wavelengths are not delivered by a fiber optic cable.

In embodiments, the modulating is used to treat a neurological disorder in a patient.

In embodiments, the neurological disorder is a psychiatric disorder.

In aspects, the disclosure provides a method for increasing activity of a Parafascicular (PF) thalamus-to-nucleus accumbens (NAc) neuronal cell in a subject, the method comprising exposing the PF-to-NAc neuronal cell to one or more wavelengths of light, wherein the PF-to-NAc neuronal cell expresses a step-function opsin (SFO) polypeptide including at least two stabilized step function mutations and at least one peak amplitude increasing mutation, and an activity of the PF-to-NAc neuronal cell is increased in response to the one or more wavelengths of light.

In embodiments, the subject has Parkinson's Disease (PD).

In embodiments, said increasing activity of the PF-to-NAc neuronal cell in the subject treats a non-motor behavioral deficit in the subject. In related embodiments, the non-motor behavioral deficit in the subject is despair or depression.

In embodiments, the increased activity is reversible, optionally the increased activity is polarizing or depolarizing the PF-to-NAc neuronal cell.

In embodiments, a first wavelength of light polarizes the PF-to-NAc neuronal cell and a second wavelength of light depolarizes the cell.

In embodiments, the SFO polypeptide includes the mutations C128S, D156A, and T159C.

In embodiments, the PF-to-NAc neuronal cell is genetically modified to include a nucleic acid that encodes the SFO polypeptide.

In embodiments, the nucleic acid is present in a recombinant expression vector, optionally an adeno-associated viral vector or a lentivirus vector.

In embodiments, the one or more wavelengths are delivered by a fiber optic cable.

In embodiments, the one or more wavelengths are delivered transcranially to an internal region of the brain.

In embodiments, the internal region of the brain is between about 5 mm and about 7 mm below a skull surface.

In embodiments, the one or more wavelengths are not delivered by a fiber optic cable.

Definitions

The term "fusion protein" as used herein refers to an engineered polypeptide that combines sequence elements excerpted from two or more other proteins, optionally from two or more naturally-occurring proteins.

The terms "transfect," "transfects," "transfecting" and "transfection" as used herein refer to the delivery of nucleic acids (usually DNA or RNA) to the cytoplasm or nucleus of cells, e.g., through the use of cationic lipid vehicle(s) and/or by means of electroporation, or other art-recognized means of transfection.

The term "transduction," as used herein refers to the delivery of nucleic acids (usually DNA or RNA) to the cytoplasm or nucleus of cells through the use of viral delivery, e.g., via lentiviral delivery vectors/plasmids, or other art-recognized means of transduction.

The term "plasmid" as used herein refers to a construction comprised of genetic material designed to direct transformation of a targeted cell. The plasmid consist of a plasmid backbone. A "plasmid backbone" as used herein contains multiple genetic elements positional and sequentially oriented with other necessary genetic elements such that the nucleic acid in a nucleic acid cassette can be transcribed and when necessary translated in the transfected or transduced cells. The term plasmid as used herein can refer to nucleic acid, e.g., DNA derived from a plasmid vector, cosmid, phagemid or bacteriophage, into which one or more fragments of nucleic acid may be inserted or cloned which encode for particular genes A "viral vector" as used herein is one that is physically incorporated in a viral particle by the inclusion of a portion of a viral genome within the vector, e.g., a packaging signal, and is not merely DNA or a located gene taken from a portion of a viral nucleic acid. Thus, while a portion of a viral genome can be present in a plasmid of the present disclosure, that portion does not cause incorporation of the plasmid into a viral particle and thus is unable to produce an infective viral particle.

As used herein, the term "vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

As used herein, the term "integrating vector" refers to a vector whose integration or insertion into a nucleic acid (e.g., a chromosome) is accomplished via an integrase.

Examples of "integrating vectors" include, but are not limited to, retroviral vectors, transposons, and adeno associated virus vectors.

As used herein, the term "integrated" refers to a vector that is stably inserted into the genome (i.e., into a chromosome) of a host cell.

As used herein, the term "genome" refers to the genetic material (e.g., chromosomes) of an organism.

As used herein, the term "exogenous gene" refers to a gene that is not naturally present in a host organism or cell, or is artificially introduced into a host organism or cell.

The term "gene" refers to a nucleic acid (e.g., DNA or RNA) sequence that comprises coding sequences necessary for the production of a precursor or polypeptide (e.g., SOUL). The polypeptide can be encoded by a full length coding sequence or by any portion of the coding sequence so long as the desired activity or functional properties (e.g., light sensitivity, neuronal modulation, etc.) of the full-length or fragment are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein, the terms "nucleic acid molecule encoding," "DNA sequence encoding," "DNA encoding," "RNA sequence encoding," and "RNA encoding" refer to the order or sequence of deoxyribonucleotides or ribonucleotides along a strand of deoxyribonucleic acid or ribonucleic acid. The order of these deoxyribonucleotides or ribonucleotides determines the order of amino acids along the polypeptide (protein) chain. The DNA or RNA sequence thus codes for the amino acid sequence.

As used herein, the term "variant," when used in reference to a protein, refers to proteins encoded by partially homologous nucleic acids so that the amino acid sequence of the proteins varies. As used herein, the term "variant" encompasses proteins encoded by homologous genes having both conservative and nonconservative amino acid substitutions that do not result in a change in protein function, as well as proteins encoded by homologous genes having amino acid substitutions that cause decreased (e.g., null mutations) protein function or increased protein function.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "regulatory element" refers to a genetic element which controls some aspect of the expression of nucleic acid sequences. For example, a promoter is a regulatory element that facilitates the initiation of transcription of an operably linked coding region. Other regulatory elements are splicing signals, polyadenylation signals, termination signals, RNA export elements, internal ribosome entry sites, etc.

Transcriptional control signals in eukaryotes comprise "promoter" and "enhancer" elements. Promoters and enhancers consist of short arrays of DNA sequences that interact specifically with cellular proteins involved in transcription (Maniatis et al., (1987) Science 236:1237). Promoter and enhancer elements have been isolated from a variety of eukaryotic sources including genes in yeast, insect and mammalian cells, and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see, Voss et al., (1986) Trends Biochem. Sci., 11:287; and Maniatis et al., supra). For example, the SV40 early gene enhancer is very active in a wide variety of cell types from many mammalian species and has been widely used for the expression of proteins in mammalian cells (Dijkema et al, (1985) EMBO J. 4:761). Two other examples of promoter/enhancer elements active in a broad range of mammalian cell types are those from the human elongation factor 1α gene (Uetsuki et al., (1989) J. Biol. Chem., 264:5791; Kim et al., (1990) Gene 91:217; and Mizushima and Nagata, (1990) Nuc. Acids. Res., 18:5322) and the long terminal repeats of the Rous sarcoma virus (Gorman et al., (1982) Proc. Natl. Acad. Sci. USA 79:6777) and the human cytomegalovirus (Boshart et al., (1985) Cell 41:521).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques such as cloning and recombination) such that transcription of that gene is directed by the linked enhancer/promoter.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, etc.). In contrast, a "regulatable" promoter is one which is capable of directing a level of transcription of an operably linked nucleic acid sequence in the presence of a stimulus (e.g., heat shock, chemicals, etc.) which is different from the level of transcription of the operably linked nucleic acid sequence in the absence of the stimulus. Certain promoters are also known in the art to impart tissue-specificity and/or temporal/developmental specificity to expression of a nucleic acid sequence under control of such a promoter.

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high "copy number" (up to 104 copies/cell) in cells that express the appropriate viral T antigen. Vectors that contain the replicons from bovine papillomavirus or Epstein-Barr virus replicate extrachromosomally at "low copy number" (~100 copies/cell). However, it is not intended that expression vectors be limited to any particular viral origin of replication.

As used herein, the term "retrovirus" refers to a retroviral particle which is capable of entering a cell (i.e., the particle contains a membrane-associated protein such as an envelope protein or a viral G glycoprotein which can bind to the host cell surface and facilitate entry of the viral particle into the cytoplasm of the host cell) and integrating the retroviral genome (as a double-stranded provirus) into the genome of the host cell. The term "retrovirus" encompasses Oncovirinae (e.g., Moloney murine leukemia virus (Mo-LV, also recited as simply "MLV" herein), Moloney murine sarcoma virus (MoMSV), and Mouse mammary tumor virus (MMTV), Spumavirinae, and Lentivirinae (e.g., Human immunodeficiency virus, Simian immunodeficiency virus, Equine infection anemia virus, and Caprine arthritis-encephalitis virus; See, e.g., U.S. Pat. Nos. 5,994,136 and 6,013,516, both of which are incorporated herein by reference).

As used herein, the term "retroviral vector" refers to a retrovirus that has been modified to express a gene of interest. Retroviral vectors can be used to transfer genes efficiently into host cells by exploiting the viral infectious process. Foreign or heterologous genes cloned (i.e., inserted using molecular biological techniques) into the retroviral genome can be delivered efficiently to host cells which are susceptible to infection by the retrovirus.

As used herein, the term "lentivirus vector" refers to retroviral vectors derived from the Lentiviridae family (e.g., human immunodeficiency virus, simian immunodeficiency virus, equine infectious anemia virus, and caprine arthritis-encephalitis virus) that are capable of integrating into non-dividing cells (See, e.g., U.S. Pat. Nos. 5,994,136 and 6,013,516, both of which are incorporated herein by reference).

As used herein, the term "adeno-associated virus (AAV) vector" refers to a vector derived from an adeno-associated virus serotype, including without limitation, AAV-1, AAV-2, AAV-3, AAV-4, AAV-5, AAV-6, AAV-7, AAV-8, AAV-9, etc. AAV vectors can have one or more of the AAV wild-type genes deleted in whole or part, preferably the rep and/or cap genes, but retain functional flanking ITR sequences.

As used herein the term, the term "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reaction that occur within a natural environment.

As used herein, the term "host cell" refers to any eukaryotic cell (e.g., mammalian cells, avian cells, amphibian cells, plant cells, fish cells, and insect cells), whether located in vitro or in vivo.

As used herein, the term "next-generation sequencing" or "NGS" can refer to sequencing technologies that have the capacity to sequence polynucleotides at speeds that were unprecedented using conventional sequencing methods (e.g., standard Sanger or Maxam-Gilbert sequencing methods). These unprecedented speeds are achieved by performing and reading out thousands to millions of sequencing reactions in parallel. NGS sequencing platforms include, but are not limited to, the following: Massively Parallel Signature Sequencing (Lynx Therapeutics); 454 pyro-sequencing (454 Life Sciences/Roche Diagnostics); solid-phase, reversible dye-terminator sequencing (Solexa/Illumina); SOLiD technology (Applied Biosystems); Ion semiconductor sequencing (ion Torrent); and DNA nanoball sequencing (Complete Genomics). Descriptions of certain NGS platforms can be found in the following: Shendure, et al., "Next-generation DNA sequencing," Nature, 2008, vol. 26, No. 10, 135-1 145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11 (3):333-43; and Zhang et al., "The impact of next-generation sequencing on genomics", J Genet Genomics, 201, 38(3): 95-109.

The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous.

By "agent" is meant any small compound (e.g., small molecule), antibody, nucleic acid molecule, or polypeptide, or fragments thereof or cellular therapeutics such as allogeneic transplantation and/or CART-cell therapy.

As used herein, the term "nervous system" may refer to two components: the central nervous system, which includes, but is not limited to, the brain and the spinal cord and the peripheral nervous system, which includes, but is not limited to, ganglia and the peripheral nerves that lie outside the brain and the spinal cord. One of skill in the art realizes that the nervous system may be separated anatomically, but functionally they are interconnected and interactive.

The term "nervous tissue" refers to the main component of the nervous system. The types of nervous tissue include, but are not limited to, sensory neurons, motor neurons, interneurons, astrocytes, ependymal cells, oligodendrocytes, Schwann cells, and microglial cells.

The term "neurological disorder" refers to any disorder of the nervous system. Structural, biochemical, electrical and psychological abnormalities in the brain, spinal cord or other nerves can result in a range of symptoms. Exemplary neurological disorders include, but are not limited to, attention or cognitive disorders (e.g. Autistic Spectrum Disorders); mood disorder (e.g., major depressive disorder, bipolar disorder, and dysthymic disorder) or an anxiety disorder (e.g., panic disorder, posttraumatic stress disorder, obsessive-compulsive disorder and phobic disorder); neurodegenerative diseases (e.g., multiple sclerosis, Alzheimer's disease, amyotrophic lateral sclerosis (ALS), Parkinson's disease, Huntington's Disease, Guillain-Barre syndrome, myasthenia gravis, and chronic idiopathic demyelinating disease (CID)), movement disorders (e.g., dyskinesia, tremor, dystonia, chorea and ballism, tic syndromes, Tourette's Syndrome, myoclonus, drug-induced movement disorders, Wilson's Disease, Paroxysmal Dyskinesias, Stiff Man Syndrome and Akinetic-Ridgid Syndromes and Parkinsonism), epilepsy, tinnitus, pain, phantom pain, and diabetes induced neuropathy.

As used herein, the term "open state" refers to an activated state of ion channels, where the ion channels allow specific ions to pass through the ions channels, across the plasma membrane of a cell and conduct electrical current.

As used herein, the term "closed state" refers to an inactivated or deactivated state of ion channels, where the ion channels are impermeable to ions and do not conduct electrical current.

The term "stabilized step function mutations" refers to the mutations that extend the lifetime at which an ion channel can remain in the open state or has a longer timescale of ion channel deactivation, or both, Exemplary stabilized step function mutations include, but are not limited to, point mutation of ChR2 at C128 position, and point mutation of ChR2 at D156A.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Unless otherwise clear from context, all numerical values provided herein are modified by the term "about."

By "control" or "reference" is meant a standard of comparison. Methods to select and test control samples are within the ability of those in the art. Determination of statistical significance is within the ability of those skilled in the art, e.g., the number of standard deviations from the mean that constitute a positive result.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

Unless specifically stated or obvious from context, as used herein, the term "or" is understood to be inclusive. Unless specifically stated or obvious from context, as used herein, the terms "a", "an", and "the" are understood to be singular or plural.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The transitional term "comprising," which is synonymous with "including," "containing," or "characterized by," is inclusive or open-ended and does not exclude additional, non-recited elements or method steps. By contrast, the transitional phrase "consisting of" excludes any element, step, or ingredient not specified in the claim. The transitional phrase “consisting essentially of” limits the scope of a claim to the specified materials or steps “and those that do not materially affect the basic and novel characteristic(s)” of the claimed embodiments presented in the disclosure.

By “SFO nucleic acid molecule” is meant a polynucleotide that is 95%, 96%, 97%, 98%, or 100% identical to (omitted) (see e.g., Berndt, A., Yizhar, O., Gunaydin, L. et al. Bi-stable neural state switches. Nat Neurosci 12, 229-234 (2009)).

By "SSFO nucleic acid molecule” is meant a polynucleotide that is 95%, 96%, 97%, 98%, or 100% identical to the following sequence (SEQ ID NO: 1):

```
>SSFO
atggactatggcggcgctttgtctgccgtcggacgcgaacttttgttcgttactaatcct

gtggtggtgaacgggtccgtcctggtccctgaggatcaatgttactgtgccggatggatt

gaatctcgcggcacgaacggcgctcagaccgcgtcaaatgtcctgcagtggcttgcagca

ggattcagcattttgctgctgatgttctatgcctaccaaacctggaaatctacatgcggc

tgggaggagatctatgtgtgcgccattgaaatggttaaggtgattctcgagttctttttt

gagtttaagaatccctctatgctctaccttgccacaggacaccgggtgcagtggctgcgc

tatgcagagtggctgctcacttctcctgtcatccttatccacctgagcaacctcaccggc

ctgagcaacgactacagcaggagaaccatgggactccttgtctcagccatcgggactatc

gtgtgggggctaccagcgccatggcaaccggctatgttaaagtcatcttcttttgtctt

ggattgtgctatggcgcgaacacatttttttcacgccgccaaagcatatatcgagggttat

catactgtgccaaagggtcggtgccgccaggtcgtgaccggcatggcatggctgtttttc

gtgagctggggtatgttcccaattctcttcattttggggcccgaaggttttggcgtcctg

agcgtctatggctccaccgtaggtcacacgattattgatctgatgagtaaaaattgttgg

gggttgttgggacactacctgcgcgtcctgatccacgagcacatattgattcacggagat

atccgcaaaaccaccaaactgaacatcggcggaacggagatcgaggtcgagactctcgtc

gaagacgaagccgaggccggagccgtgccagttaactaa
```

By “SOUL nucleic acid molecule” is meant a polynucleotide that is 95%, 96%, 97%, 98%, or 100% identical to the following sequence (SEQ ID NO: 2):

```
>SOUL
atggactatggcggcgctttgtctgccgtcggacgcgaacttttgttcgttactaatcctgtggtggtga

acgggtccgtcctggtccctgaggatcaatgttactgtgccggatggattgaatctcgcggcacgaacgg

cgctcagaccgcgtcaaatgtcctgcagtggcttgcagcaggattcagcattttgctgctgatgttctat

gcctaccaaacctggaaatctacatgcggctgggaggagatctatgtgtgcgccattgaaatggttaagg

tgattctcgagttcttttttgagtttaagaatccctctatgctctaccttgccacaggacaccgggtgca

gtggctgcgctatgcagagtggctgctcacttctcctgtcatccttatccacctgagcaacctcaccggc

ctgagcaacgactacagcaggagaaccatgggactccttgtctcagccatcgggtgtatcgtgtgggggg

ctaccagcgccatggcaaccggctatgttaaagtcatcttcttttgtcttggattgtgctatggcgcgaa

cacatttttttcacgccgccaaagcatatatcgagggttatcatactgtgccaaagggtcggtgccgccag

gtcgtgaccggcatggcatggctgtttttcgtgagctggggtatgttcccaattctcttcattttggggc

ccgaaggttttggcgtcctgagcgtctatggctccaccgtaggtcacacgattattgatctgatgagtaa

aaattgttgggggttgttgggacactacctgcgcgtcctgatccacgagcacatattgattcacggagat

atccgcaaaaccaccaaactgaacatcggcggaacggagatcgaggtcgagactctcgtcgaagacgaag

ccgaggccggagccgtgccagttaactaa
```

By “rAAV-hSyn1-P2A-tdTomato nucleic acid molecule” is meant a polynucleotide that is 95%, 96%, 97%, 98%, or 100% identical to the following sequence (SEQ ID NO: 3).

```
>rAAV-hSyn1-P2A-tdTomato
CCCCCCTATCTCGCGCCTCGCGTGGTGCGGTCCGGCTGGGCCGGCGGCGGCGCGGACGCGACCAAGGTGG

CCGGGAAGGGGAGTTTGCGGGGGACCGGCGAGTGACGTCAGCGCGCCTTCAGTGCTGAGGCGGCGGTGGC

GCGCGCCGCCAGGCGGGGGCGAAGGCACTGTCCGCGGTGCTGAAGCTGGCAGTGCGCACGCGCCTCGCCG
```

-continued

CATCCTGTTTCCCCTCCCCCTCTCTGATAGGGGATGCGCAATTTGGGGAATGGGGGTTGGGTGCTTGTCC

AGTGGGTCGGGGTCGGTCGTCAGGTAGGCACCCCCACCCCGCCTCATCCTGGTCCTAAAACCCACTTGCA

CTCATACGCAGGGCCCTCTGCAGTCTAGACACTTAATTAAACGCGTGCGGCCGCAGGAACCCCTAGTGAT

GGAGTTGGCCACTCCCTCTCTGCGCGCTCGCTCGCTCACTGAGGCCGGGCGACCAAAGGTCGCCCGACGC

CCGGGCGGCCTCAGTGAGCGAGCGAGCGCGCAGCTGCCTGCAGGACATGTGAGCAAAAGGCCAGCAAAAG

GCCAGGAACCGTAAAAAGGCCGCGTTGCTGGCGTTTTTCCATAGGCTCCGCCCCCCTGACGAGCATCACA

AAAATCGACGCTCAAGTCAGAGGTGGCGAAACCCGACAGGACTATAAAGATACCAGGCGTTTCCCCCTGG

AAGCTCCCTCGTGCGCTCTCCTGTTCCGACCCTGCCGCTTACCGGATACCTGTCCGCCTTTCTCCCTTCG

GGAAGCGTGGCGCTTTCTCATAGCTCACGCTGTAGGTATCTCAGTTCGGTGTAGGTCGTTCGCTCCAAGC

TGGGCTGTGTGCACGAACCCCCCGTTCAGCCCGACCGCTGCGCCTTATCCGGTAACTATCGTCTTGAGTC

CAACCCGGTAAGACACGACTTATCGCCACTGGCAGCAGCCACTGGTAACAGGATTAGCAGAGCGAGGTAT

GTAGGCGGTGCTACAGAGTTCTTGAAGTGGTGGCCTAACTACGGCTACACTAGAAGAACAGTATTTGGTA

TCTGCGCTCTGCTGAAGCCAGTTACCTTCGGAAAAAGAGTTGGTAGCTCTTGATCCGGCAAACAAACCAC

CGCTGGTAGCGGTGGTTTTTTTGTTTGCAAGCAGCAGATTACGCGCAGAAAAAAAGGATCTCAAGAAGAT

CCTTTGATCTTTTCTACGGGGTCTGACGCTCAGTGGAACGAAAACTCACGTTAAGGGATTTTGGTCATGA

GATTATCAAAAAGGATCTTCACCTAGATCCTTTTAAATTAAAAATGAAGTTTTAAATCAATCTAAAGTAT

ATATGAGTAAACTTGGTCTGACAGTTACCAATGCTTAATCAGTGAGGCACCTATCTCAGCGATCTGTCTA

TTTCGTTCATCCATAGTTGCCTGACTCCCCGTCGTGTAGATAACTACGATACGGGAGGGCTTACCATCTG

GCCCCAGTGCTGCAATGATACCGCGAGACCCACGCTCACCGGCTCCAGATTTATCAGCAATAAACCAGCC

AGCCGGAAGGGCCGAGCGCAGAAGTGGTCCTGCAACTTTATCCGCCTCCATCCAGTCTATTAATTGTTGC

CGGGAAGCTAGAGTAAGTAGTTCGCCAGTTAATAGTTTGCGCAACGTTGTTGCCATTGCTACAGGCATCG

TGGTGTCACGCTCGTCGTTTGGTATGGCTTCATTCAGCTCCGGTTCCCAACGATCAAGGCGAGTTACATG

ATCCCCCATGTTGTGCAAAAAAGCGGTTAGCTCCTTCGGTCCTCCGATCGTTGTCAGAAGTAAGTTGGCC

GCAGTGTTATCACTCATGGTTATGGCAGCACTGCATAATTCTCTTACTGTCATGCCATCCGTAAGATGCT

TTTCTGTGACTGGTGAGTACTCAACCAAGTCATTCTGAGAATAGTGTATGCGGCGACCGAGTTGCTCTTG

CCCGGCGTCAATACGGGATAATACCGCGCCACATAGCAGAACTTTAAAAGTGCTCATCATTGGAAAACGT

TCTTCGGGGCGAAAACTCTCAAGGATCTTACCGCTGTTGAGATCCAGTTCGATGTAACCCACTCGTGCAC

CCAACTGATCTTCAGCATCTTTTACTTTCACCAGCGTTTCTGGGTGAGCAAAAACAGGAAGGCAAAATGC

CGCAAAAAAGGGAATAAGGGCGACACGGAAATGTTGAATACTCATACTCTTCCTTTTTCAATATTATTGA

AGCATTTATCAGGGTTATTGTCTCATGAGCGGATACATATTTGAATGTATTTAGAAAAATAAACAAATAG

GGGTTCCGCGCACATTTCCCCGAAAAGTGCCACCTGACGTCTAAGAAACCATTATTATCATGACATTAAC

CTATAAAAATAGGCGTATCACGAGGCCCTTTCGTCTCGCGCGTTTCGGTGATGACGGTGAAAACCTCTGA

CACATGCAGCTCCCGGAGACGGTCACAGCTTGTCTGTAAGCGGATGCCGGGAGCAGACAAGCCCGTCAGG

GCGCGTCAGCGGGTGTTGGCGGGTGTCGGGGCTGGCTTAACTATGCGGCATCAGAGCAGATTGTACTGAG

AGTGCACCATAAAATTGTAAACGTTAATATTTTGTTAAAATTCGCGTTAAATTTTTGTTAAATCAGCTCA

TTTTTTAACCAATAGACCGAAATCGGCAAAATCCCTTATAAATCAAAAGAATAGCCCGAGATAGAGTTGA

GTGTTGTTCCAGTTTGGAACAAGAGTCCACTATTAAAGAACGTGGACTCCAACGTCAAAGGGCGAAAAAC

CGTCTATCAGGGCGATGGCCCACTACGTGAACCATCACCCAAATCAAGTTTTTTGGGGTCGAGGTGCCGT

AAAGCACTAAATCGGAACCCTAAAGGGAGCCCCCGATTTAGAGCTTGACGGGGAAAGCCGGCGAACGTGG

CGAGAAAGGAAGGGAAGAAAGCGAAAGGAGCGGGCGCTAAGGCGCTGGCAAGTGTAGCGGTCACGCTGCG

-continued

CGTAACCACCACACCCGCCGCGCTTAATGCGCCGCTACAGGGCGCGTACTATGGTTGCTTTGACGTATGC

GGTGTGAAATACCGCACAGATGCGTAAGGAGAAAATACCGCATCAGGCGCCCCTGCAGGCAGCTGCGCGC

TCGCTCGCTCACTGAGGCCGCCCGGGCAAAGCCCGGGCGTCGGGCGACCTTTGGTCGCCCGGCCTCAGTG

AGCGAGCGAGCGCGCAGAGAGGGAGTGGCCAACTCCATCACTAGGGGTTCCTGCGGCCGCTCGGTCCGCA

CGTGGTTACCTACAAAATCAGAAGGACAGGGAAGGGAGCAGTGGTTCACGCCTGTAATCCCAGCAATTTG

GGAGGCCAAGGTGGGTAGATCACCTGAGATTAGGAGTTGGAGACCAGCCTGGCCAATATGGTGAAACCCC

GTCTCTACCAAAAAAACAAAAATTAGCTGAGCCTGGTCATGCATGCCTGGAATCCCAACAACTCGGGAGG

CTGAGGCAGGAGAATCGCTTGAACCCAGGAGGCGGAGATTGCAGTGAGCCAAGATTGTGCCACTGCACTC

CAGCTTGGTTCCCAATAGACCCCGCAGGCCCTACAGGTTGTCTTCCCAACTTGCCCCTTGCTCCATACCA

CCCCCCTCCACCCCATAATATTATAGAAGGACACCTAGTCAGACAAAATGATGCAACTTAATTTTATTAG

GACAAGGCTGGTGGGCACTGGAGTGGCAACTTCCAGGGCCAGGAGAGGCACTGGGGAGGGGTCACAGGGA

TGCCACCCGTAGATCTCTCGAGCAGCGCTCGGTATCGATGCGGGGAGGCGGCCCAAAGGGAGATCCGACT

CGTCTGAGGGCGAAGGCGAAGACGCGGAAGAGGCCGCAGAGCCGGCAGCAGGCCGCGGGAAGGAAGGTCC

GCTGGATTGAGGGCCGAAGGGACGTAGCAGAAGGACGTCCCGCGCAGAATCCAGGTGGCAACATAGGCGA

GCAGCCAAGGAAAGGACGATGATTTCCCCGACAACACCACGGAATTGTCAGTGCCCAACAGCCGAGCCCC

TGTCCAGCAGCGGGCAAGGCAGGCGGCGATGAGTTCCGCCGTGGCAATAGGGAGGGGGAAAGCGAAAGTC

CCGGAAAGGAGCTGACAGGTGGTGGCAATGCCCCAACCAGTGGGGGTTGCGTCAGCAAACACAGTGCACA

CCACGCCACGTTGCCTGACAACGGGCCACAACTCCTCATAAAGAGACAGCAACCAGGATTTATACAAGGA

GGAGAAAATGAAAGCCATACGGGAAGCAATAGCATGATACAAAGGCATTAAAGCAGCGTATCCACATAGC

GTAAAAGGAGCAACATAGTTAAGAATACCAGTCAATCTTTCACAAATTTTGTAATCCAGAGGTTGATTAT

CGATAAGCTTGATATCGAATTCCCTGCAGGGGCGCGCCGTCGACTTACTTGTACAGCTCGTCCATGCCGT

ACAGGAACAGGTGGTGGCGGCCCTCGGAGCGCTCGTACTGTTCCACGATGGTGTAGTCCTCGTTGTGGGA

GGTGATGTCCAGCTTGGTGTCCACGTAGTAGTAGCCGGGCAGTTGCACGGGCTTCTTGGCCATGTAGATG

GTCTTGAACTCCACCAGGTAGTGGCCGCCGTCCTTCAGCTTCAGGGCCTGGTGGATCTCGCCCTTCAGCA

CGCCGTCGCGGGGGTACAGGCGCTCGGTGGAGGCCTCCCAGCCCATGGTCTTCTTCTGCATTACGGGGCC

GTCGGGGGGGAAGTTGGTGCCGCGCATCTTCACCTTGTAGATCAGCGTGCCGTCCTGCAGGGAGGAGTCC

TGGGTCACGGTCACCAGACCGCCGTCCTCGAAGTTCATCACGCGCTCCCACTTGAAGCCCTCGGGGAAGG

ACAGCTTCTTGTAATCGGGGATGTCGGCGGGGTGCTTCACGTACGCCTTGGAGCCGTACATGAACTGGGG

GGACAGGATGTCCCAGGCGAAGGGCAGGGGGCCGCCCTTGGTCACCTTCAGCTTGGCGGTCTGGGTGCCC

TCGTAGGGGCGGCCCTCGCCCTCGCCCTCGATCTCGAACTCGTGGCCGTTCATGGAGCCCTCCATGCGCA

CCTTGAAGCGCATGAACTCTTTGATGACCTCCTCGCCCTTGCTCACCACCTTCCTCTTCTTCTTGGGGGC

CATTCTAGATGGCCCGGGATTCTCTTCGACATCCCCTGCTTGTTTCAACAGGGAGAAGTTAGTGGCTCCG

CTTCCGTTATCCTTCGCTGTCATCATTTGTACAAACTCTTCGTAGTTTACCTGACCATCCCCATCGATGT

CTGCTTCCCTGATCATTTCATCAACCTCTTCATCTGTTAACTTCTCTCCAAGGTTTGTCATCACGTGGCG

AAGCTCTGCTGCACTGATGTAGCCATTGCCATCCTTATCAAACACACCGAACGCTTCTCTAATTTCTTCT

TCCGTGTCCCTGTATTTCATTTTTCTTGCCATCATTGTCAGGAACTCAGGGAAGTCGATTGTGCCGTCAC

CGTCGGCATCTACTTCATTGATCATGTCCTGCAGCTCTGCTTCTGTGGGGTTCTGCCCCAGAGACCGCAT

CACCGTCCCCAGCTCCTTGGTTGTTATTGTCCCATCCCCGTCCTTGTCAAATAGGGAGAAAGCCTCTTTA

AATTCTGCGATCTGCTCTTCAGTCAGTTGGTCCGGCAGGTTGTACTCCAGCTTGTGCCCCAGGATGTTGC

CGTCCTCCTTGAAGTCGATGCCCTTCAGCTCGATGCGGTTCACCAGGGTGTCGCCCTCGAACTTCACCTC

GGCGCGGGTCTTGTAGTTGCCGTCGTCCTTGAAGAAGATGGTGCGCTCCTGGATGTAGCCTTCGGGCATG

-continued

```
GCGGACTTGAAGAAGTCGTGCTGCTTCATGTGGTCGGGGTAGCGGCTGAAGCACTGCACGCCGTAGGTCA

GGGTGGTCACGAGGGTGGGCCAGGGCACGGGCAGCTTGCCGGTGGTGCAGATGAACTTCAGGGTCAGCTT

GCCGTAGGTGGCATCGCCCTCACCCTCGCCGGACACGCTGAACTTGTGGCCGTTTACGTCGCCGTCCAGC

TCGACCAGGATGGGCACCACCCCGGTGAACAGCTCCTCGCCCTTGCTCACCATGCTCCCTCCGGTACCGC

CCTTGTACAGCTCGTCCATGCCGAGAGTGATCCCGGCGGCGGTCACGAACTCCAGCAGGACCATGTGATC

GCGCTTCTCGTTGGGGTCTTTCGAAAGTTTGGACTGCACGCTCAGGTAGTGGTTGTCGGGCAGCAGCACG

GGGCCGTCGCCGATGGGGGTGTTCTGCTGGTAGTGGTAGGCGAGCTGCACGCCGCCGTCCTCGATGTTGT

GGCGGATGTGGAAGTTCGCCTTGATGCCGTTCTTCTGCTTGTCGGCCTTGATATAGACGTTCTCGAGTGA

GCTCAGCCGACCTATAGCTCTGACTGCGTGACCTGTCTTATTCCACTTACGACGTGATGAGTCGACCATG

GTGGCGAGATCCTTATCGTCATCGTCGTACAGATCCCGACCCATTTGCTGTCCACCAGTCATGCTAGCCA

TACCATGATGATGATGATGATGAGAACCCATGGTGGCGCCGGATCCTCTAGCCGGTTTCTCGACTGCGCT

CTCAGGCACGACACGACTCCTCCGCTGCCCACCGCAGACTGAGGCAGCGCTGAGTCGCCGGCGCCGCAGC

GCAGATGGTCGCGCCCGTG
```

By “rAAV-hSyn1-SSFO-P2A-tdTomato nucleic acid molecule” is meant a polynucleotide that is 95%, 96%, 97%, 98%, or 100% identical to (omitted).

By “rAAV-hSyn1-SOUL-P2A-tdTomato nucleic acid molecule” is meant a polynucleotide that is 95%, 96%, 97%, 98%, or 100% identical to (omitted).

By “Ai9 nucleic acid molecule” is meant a polynucleotide that is 95%, 96%, 97%, 98%, or 100% identical to (omitted) (Madisen L, Zwingman T A, Sunkin S M, et al. A robust and high-throughput Cre reporting and characterization system for the whole mouse brain. Nat Neurosci. 2010; 13 (1): 133-140. doi: 10.1038/nn.2467).

By “Ai9-SOUL-P2A-tdTomato nucleic acid molecule” is meant a polynucleotide that is 95%, 96%, 97%, 98%, or 100% identical to (omitted).

The embodiments set forth below and recited in the claims can be understood in view of the above definitions.

Other features and advantages of the disclosure will be apparent from the following description of the preferred embodiments thereof, and from the claims. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All published foreign patents and patent applications cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

The following detailed description, given by way of example, but not intended to limit the disclosure solely to the specific embodiments described, may best be understood in conjunction with the accompanying drawings.

FIG. 1A shows representative traces of primary cultured hippocampal neurons expressing SSFO (top) and SOUL (bottom) photocurrent responses to 470 nm light pulses of indicated power (3 μW/mm2, 8 μW/mm2, 20 μW/mm2, 60 μW/mm2, 1 mW/mm2). FIG. 1B is a graph representing summary data for the photocurrents in response to different levels of laser powers. Statistical analysis for this data was done by an unpaired t-test with Holm-Sidak post-hoc analysis (*, $P<0.05$; , $P<0.01$; $P=0.013$, 605 0.019, 0.010, 0.002 and 0.004 from lowest to highest irradiance. SOUL, n=17 neurons; SSFO, n=15 neurons. Bar graph represents±SEM). FIG. 1C is a graph representing maximal photocurrent amplitude recorded from neurons expressing SSFO or SOUL. Statistical analysis for this data was done with an unpaired t-test (, $P<0.01$, $P=0.0027$; SOUL, n=17 neurons; SSFO, n=15 neurons. Bar graph represents±SEM).

FIG. 3A shows a schematic of in vivo recording and transcranial stimulation of MD with SOUL (left) or SSFO (right) in awake mice. Scale bar, 1 mm. Gray bar, optical fiber; blue region, illumination. FIG. 3B presents a raster plot of the representative recording of the neuron from SSFO- (top panel) or SOUL-expressing (bottom panel) MD during blue and orange light illumination (colored bars). FIG. 3C shows a mean (±SEM) firing rate (normalized to baseline) across neurons in SOUL- (dark green circle) or SSFO-expressing (brown circle) MD transcranially stimulated with blue light of different intensities (*, P<0.05; , P<0.01; *, P<0.001; two-tailed Wilcoxon Signed Rank Tests; SOUL, n=36; SSFO, n=31 neurons from 2 mice). FIG. 3D presents a schematic of transcranial optical stimulation (blue) of SOUL-expressing LH (red) through the intact skull (gray) of awake mice. FIG. 3E shows a coronal section of mice injected with SOUL-P2A-tdTomato in LH, expressing tdTomato (red) in LH and stained for DAPI (blue). Scale bar, 1 mm. FIG. 3F presents representative confocal images of LH sections from mice expressing mCherry (red, top panel) or SOUL-P2A-tdTomato (red, bottom panel) and stained for c-Fos (green). Scale bar, 20 μm. FIG. 3G shows mean cell counts of c-Fos+ cells in LH of mice injected with AAVs coding SOUL or mCherry, as in (e). (Unpaired t-test; *, P<0.05, P=0.035; SOUL, n=3 mice; mCherry, n=3 mice; Bar graph represents±SEM). FIG. 3H presents scatter plots depicting firing rate of neurons from SSFO or SOUL-expressing MD with transcranial illuminations and comparing pre-stimulation firing rates (baseline) to those following transcranial blue light stimulation for the data shown in FIG. 3C. n=31 neurons from the SSFO-expressing MD and 37 neurons from the SOUL-expressing MD from 2 animals.

FIG. 4A shows a schematic of transcranial stimulation of SOUL expressed in bilateral LH (red) in awake food-deprived mice. FIG. 4B shows a coronal section of SOUL knock-in mice injected with CaMKII-Cre in LH, expressing tdTomato (red) in LH and stained for DAPI (blue). Scale bar, 1 mm. FIG. 4C shows a confocal image of SOUL-P2A-tdTomato expression in LH neurons. Scale bar, 40 μm. FIG. 4D shows mean (±SEM) food consumption during 10 minutes after SOUL activation (ON) and during 10 minutes after SOUL deactivation (OFF) of LH across SOUL-expressing mice and control mice (CaMKIIa::SOUL, n=4 mice; Control, n=4 mice, two-way ANOVA with Bonferroni post-hoc analysis; *, P<0.05, F (1, 12)=7.647).

FIG. 5A shows a schematic of in vivo transcranial stimulation and the cortical area (black square) right underneath the stimulation site. The black squared area was used for lba-1 immunoactivity quantifications. FIG. 5B presents representative confocal images of lba-1 immunoactivity of black squared area in FIG. 5A of mice with no treatment (NT), mice with blue and orange light transcranial illumination (Transcranial); mice with fiber implantation (Fiber); or corresponding cortical area contralateral to implant hemisphere of the fiber-implanted mice (Contralateral). FIG. 5C shows quantification of lba-1 immunoactivity of black squared area in FIG. 5A of mice with no treatment (NT), mice with blue and orange light transcranial illumination (Transcranial); mice with fiber implantation (Fiber); or corresponding cortical area contralateral to implant hemisphere of the fiber-implanted mice (Contralateral) (Scale bar, 20 m; One way ANOVA with Tukey's post-hoc analysis; ****, P<0.0001; F (3, 16)=60.51; NS, not significant; n=5 mice for each group; bars and error bars represents mean±SEM).

FIG. 6A presents a schematic illustration of a cross-section of the chamber and the minimally invasive optogenetic method. FIG. 6B and FIG. 6D depict raster plots (top panel) and mean firing rate over time (bottom panel) for two example single neurons during multiple trials with blue and orange light illumination (color bars), BS: baseline; BL: blue-light; PB: post-blue; OL: orange light; PO: post-orange. FIG. 6C and FIG. 6E show firing rates of the units in FIG. 6B and FIG. 6D, respectively, during baseline (BS), post-blue (PB) and post-orange (PO) periods. ***, P<0.001, paired t-test; NS, not significant. Spikes are down sampled in FIG. 6B and FIG. 6D for better visualization. FIG. 6F shows the percentage of units with significantly increased or decreased firing rate after blue light stimulation (compared to baseline; paired t-tests, alpha<0.05; see Example 6), with (black) or without (grey) returning to baseline after orange light illumination (Paired t-tests, alpha<0.05; n=215). FIG. 6G displays a frequency histogram of firing rate modulation magnitudes (percent change from baseline, logarithmic scale) among modulated units (n=128). FIG. 6H presents a frequency histogram of firing rate modulation latency (logarithmic scale) after blue light onset among modulated units. FIG. 6I shows percentage of modulated units with a modulation duration of at least 40, 80 or 120 s (complete post-blue period) after blue light offset. FIG. 6J presents recording depth and magnitude of all modulated units (circles). FIG. 6K shows percentage of modulated units at different recording depths.

FIG. 7A shows local field potential amplitude over time for an example recording channel before (top panel) and after (bottom panel) blue light stimulation in one representative trial. FIG. 7B and FIG. 7C show spectrograms of two example recording channels showing mean LFP power across trials (% change from baseline, color scale) as a function of time and frequency. Colored bars, blue and orange light illumination periods. Time-frequency clusters with significant modulation compared to baseline are indicated by black outlines (see Example 6). High and low frequencies are shown at different scales. FIG. 7D depicts percentage of channels (n=176) with significant power modulation at each frequency. Color bars indicate frequency bands with significant peaks. FIG. 7E presents Mean (±SEM) power modulation magnitude (% change) across all modulated channels. FIG. 7F presents latency across all modulated channels. FIG. 7G presents duration across all modulated channels.

FIG. 8A shows summary data for resting membrane potential of cultured cells expressing RFP (Con) and SOUL. FIG. 8B shows summary data for membrane resistance of cultured cells expressing RFP (Con) and SOUL. FIG. 8C shows summary data for Tau of cultured cells expressing RFP (Con) and SOUL. FIG. 8D shows summary data for capacitance of cultured cells expressing RFP (Con) and SOUL. (Unpaired t-test; P=0.458, P=0.688, P=0.577, P=0.600 from (a) to (d), respectively; n=10 neurons/group; Bar graph represents±SEM).

FIG. 9A presents a strategy used for targeting a Cre-inducible SOUL expression cassette into the endogenous Rosa26 genomic locus. Lines represent insertion of the cassette into the Rosa26 locus. FIG. 9B shows Cre-induced excision of the floxed-STOP cassette.

FIG. 10A shows a sagittal section of native tdTomato fluorescence in fixed tissue from PV-Cre::SOUL mice. Scale bar=2 mm. TRN: thalamic reticular nucleus. FIG. 10B shows a sagittal section of native tdTomato fluorescence in fixed tissue from ChAT-Cre:SOUL mice. Scale bar=2 mm. BF: basal forebrain.

FIG. 11A presents images of tdTomato expression (red) in PV-expressing neurons (green) and their colocalization (yellow) in the hippocampus (left panel), cerebellum (middle panel) and thalamic reticular nucleus (TRN, right panel) in PV-Cre::SOUL mice. Scale bar=100 mm. FIG. 11B presents images of tdTomato expression (anti-RFP, red) in ChAT-expressing neurons (green) and their colocalization (yellow) in the striatum (left panel) and nucleus vertical limb of diagonal band (VDB, right panel) in ChAT-Cre:SOUL mice. Scale bar=100 mm. FIG. 11C presents images of cellular tdTomato distribution (red), 2A-SOUL distribution (green) and merged image (yellow) in striatal ChAT neurons. Scale bar=40 μm.

FIG. 12A presents a schematic of in vivo recording and intracranial optical stimulation of SSFO or SOUL with implanted fibers in MD. Note that angled optic fibers are placed medial to their respective activation target delivering the light laterally to avoid cross activation of the two opsins. Scale bar, 1 mm. FIG. 12B presents a raster plot of the representative neuron from SSFO- or SOUL-expressing MD showing light activated responses exclusively when light is being delivered through the respective optic fiber. Note that the neuron from SOUL-expressing MD starts responding at lower light levels compared to the one from SSFO-expressing MD. Color bars represent blue and orange light stimulations. FIG. 12C presents a mean (±SEM) firing rate (normalized to baseline) across neurons from SOUL- (dark green circle) or SSFO-expressing (brown circle) MD intracranially stimulated with blue light of different intensities. (**, P<0.01; two-tailed Wilcoxon Signed Rank Tests; n=26 neurons in the SSFO-expressing MD and 21 in the SOUL-expressing MD from 2 animals).

FIG. 13 A and FIG. 13B present sagittal sections which depict the expression of c-fos from PV-Cre:SOUL mice in the dark and under normal ambient light (150 lux), respectively. Scale bar=1 mm. FIG. 13C and FIG. 13D show images of c-fos expression in layer II-III cortical neurons of PV-Cre:SOUL mice in the dark and in normal ambient light, respectively. Scale bar=50 μm.

FIG. 14A and FIG. 14B show sagittal sections show the expression of c-fos from ChAT-Cre:SOUL mice in the dark and under normal ambient light (150 lux), respectively. Scale bar=1 mm. FIG. 14C and FIG. 14D depict the c-fos expression in layer II-III cortical neurons of ChAT-Cre:SOUL mice in the dark and under normal ambient light, respectively. Scale bar=50 μm. The arrows indicate the SOUL positive cells. FIG. 14E presents a graph of quantification of the percentage of td-Tomato+ neurons that is c-fos+. Data were taken from 6 slices from one pair of PV-Cre:SOUL mice and 6 slices from 2 pairs of ChAT-Cre:SOUL mice.

FIG. 15A to FIG. 15C show sagittal sections show the expression of c-fos from an Nex-Cre:SOUL mouse in the dark, under normal ambient light (150 Lux) and under strong light (468 lux), respectively. The bracket indicates visual cortex. Scale bar=1 mm. Red: native tdTomato native fluorescence, green: c-fos immunofluorescence. FIG. 15D shows images of a wholemount retina from an Nex-Cre:SOUL mouse. The left panel shows a wholemount retina from an Nex-Cre:SOUL mouse. The right panel shows the zoom-in picture of the region marked with a white square in the left. SOUL-P2A-tdTomato is strongly expressed in the retina of a Nex-Cre:SOUL mouse. Scale bar=50 μm. Red: native tdTomato fluorescence.

FIG. 16A presents a schematic showing the region of dorsal lateral geniculate nucleus (dLGN, arrow). Scale bar=1 mm. FIG. 16B shows representative confocal images of dLGN sections from mice with transcranial illumination (w/ light, top panel) or without transcranial illumination (w/o light, bottom panel) and stained for c-Fos (green). Scale bar=50 μm. FIG. 16C shows mean cell counts of c-Fos+ cells in dLGN of mice with transcranial illumination (w/ light) or without transcranial illumination (w/o light), as in (b). (Unpaired t-test; P=0.88; w/ light, n=5 mice; w/o light, n=5 mice; Bar graph represents SEM). FIG. 16D presents a schematic showing the region of primary visual cortex (V1, arrow). Scale bar=1 mm. FIG. 16E presents representative confocal images of V1 sections from mice with transcranial illumination (w/ light, top panel) or without transcranial illumination (w/o light, bottom panel) and stained for c-Fos (green). Scale bar=50 μm. FIG. 16F depicts mean cell counts of c-Fos+ cells in V1 of mice with transcranial illumination (w/ light) or without transcranial illumination (w/o light), as in FIG. 16E. (Unpaired t-test; P=0.73; w/ light, n=5 mice; w/o light, n=5 mice; Bar graph represents±SEM).

FIG. 17A shows a photograph of cranial chamber showing transparent artificial dura over right prefrontal cortical surface. Blue lines, principal sulcus (PS) and arcuate sulcus (AS). Black dots, virus injection sites. Scale bar=4 mm. FIG. 17B shows a red-filtered photograph of cranial chamber in (a) showing tdTomato epifluorescence region (green dashed line) around virus injection sites. Scale bar=4 mm. FIG. 17C presents a raster plot (top) and mean firing rate over time (bottom) for an example unit during multiple trials with blue and orange light stimulation (color bars). Spikes are down-sampled for better visualization. FIG. 17D presents a firing rate of the unit in FIG. 17C during baseline (BS), post-blue (PB) and post-orange (PO) periods. ***, P<0.001, paired t-test; N.S., not significant.

FIG. 18A presents a graph of percentage of single neurons and multiunits with significantly increased or decreased firing rate after blue light stimulation (compared to baseline; paired t-tests, alpha<0.05; see Example 6), with (black) or without (gray) returning to baseline after orange light stimulation (paired t-tests, alpha<0.05; single neurons, n=54; multiunits, n=161). FIG. 18B shows a baseline firing rate of activated and unactivated units (all single and multiunits). FIG. 18C shows a graph of recording depth and magnitude of units without significance of modulation effect.

FIG. 19 shows graphs of maximum temperature as a function of depth from cortical surface (dotted line) before (gray) and during (blue) exposure to 10 s of blue light stimulation (left) and 20 s of orange light stimulation (right).

FIG. 20A shows tyrosine hydroxylase (TH) and neuronal nuclei (NeuN) antibody staining in substantia *nigra pars compacta* (SNc) sections of saline control (left) and PD model (6-OHDA injected into SNc) (right) mice. DAPI staining is shown in blue. FIG. 20B shows PF→NAc circuit manipulation in PD mice by injecting retrograde RV expressing Cre in NAc, Cre-dependent SOUL-tdTomato virus in PF, 6-OHDA in SNc, and fibers attached to the skull above PF (left). Expression of SOUL-tdTomato in PF is shown at right. FIG. 20C shows representative ex vivo current (top) and voltage (bottom) traces from a SOUL-expressing $PF_{NAc}$ neuron showing blue-light activation and orange-light inactivation. FIG. 20D shows representative images of PF sections stained with cFos from mice expressing SOUL in PF neurons, including a no light group (SOUL−light) and a 5 min light activated group (SOUL+light) in the home cage. FIG. 20E shows that transcranial stimulation of $PF_{NAc}$ neurons rescued depression-like phenotypes of PD mice in sucrose preference (n=8 $WT_{mCh}$, n=8 $PD_{mCh}$, n=9 $PD_{SOUL}$, n=10 $PD_{SOUL}$ control), and forced swim and tail suspension tests (n=9 $WT_{mCh}$, n=8 $PD_{mCh}$, n=10 $PD_{SOUL}$, n=10 $PD_{SOUL}$ control). For the $PD_{SOUL}$ control group, orange light was delivered in vivo immediately after blue light application. Data are presented as mean±SEM; *P<0.05, P<0.01, *P<0.001. One-way ANOVA followed by Bonferroni post-hoc test.

DETAILED DESCRIPTION OF THE DISCLOSURE

Figure 1A:
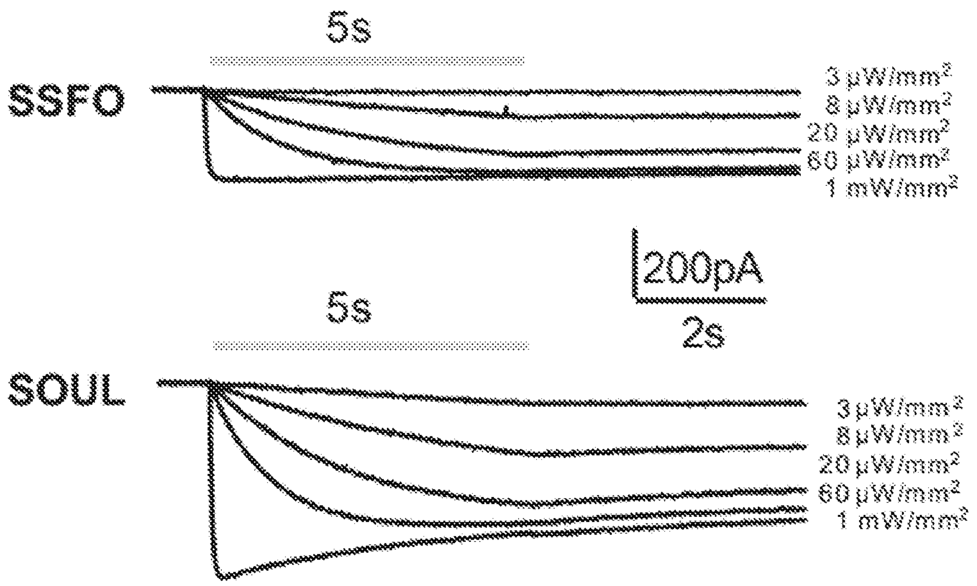
FIGS. 1A to 1C display representative traces, and two graphs, respectively, depicting an overview of in-vitro characterization of SOUL according to exemplary embodiments of the disclosure.

The current disclosure is based, at least in part, on the discovery of compositions and methods related to an engineered step-function opsin with ultra-high light sensitivity (referred to as "SOUL") that has advantageous properties for minimally invasive optogenetics via external optical stimulation (e.g., transcranial optical stimulation). According to the techniques disclosed herein, SOUL may be expressed in living cells (e.g., neurons) via the injection of an appropriate expression vector (e.g., rAAV-hSyn1-P2A-tdTomato). A light source may then be used with minimal invasiveness or non-invasiveness to stimulate and modulate neurons within a desired target region of a brain. Advantageously, the techniques herein allow for the first time optogenetic stimulation of neurons in the brain even in applications where there is extensive attenuation of light (e.g., cells that are located at a significant distance from the light source). This advantage provides the ability to conduct optogenetic stimulation of cells that are normally refractory to light stimulation (e.g., neurons within deep brain tissues). Prior art optogenetic techniques typically employ surgical implants, which are associated with extensive damage to the brain and surrounding tissues. Advantageously, the techniques herein provide optogenetic stimulation without the need for a surgical implant. Additionally, as described further below, the compositions and methods disclosed herein provide significant benefits over prior art recognized optogenetic stimulation methods, particularly in contexts where a minimally invasive approach to optogenetic stimulation of cells (e.g., neuronal cells) is advantageous.

Various expressly contemplated components of certain compositions and methods of the instant disclosure are considered in additional detail below.

Overview

Methods to modulate neuronal activity in specific brain regions have led to fundamental insights into the causal role that these regions play in a wide variety of brain functions. Additionally, these methods have been used for the treatment of specific neurological diseases in which activation or inactivation of neuronal activity in a target brain region restores lost functions or ameliorates symptoms (Dzirasa and Lisanby, 2012). Most of these studies and clinical applications utilize direct electrical stimulation to the brain (Weaver et al., 2012). In the last decade, optogenetics has become increasingly popular as a viable alternative to these methods, providing cell-type and neural circuit specificity, millisecond temporal resolution, and high spatial precision, among other advantages (Bergs et al., 2018; Berndt et al., 2011; Boyden et al., 2005; Cavanaugh et al., 2012; Chow et al., 2010; Dawydow et al., 2014; Han et al., 2009; Hososhima et al., 2015; Kleinlogel et al., 2011; Lin et al., 2009; Nandy et al., 2019; Thyagarajan et al., 2010; Yizhar et al., 2011a). In various applications of optogenetics, opsins are utilized. Opsins are light-gated ion channels or pumps that absorb light at specific wavelengths. Upon activation by light, these channels and pumps respond by opening or closing, which conducts the flow of ions into or out of the cell. A variety of naturally occurring opsins (e.g., channel rhodopsins) that respond to different wavelengths of light, like blue or yellow light, have been identified. These various opsins also initiate different electrochemical responses (e.g, nonspecific cation influx, proton efflux, etc.).

However, a significant disadvantage in prior art applications of optogenetics, as with other perturbation methods, is the requirement to surgically implant devices that cause permanent damage to the brain, such as optical fibers. Mechanical strain associated with the implantation procedures causes the severing of capillaries and processes of neurons and glia, leading to significant neuronal loss and altered spine turnover, acute inflammatory responses, and chronic foreign body reactions (Polikov et al., 2005; Xu et al., 2007). These responses activate microglia and astrocytes within 500-600 μm from the implants (Szarowski et al., 2003), which subsequently affect neuronal activity, plasticity (Hauss-Wegrzyniak et al., 2002), and homeostasis (Luo and Chen, 2012). Lastly, the process of implanting prior art devices into the brain increases susceptibility to infection, which poses a significant health risk. Another challenge in the application of optogenetics stems from the fact that light is severely attenuated as it passes through brain tissue; consequently, the volume of brain around an implanted optical fiber that receives enough light for neurons to be optogenetically modulated is relatively small (Aravanis et al., 2007; Diester et al., 2011). This is particularly problematic when applying optogenetics to animal models with large brains (e.g., non-human primates, humans, etc.). Optogenetic methods modulate the spiking activity of neurons in both macaques and mice (Gerits and Vanduffel, 2013); however, one significant difference between these two animal models is that the number of neurons modulated by standard optogenetic methods in macaques is a smaller fraction of a given functional region than in mice because the macaque brain is orders of magnitude larger than the mouse brain (Diester et al., 2011). One way to increase the anatomical coverage of optogenetic stimulation is to illuminate the cortical surface from the outside, thus allowing light to cover a larger area by increasing the beam diameter, rather than increasing the light intensity from an intra-cortical fiber (Nassi et al., 2015).

To overcome the aforementioned challenges, the techniques herein provide compositions of a new step-function opsin with ultra-high light sensitivity (SOUL) and methods of using same for minimally invasive optogenetics via external optical stimulation. The step-function opsin (SFO) family was chosen as the parental base due to several advantages over other opsins (Berndt et al., 2009). First, the slow off kinetics of SFOs enables the ion channel to stay open for more than 30 minutes after light stimulation (Yizhar et al., 2011b). Thus, animals can be released from the light source while the neurons remain activated, a feature that is especially beneficial in large or freely-moving animals and for long-term, developmental, and clinical applications. Second, in contrast to traditional opsins that drive synchronized spiking in all opsin-expressing cells at a firing rate determined by the researcher, SFOs induce subthreshold depolarization that sensitizes the neurons to endogenous synaptic input and thus generates a modulated state of increased excitability (Berndt et al., 2009). Since neurons do not usually fire in millisecond-precise synchrony and the firing codes of neuronal ensembles under many specific contexts are largely unknown, using SFOs to effectively and reversibly increase neuronal excitability may be a more suitable way to define the physiological and causal importance of optogenetically-targeted neurons. Importantly, SFOs are highly sensitive to light due to their capability for photointegration (Mattis et al., 2011). The SFOs may be combined with particular mutations that increase the operational light sensitivity to generate a new step-function opsin with ultra-high light sensitivity (e.g., SOUL), which has extremely high light sensitivity that can undergo photoactivation under conditions of significantly attenuated light power.

As described in detail below, the techniques herein provide minimally invasive procedures that allow optogenetic activation with external illumination in both mice and macaques. Additionally, the working examples described below indicate that transcranial optical stimulation of SOUL causes reversible activation of neurons located in the lateral hypothalamus, one of the deepest regions of the mouse brain (as deep as 5.5 to 6.2 mm). Furthermore, these effects were strong enough to disrupt mouse feeding behaviors, which could be restored by the deactivation of SOUL with orange light. Unexpectedly, stimulation of SOUL from outside the dura modulates neuronal spiking and induces local field potential oscillations in the cortex, as demonstrated in macaque models. Thus, SOUL provides a minimally invasive approach to optogenetically manipulate neuronal activity in the living brain.

Parkinson's disease (PD) is a neurodegenerative disorder characterized by the loss of dopamine neurons from substantia *nigra pars compacta* (SNc), abnormal activity in the basal ganglia network, and severe motor dysfunction (Albin et al.). PD motor symptoms such as rigor, tremor, and bradykinesia are treated by levodopa administration (The Parkinson Study Group, Levodopa and the progression of Parkinson's disease), or high frequency deep brain stimulation (DBS) targeting the subthalamic nucleus (STN) region (Hamani et al.). In addition to motor symptoms, PD patients commonly experience debilitating non-motor phenotypes, including depression and anxiety (Poewe), which have received limited attention. Identifying neural circuit mechanisms responsible for both motor and non-motor deficits in PD may lead to the development of novel therapeutic approaches. Parafascicular (PF) thalamus has extensive connectivity with the basal ganglia (Saalmann; Smith et al.), critically contributes to motor behaviors (Brown et al.; Diaz-Hernandez et al.), and PF DBS can modulate pathophysiological changes relevant to PD (Carvalho et al.). It was observed herein that distinct PF thalamic subpopulations project to caudate putamen (CPu), subthalamic nucleus (STN), and nucleus accumbens (NAc). While PF→CPu and PF→STN circuits are critical for locomotion and motor learning, respectively, inhibition of the PF→NAc circuit induced a depression-like state. As detailed herein, in a mouse model of Parkinson's disease, activation of NAc-projecting PF neurons using SOUL rescued depression-like PD phenotypes, which indicated a direct application for SOUL in the treatment of non-motor symptoms in Parkinson's disease.

Step-Function Opsins

Step function or bi-stable opsins (SFOs) were created by modifying ChR2 to stabilize the open conducting state. The first SFO was generated by introducing a point mutation of ChR2 at the C128 position [ChR2(C128A), ChR2(C128S), or ChR2(C128T)]. This mutation increases the time the channel is in open state to tens of seconds, thus creating a depolarizing step upon brief light illumination (Berndt et al., 2009). Another variation of this, ChR2/D156A, has a deactivation timescale on the order of minutes (Bamann et al., 2010). Both the mutations were combined and incorporated to produce a stabilized SFO (SSFO), ChR2(C128S/D156A), which has a spontaneous deactivation lifetime of almost half an hour (Yizhar et al., 2011b). When using these SSFOs, photocurrents can be initiated with a brief, blue light pulse and terminated with a yellow light pulse, offering millisecond scale temporal precision of depolarization onset and offset coupled with a higher-rate spontaneous spiking pattern. SSFOs can induce peak photocurrent values in range of 250 pA to 450 pA, more specifically about 320 pA, about 330 pA, about 340 pA, about 350 pA, about 360, about 370 pA, or about 380 pA. SSFO is particularly useful for manipulating cellular activity in behavioral paradigms where connection to a fiber optic tether would be awkward. Because of its very long deactivation kinetics, animals may be briefly attached to a fiber optic cable for the initiation of neural activity with a blue light pulse, detached from the tether for behavioral testing, then attached again for termination of elevated neural activity with a yellow light pulse. SSFOs also present with extreme sensitivity to light (Tye and Deisseroth, 2012), making it possible to use SSFOs for applications of non-invasive optogenetic stimulation.

Retroviruses

Retroviruses refer to a family of viruses which have RNA and reverse transcriptase (RNA-dependent DNA polymerase), of which the latter is essential to the first stage of its self-replication for synthesizing complementary DNA on the base of template RNA of the virus. Retroviruses can be categorized into Orthoretrovirinae (includes oncoviruses and lentiviruses) and Spumaretrovirinae. The oncoviruses are thus termed because they can be associated with cancers and malignant infections. There may be mentioned, for example, leukemogenic viruses such as the avian leukemia virus (ALV), the murine leukemia virus (MULV), also called Moloney virus or simply MLV at some instances herein, the Abelson leukemia virus, the murine mammary tumor virus, the Mason-Pfizer monkey virus (or MPMV), the feline leukemia virus (FELV), human leukemia viruses such as HTLV1 (also named HTLV-I) and HTLV2 (also named HTLV-II), the simian leukemia virus or STLV, the bovine leukemia virus or BLV, the primate type D oncoviruses, the type B oncoviruses which are inducers of mammary tumors, or oncoviruses which cause a rapid cancer (such as the Rous sarcoma virus or RSV).

Although the term "oncovirus" is still commonly used, other terms can also be used such as Alpharetrovirus for avian leukosis virus and Rous sarcoma virus; Betaretrovirus for mouse mammary tumor virus; Gammaretrovirus for murine leukemia virus and feline leukemia virus; Deltaretrovirus for bovine leukemia virus and human T-lymphotropic virus; and Epsilonretrovirus for Walleye dermal sarcoma virus. The lentiviruses, such as Human Immunodeficiency Virus (HIV, also known as HTLV-III or LAV for lymphotrophic adenovirus and which can be distinguished within HTV-1 and HTV-2), are thus named because they are responsible for slow-progressing pathological conditions which very frequently involve immunosuppressive phenomena, including AIDS. Among the lentiviruses, the visna/maedi virus (or MW/Visna), equine infectious anemia virus (EIAV), caprine arthritis encephalitis virus (CAEV), simian immunodeficiency virus (SIV) can also be cited (See, e.g., WO2015001518A1, which is incorporated herein by reference).

The spumaviruses manifest fairly low specificity for a given cell type or a given species, and they are sometimes associated with immunosuppressive phenomena; that is the case, for example, for the simian foamy virus (or SFV), also named chimpanzee simian virus, the human foamy virus (or HFV), bovine syncytial virus (or BSV), feline syncytial virus (FSV) and the feline immunodeficiency virus.

Adeno-Associated Viruses (AAV)

Adeno-associated viruses (AAV) are small (about 20 nm) nonenveloped icosahedric ssDNA viruses, which depend on helper viruses (e.g., adenovirus or herpes simplex virus) for replication. To date, nine human serotypes have been characterized. About 80% of the population has detectable levels of anti-AAV antibodies, but there is no discernable pathology association with this virus. This fact and the ability of AAV to mediate transgene integration into a specific site in the human genome have made it an important candidate for use in gene therapy. The resulting knowledge about capsid structure and tolerance for peptide insertions has been described for use in the design of genome-free AAV-like particles (AAVLPs) as a novel high-density system for peptide vaccines. (Manzano-Szalai et al. *Viral Immunol.* 2014 Nov. 1; 27(9): 438-448). It is expressly contemplated herein that AAV VLPs can be used in the compositions and methods of the instant disclosure.

Viral Transfection of Mammalian Cells

In certain aspects, the compositions and methods of the present disclosure relate to production of virus-like particles (VLPs) using viral vector-mediated transfection of nucleic acids that encode for VLP-inducing agents. Viral vectors have received much attention in recent years and have become powerful tools for gene delivery in vitro and in vivo. In cultured cells, viruses are primarily used to achieve stable genomic integration and an inducible expression of transgenes. In vivo, viruses are often the only viable option when aiming at efficiently introducing transgenes into specific cell types, as is needed, for instance, in gene therapy. Virus-mediated transfection, also known as transduction, offers a means to reach hard-to-transfect cell types for protein overexpression or knockdown, and it is the most commonly used method in clinical research. Adenoviral, oncoretroviral, and lentiviral vectors have been used extensively for gene delivery in mammalian cell culture and in vivo. Other well-known examples for viral gene transfer include baculovirus and vaccinia virus-based vectors. Any of these and other art-recognized viral gene transfer systems are contemplated for use in the context of the instant disclosure.

A typical transduction protocol involves engineering of the recombinant virus carrying the transgene, amplification of recombinant viral particles in a packaging cell line, purification and titration of amplified viral particles, and subsequent infection of the cells of interest. While the achieved transduction efficiencies in primary cells and cell lines are quite high (~90-100%), only cells carrying the viral-specific receptor can be infected by the virus. It is also important to note that the packaging cell line used for viral amplification needs to be transfected with a non-viral transfection method Suitable mammalian cells that can be used for viral transduction include, but are not limited to, primary cells and cell lines, where suitable cell lines include, but are not limited to, 293 cells, COS cells, HeLa cells, Vero cells, 3T3 mouse fibroblasts, C3H10T1/2 fibroblasts, CHO cells, and the like. Non-limiting examples of suitable host cells include, e.g., HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In certain embodiments, exemplary mammalian cells for viral transduction are primary rat cortical neurons and/or primary rat hippocampal neurons, optionally those obtained from microsurgically dissected tissue, e.g., from E18 Sprague Dawley Rat.

Viral vectors have been employed in the study of various models of diseases such as metabolic, cardiovascular, muscular, hematologic, ophthalmologic, and infectious diseases and different types of cancer. Viral vectors such a retroviruses, adenoviruses, and herpes simplex viruses have been used in animal models and clinical trials of diseases such as, but not limited to, anaplastic thyroid cancer, carcinoma, hepatocellular carcinoma, glioma, hemophilia, Alzheimer's disease, sensory neuropathy, acquired immunodeficiency syndrome (AIDS), melanoma, Huntington's disease, and glioblastoma (Lundstrom. *Diseases.* 6(2) 42).

Neuronal Cell Disease Models

Animal modeling of human disease is a cornerstone to basic scientific studies of disease mechanisms and pre-clinical studies of potential therapies. Rapid progress in in vitro, in vivo, and ex vivo animal modeling has led to advancements in the understanding of fundamental disease mechanisms of many central nervous system (CNS) disorders, including but not limited to, initial cell death and later repair in stroke, motor and non-motor pathologies in Parkinson's disease, and axonal regeneration in peripheral and optic nerve injury, among many others. Ideally, animal modeling produces basic insights, new views of the human disease, and preclinical trials of novel therapies (Chesselet et al. *Neurotherapeutics.* 9(2): 241-244).

Many animal models have been used in the study of neurological disease such as rodents (rat and mice) and primates. The mouse model has been particularly studied extensively as a neurological disease model. The common house mouse (*Mus musculus*) has a genome with 97% homology to the human genome. Mouse models of neurological disorders can be usefully divided into whether or not the model is heritable. Human neurological disorders with a mutant gene component make ideal candidates for modelling via gene manipulation. It follows then that human neurological disorders with an identified underlying genetic component, for example Alzheimer's disease, have been extensively modelled using genetically manipulated mouse models. Alternatively an interesting neurological phenotype may be identified as a result of a spontaneous mutation in the wild type mouse population, for example the stargazer mouse. These spontaneous mutant mouse models are then bred to sustain the appropriate phenotype of interest. Clearly neurological disorders also have heritable traits that do not include mutant gene components but are well characterized risk factors for the disorder, for example the Apoe4 allele in AD. As these traits can be inherited from generation to generation they can also be included as heritable trait models. Mouse models that do not carry a heritable component are focused on replicating a phenotype characteristic of the relevant disorder. Those human disorders that do not have a defined genetic component, or in which a complex multi-gene interacting system is under investigation, are more readily modelled using non heritable mouse models that have an identified robust phenotype and are acquired by physical manipulation (Harper. *BBA.* 10: 785-795).

Where animal models are employed, in some embodiments, the specificity can be achieved by targeting specific regions of organs of the CNS (e.g., brain). For example, the regions of the brain including, but limited to, cortex, globus pallidus, thalamic reticular nucleus, striatum, hippocampus, cerebellum, mediodorsal thalamus, and regions of deep brain tissue such as lateral hypothalamus, are targeted for the treatment of different neurological disorders.

Where animal models are employed, in some embodiments, specificity can be achieved through delivery, such as via use of a pseudotyped virus that only infects neurons, or a subset of neurons, and/or passes the blood brain barrier. For example, the AAV-PHP.B2 capsid can be used (from www.nature.com/articles/nbt.3440) to generate AAV carrying the VLP-inducing and envelope transgenes. This AAV can be administered via IV, allowing for delivery of the transgenes to the brain. Cerebral spinal fluid (CSF) can then be harvested from the animal to measure transcriptomes in different structures in the brain (such as the hippocampus), as well as different cell types in the brain (such as glial cells).

Neuronal Tissue-Specific Promoters

In certain aspects, the compositions and methods of the present disclosure include components that impart tissue-specificity to formation of particular types of VLPs. In one exemplified embodiment, to successfully label VLPs from excitatory neurons, a CamKII promoter can be used to drive expression of both a VLP producing protein, such as MLV Gag, as well as a labeled envelope protein, such as FLAG-VSVG. Meanwhile, to successfully label VLPs from inhibitory neurons, a mDIx promoter can be used to drive expression of both a VLP producing protein such as MLV Gag, as well as a labeled envelope protein, such as HA-VSVG. Such a system allows for direct comparison in real-time (and across a time course) of excitatory neuron transcriptomes vs. inhibitory neuron transcriptomes, from living cells of each respective type, even in mixed culture. Examples of neural tissue-specific promoters that can be employed in the compositions and methods of the instant disclosure include, but are not limited to, mDIx, CamKII, Syn1, NSE, PDGF and Tal.

Compound Screening in Model Systems

Model systems, including laboratory animals, microorganisms, and cell- and tissue-based systems, are central to the discovery and development of new and better drugs for the treatment of human disease. Model systems such as animal models are essential for translation of drug findings from bench to bedside. Hence, critical evaluation of the face and predictive validity of these models is important. Reversely, clinical bedside findings that were not predicted by animal testing should be back translated and used to refine the animal models. Design, execution and reporting of results from animal model systems help to make preclinical data more reproducible and translatable to the clinic. Design of an animal model strategy is part of the translational plan rather than (a) single experiment(s). Data from animal models are essential in predicting the clinical outcome for a specific drug in development. Review, standardization and refinement of animal models by disease expert groups helps to improve rigor of animal model testing. It is important that the applied animal models are validated fit-for-purpose according to stringent criteria and reproducible. During drug development fit-for-purpose animal models are key for success in clinical translation, financial investments and support from the government to develop, optimize, validate and run such translation tools are important. Over time, this will be of benefit for patients and healthcare institutions. Preclinical testing of a drug in an animal model is not a prerequisite for regulatory agencies before entering clinical trials, but does unquestionably provide valuable data on the expected clinical performance of the drug. Hence, testing in animal models is largely recommended from both a business and patient perspective. In addition, inclusion of safety parameters in animal models will help to build the required safety data package of drugs in development (Denayer et al. *Translational Medicine.* 2: 5-11).

It is herein expressly contemplated that the compositions and methods of the instant disclosure can be applied to a number of model systems, to enable assessment of real-time transcriptome monitoring of living cells in their native environment across a time course, optionally in response to administration of agents including, e.g., lead drug compounds, screening compounds, etc. Such real-time/time course transcriptome information is contemplated to aid identification of drug impact upon oncogenesis, cell growth, toxicity and/or drug efficacy for any number of other uses, to the full extent that such real-time/time course transcriptome information can direct compound/lead agent selection, etc.

It is also expressly contemplated that, in certain embodiments, e.g., where the differences between a pathological transcriptome and a normal transcriptome are known, combinations of drugs (including small molecules, biologics, modified nucleic acids, DNA-targeting CRISPR-Cas systems, RNA-targeting CRISPR-Cas systems, TALENs, zinc finger nucleases) can be measured from a living animal to pair phenotype (and/or behavior) with the resulting transcriptome.

Expression Vector Promoters

An expression vector, otherwise known as an expression construct, is commonly a plasmid or virus designed for gene expression in cells. The vector is used to introduce a specific gene into a target cell, and can commandeer the cell's mechanism for protein synthesis to produce the protein encoded by the gene. Expression vectors are a basic tool in biotechnology for the production of proteins. The vector is engineered to contain regulatory sequences that act as enhancer and promoter regions and lead to efficient transcription of the gene carried on the expression vector. The promoters such as the CAG promoter, human synapsin (hSyn) promoter, and CaMKII promoter are used in mammalian expression vectors to drive gene expression.

CAG promoter is a strong synthetic promoter frequently used to drive high levels of gene expression in mammalian expression vectors. The CAG promoter consists of the Cytomegalovirus (CMV) early enhancer element, the first exon and the first intron of chicken beta-actin gene acting as the promoter, and a splice acceptor of the rabbit beta-globin gene.

By "CAG promoter" is meant a polynucleotide that is 95%, 96%, 97%, 98%, or 100% identical to (omitted).

By "CMV immediate early promoter" is meant a polynucleotide that is 95%, 96%, 97%, 98%, or 100% identical to (omitted).

By "hSyn promoter" is meant a polynucleotide that is 95%, 96%, 97%, 98%, or 100% identical to (omitted)

By "HSV thymidine kinase promoter" is meant a polynucleotide that is 95%, 96%, 97%, 98%, or 100% identical to (omitted).

By "early and late SV40 promoter" is meant a polynucleotide that is 95%, 96%, 97%, 98%, or 100% identical to (omitted).

By "CamKII promoter" is meant a polynucleotide that is 95%, 96%, 97%, 98%, or 100% identical to (omitted).

By "retroviral LTR promoter" is meant a polynucleotide that is 95%, 96%, 97%, 98%, or 100% identical to (omitted).

By "metallothionein I promoter" is meant a polynucleotide that is 95%, 96%, 97%, 98%, or 100% identical to (omitted).

Mammalian Cell Culture

In certain aspects, the instant disclosure describes methods and compositions designed to obtain VLP-encapsulated analyte data (e.g., real-time/time course transcriptome data) from living mammalian cells, optionally in cell culture. Mammalian cell culture is used widely in academic, medical and industrial settings. It has provided a means to study the physiology and biochemistry of the cell, and developments in the fields of cell and molecular biology have required the use of reproducible model systems, which cultured cell lines are especially capable of providing. For medical use, cell culture provides test systems to assess the efficacy and toxicology of potential new drugs. Large-scale mammalian cell culture has allowed production of biologically active proteins, initially production of vaccines and then recombinant proteins and monoclonal antibodies; meanwhile, recent innovative uses of cell culture include tissue engineering, as a means of generating tissue substitutes.

Mammalian cells can be isolated from tissues for ex vivo culture in several ways. Cells can be easily purified from blood. However, only the white cells are capable of growth in culture. Cells can be isolated from solid tissues by digesting the extracellular matrix using enzymes such as collagenase, trypsin, or pronase, before agitating the tissue to release the cells into suspension. Alternatively, pieces of tissue can be placed in growth media, and the cells that grow out are available for culture. This method is known as explant culture. Cells that are cultured directly from a subject are known as primary cells. With the exception of some derived from tumors, most primary cell cultures have limited lifespan (Voight et al. Journal of Molecular and Cellular Cardiology. 86: 187-98). An established or immortalized cell line has acquired the ability to proliferate indefinitely either through random mutation or deliberate modification, such as artificial expression of the telomerase gene. Numerous cell lines are well established as representative of particular cell types. Examples of commonly used mammalian cell lines include HEK293T cells, VERO, BHK, HeLa, CV1 (including Cos), MDCK, 293, 3T3, myeloma cell lines (e.g., NSO, NS 1), PC12, WI38 cells, and Chinese hamster ovary (CHO) cells, among many other examples (Langdon et al. Molecular Biomethods Handbook. 861-873).

Mammalian Cell Transfection Methods

Mammalian cell transfection is a technique commonly used to express exogenous DNA or RNA in a host cell line. There are many different methods available for transfecting mammalian cells, depending upon the cell line characteristics, desired effect, and downstream applications. These methods can be broadly divided into two categories: those used to generate transient transfection, and those used to generate stable transfectants. Transient transfection methods include, but are not limited to, liposome-mediated transfection, non-liposomal transfection agents (lipids and polymers), dendrimer-based transfection, and electroporation. Stable transfection methods include, but are not limited to microinjection, and virus-mediated gene delivery.

In certain aspects of the instant disclosure, stable transfection methods are used, e.g., to achieve integration of exogenous, viral/VLP-forming genes into a mammalian cell genome. Such stable transfection approaches tend to rely upon homologous recombination to achieve directed integration of exogenous nucleic acid sequences, and are well known in the art.

Certain aspects of the instant disclosure describe methods and compositions designed to achieve delivery of exogenous viral genes to mammalian cells. Viral vectors, such as bacteriophages, retrovirus, adenovirus (types 2 and 5), adeno-associated virus, herpes virus, pox virus, human foamy virus (HFV), and lentivirus have been used for gene transfection. Viral vector genomes can be modified by deleting some areas of their genomes so that their replication becomes altered, rendering such viruses safer than native forms. However, viral delivery systems have some problems, including: the marked immunogenicity of viruses, which can cause induction of the inflammatory system, potentially leading to degeneration of transducted tissue; and toxin production, including mortality, the insertional mutagenesis; and their limitation in transgenic capacity size. During the past few years some viral vectors with specific receptors have been designed that are capable of transferring transgenes to some other specific cells, which are not their natural target cells (retargeting) (Nayerossadat et al. Adv Biomed Res. 1:27).

Sequencing Methods

Some of the methods and compositions provided herein employ methods of sequencing nucleic acids. A number of DNA sequencing techniques are known in the art, including fluorescence-based sequencing methodologies (See, e.g., Birren et al, Genome Analysis Analyzing DNA, 1, Cold Spring Harbor, N.Y., which is incorporated herein by reference in its entirety). In some embodiments, automated sequencing techniques understood in that art are utilized. In some embodiments, parallel sequencing of partitioned amplicons can be utilized (PCT Publication No WO2006084132, which is incorporated herein by reference in its entirety). In some embodiments, DNA sequencing is achieved by parallel oligonucleotide extension (See, e.g., U.S. Pat. Nos. 5,750,341; 6,306,597, which are incorporated herein by reference in their entireties). Additional examples of sequencing techniques include the Church polony technology (Mitra et al, 2003, Analytical Biochemistry 320, 55-65; Shendure et al, 2005 Science 309, 1728-1732; U.S. Pat. Nos. 6,432,360, 6,485,944, 6,511,803, which are incorporated by reference), the 454 picotiter pyrosequencing technology (Margulies et al, 2005 Nature 437, 376-380; US 20050130173, which are incorporated herein by reference in their entireties), the Solexa single base addition technology (Bennett et al, 2005, Pharmacogenomics, 6, 373-382; U.S. Pat. Nos. 6,787,308; 6,833,246, which are incorporated herein by reference in their entireties), the Lynx massively parallel signature sequencing technology (Brenner et al. (2000). Nat. Biotechnol. 18:630-634; U.S. Pat. Nos. 5,695, 934; 5,714,330, which are incorporated herein by reference in their entireties), and the Adessi PCR colony technology (Adessi et al. (2000). Nucleic Acid Res. 28, E87; WO 00018957, which are incorporated herein by reference in their entireties).

Next-generation sequencing (NGS) methods can be employed in certain aspects of the instant disclosure to obtain a high volume of sequence information (such as are particularly required to perform deep sequencing VLPs following capture) in a highly efficient and cost effective manner. NGS methods share the common feature of massively parallel, high-throughput strategies, with the goal of lower costs in comparison to older sequencing methods (see, e.g., Voelkerding et al, Clinical Chem., 55: 641-658, 2009; MacLean et al, Nature Rev. Microbiol, 7-287-296; which are incorporated herein by reference in their entireties). NGS methods can be broadly divided into those that typically use template amplification and those that do not. Amplification-utilizing methods include pyrosequencing commercialized by Roche as the 454 technology platforms (e.g., GS 20 and GS FLX), the Solexa platform commercialized by Illumina®, and the Supported Oligonucleotide Ligation and Detection (SOLiD™) platform commercialized by Applied Biosystems®. Non-amplification approaches, also known as single-molecule sequencing, are exemplified by the HeliScope platform commercialized by Helicos Biosciences, SMRT sequencing commercialized by Pacific Biosciences, and emerging platforms marketed by VisiGen and Oxford Nanopore Technologies Ltd.

In pyrosequencing (U.S. Pat. Nos. 6,210,891; 6,258,568, which are incorporated herein by reference in their entireties), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al, Clinical Chem., 55-641-658, 2009; MacLean et al, Nature Rev. Microbiol, 7:287-296; U.S. Pat. Nos. 6,833,246; 7,115,400; 6,969,488, which are incorporated herein by reference in their entireties), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluorophore and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al, Clinical Chem., 55: 641-658, 2009; U.S. Pat. Nos. 5,912,148; and 6,130,073, which are incorporated herein by reference in their entireties) can initially involve fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing is employed (see, e.g., Astier et al, J. Am. Chem. Soc. 2006 Feb. 8; 128(5): 1705-10, which is incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore (or as individual nucleotides pass through the nanopore in the case of exonuclease-based techniques), this causes a change in the magnitude of the current through the nanopore that is distinct for each of the four bases, thereby allowing the sequence of the DNA molecule to be determined.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, which are incorporated herein by reference in their entireties). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is approximately 99.6% for 50 base reads, with approximately 100 Mb generated per run. The read-length is 100 base pairs. The accuracy for homopolymer repeats of 5 repeats in length is approximately 98%. The benefits of ion semiconductor sequencing are rapid sequencing speed and low upfront and operating costs.

Therapeutic Delivery of Nucleic Acid Constructs

Certain aspects of the instant disclosure provide for delivery of nucleic acid constructs, including those described herein, to the brain of a subject. While delivery of nucleic acid constructs to the central nervous system (CNS) poses particular problems due to the blood brain barrier (BBB) that free nucleic acid constructs cannot cross, it is contemplated that delivery to the CNS of a subject can be performed by a variety of art-recognized routes including, without limitation, intracranial and/or intrathecal injection, cisterna *magna* injection, and injection to the striatum of a subject. By intrathecal administration of the nucleic acid construct, a therapeutic method of the instant disclosure can introduce a therapeutic nucleic acid construct (e.g., one harboring a SFO) into a brain or spine tissue of a subject, for instance, cortex, cerebellum, cervical spine, lumbar spine, and/or thoracic spine.

Delivery reagents such as liposomes, cationic lipids, and nanoparticles forming complexes (e.g., lipid nanoparticles (LNPs)) can also be used to aid the intracellular internalization of nucleic acid constructs into cells of neuronal origin. Exemplary LNPs and other lipid-based delivery vehicles are described further below and are known in the art.

In addition to direct introduction to the CNS of a subject, it is also contemplated that the nucleic acid constructs of the instant disclosure can be directed to the CNS following administration via intravenous (IV) injection or other parenteral route of administration.

In embodiments, the constructs of the instant disclosure can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g. a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific expression, the expression of a nucleic acid construct can be driven by a cell-type specific promoter. For example, neuron-specific expression (e.g. for targeting CNS disorders) might use the Synapsin I promoter.

For in vivo delivery, AAV has been recognized as advantageous over other viral vectors for a number of reasons, including low toxicity (this may be due to the purification method not requiring ultracentrifugation of cell particles that can activate the immune response); and low probability of causing insertional mutagenesis because it doesn't integrate into the host genome.

Traditional forms of AAV have a packaging limit of 4.5 or 4.75 Kb. Constructs larger than 4.5 or 4.75 Kb can lead to significantly reduced virus production.

The AAV employed can be, without limitation, AAV1, AAV2, AAV5 or any combination thereof. One can select the AAV of the AAV with regard to the cells to be targeted; e.g., one can select AAV serotypes 1, 2, 5 or a hybrid capsid AAV1, AAV2, AAV5 or any combination thereof for targeting brain or neuronal cells. Certain recombinant AAVs (rAAVs) possessing engineered specificity are known in the art and can be employed. A number of rAAVs include variants with tropisms having an increased specificity and transduction efficiency when measured in the CNS, and in some cases, a decreased specificity and transduction efficiency in an off-target environment, like the liver (see, e.g., WO 2020/210655).

Lentiviral vectors are also expressly contemplated for use with the nucleic acid constructs of the instant disclosure. Lentiviruses have been disclosed in the art as delivery vehicles for the treatment of Parkinson's Disease (see, e.g., US Patent Publication No. 20120295960 and U.S. Pat. Nos. 7,303,910 and 7,351,585). Lentiviral vectors have also been disclosed for delivery to the brain, see, e.g., US Patent Publication Nos. US20110293571; US20110293571, US20040013648, US20070025970, US20090111106 and U.S. Pat. No. 7,259,015.

In some embodiments, delivery can be performed by encapsulation of a nucleic acid construct of the instant disclosure in a lipid particle such as a lipid nanoparticle (LNP). In certain embodiments, therefore, lipid nanoparticles (LNPs) are contemplated. An antitransthyretin small interfering RNA was previously described as encapsulated in lipid nanoparticles and delivered to humans (see, e.g., Coelho et al., N Engl J Med 2013; 369:819-29), and such a system may be adapted and applied to the SFO nucleic acid constructs of the present disclosure. Doses of about 0.01 to about 1 mg per kg of body weight administered intravenously are contemplated. Medications to reduce the risk of infusion-related reactions are contemplated, such as dexamethasone, acetampinophen, diphenhydramine or cetirizine, and ranitidine are contemplated. Multiple doses of about 0.3 mg per kilogram every 4 weeks for five doses are also contemplated.

In some embodiments, the LNP for delivering a nucleic acid construct of the disclosure is prepared by methods known in the art, such as those described in, for example, WO 2005/105152 (PCT/EP2005/004920), WO 2006/069782 (PCT/EP2005/014074), WO 2007/121947 (PCT/EP2007/003496), and WO 2015/082080 (PCT/EP2014/003274), which are herein incorporated by reference. LNPs aimed specifically at the enhanced and improved delivery of nucleic acids into mammalian cells are described in, for example, Aleku et al., Cancer Res., 68(23): 9788-98 (Dec. 1, 2008), Strumberg et al., Int. J. Clin. Pharmacol. Ther., 50(1): 76-8 (January 2012), Schultheis et al., J. Clin. Oncol., 32(36): 4141-48 (Dec. 20, 2014), and Fehring et al., Mol. Ther., 22(4): 811-20 (Apr. 22, 2014), which are herein incorporated by reference and may be applied to the present technology.

In some embodiments, the LNP includes any LNP disclosed in WO 2005/105152 (PCT/EP2005/004920), WO 2006/069782 (PCT/EP2005/014074), WO 2007/121947 (PCT/EP2007/003496), and WO 2015/082080 (PCT/EP2014/003274).

Exosomes are endogenous nano-vesicles that transport nucleic acids and proteins, and which can deliver nucleic acids to the brain and other target organs. To reduce immunogenicity, Alvarez-Erviti et al. (2011, Nat Biotechnol 29:341) used self-derived dendritic cells for exosome production. Targeting to the brain was achieved by engineering the dendritic cells to express Lamp2b, an exosomal membrane protein, fused to the neuron-specific RVG peptide. It is contemplated that exosomes may also be employed to deliver the nucleic acid constructs of the instant disclosure, e.g., specifically to neurons, microglia, and/or oligodendrocytes in the brain, resulting in therapeutic effect.

El-Andaloussi et al. (Nature Protocols 7: 2112-2126 (2012)) also discloses how exosomes derived from cultured cells can be harnessed for delivery of nucleic acids in vitro and in vivo. Plasma exosomes as described, e.g., in Wahlgren et al. (Nucleic Acids Research, 2012, Vol. 40, No. 17 e130) are also contemplated.

Delivery or administration according to the instant disclosure can also be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, nontoxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

In certain embodiments, Trojan Horse liposomes (also known as Molecular Trojan Horses) are desirable and protocols may be found at cshprotocols.cshlp.org/content/2010/4/pdb.prot5407.long. These particles allow delivery of a transgene to the entire brain after an intravascular injection. Without being bound by theory, it is believed that neutral lipid particles with specific antibodies conjugated to surface allow crossing of the blood brain barrier via endocytosis. Trojan Horse Liposomes may be used to deliver a nucleic acid construct as disclosed herein to the brain via an intravascular injection, thereby allowing for whole brain transgenic animals/subjects without the need for embryonic manipulation.

Nucleic acid constructs of the instant disclosure may be administered in liposomes, such as a stable nucleic-acid-lipid particle (SNALP) (see, e.g., Morrissey et al., Nature Biotechnology, Vol. 23, No. 8, August 2005). Also refer, e.g., to US 2020/00332272, which contemplates delivery of CRISPR machinery, and is also contemplated for use with the SFO nucleic acid constructs of the instant disclosure.

Certain aspects of the instant disclosure relate to a method of treating a subject having a CNS disorder (e.g., Parkinson's Disease), comprising administering to the subject a nucleic acid construct of the disclosure, and then exposing the subject to a therapeutically effective amount of light of a proper wavelength to excite and/or inhibit a construct-expressed SFO in the subject, thereby treating the subject. Exemplary CNS disorders that can be treated by the method of the disclosure include Parkinson's Disease (PD), Alzheimer's disease (AD), amyotrophic lateral schlerosis (ALS), frontotemporal dementia, huntington, spinocerebellar, prion, and lafora.

Compositions for intrathecal, intraventricular, intravenous or other forms of administration may include sterile aqueous solutions which may also contain buffers, diluents and other suitable additives. Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes may be controlled to render the preparation isotonic.

In certain embodiments, the nucleic acid construct is delivered by intrathecal injection (i.e. injection into the spinal fluid which bathes the brain and spinal cord tissue). Intrathecal injection of nucleic acid constructs into the spinal fluid can be performed as a bolus injection or via minipumps which can be implanted beneath the skin, providing a regular and constant delivery of nucleic acid construct into the spinal fluid. The circulation of the spinal fluid from the choroid plexus, where it is produced, down around the spinal cord and dorsal root ganglia and subsequently up past the cerebellum and over the cortex to the arachnoid granulations, where the fluid can exit the CNS, that, depending upon size, stability, and solubility of the constructs and/or optional delivery vehicles (e.g., AAV, LNP, etc.) injected, constructs delivered intrathecally could hit target cells throughout the entire CNS.

In some embodiments, the intrathecal administration is via a pump. The pump may be a surgically implanted osmotic pump. In one embodiment, the osmotic pump is implanted into the subarachnoid space of the spinal canal to facilitate intrathecal administration.

In some embodiments, the intrathecal administration is via an intrathecal delivery system for a pharmaceutical including a reservoir containing a volume of the pharmaceutical agent, and a pump configured to deliver a portion of the pharmaceutical agent contained in the reservoir. More details about this intrathecal delivery system may be found in PCT/US2015/013253, which is incorporated by reference in its entirety.

Kits

The instant disclosure also provides kits containing compositions of the instant disclosure, e.g., for use in methods of the present disclosure. Kits of the instant disclosure may include one or more containers comprising a composition (e.g., a nucleic acid encoding for a light sensitive polypeptide such as SOUL) of this disclosure. In some embodiments, the kits further include instructions for use in accordance with the methods of this disclosure. In some embodiments, these instructions comprise a description of administration/transfection of the composition(s) to mammalian cells.

Instructions supplied in the kits of the instant disclosure are typically written instructions on a label or package insert (e.g., a paper sheet included in the kit), but machine-readable instructions (e.g., instructions carried on a magnetic or optical storage disk) are also acceptable. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. The container may further comprise a mammalian cell transfection agent.

Kits may optionally provide additional components such as buffers and interpretive information. Normally, the kit comprises a container and a label or package insert(s) on or associated with the container.

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims. Standard techniques well known in the art or the techniques specifically described below were utilized.

EXAMPLES

Figure 1B:
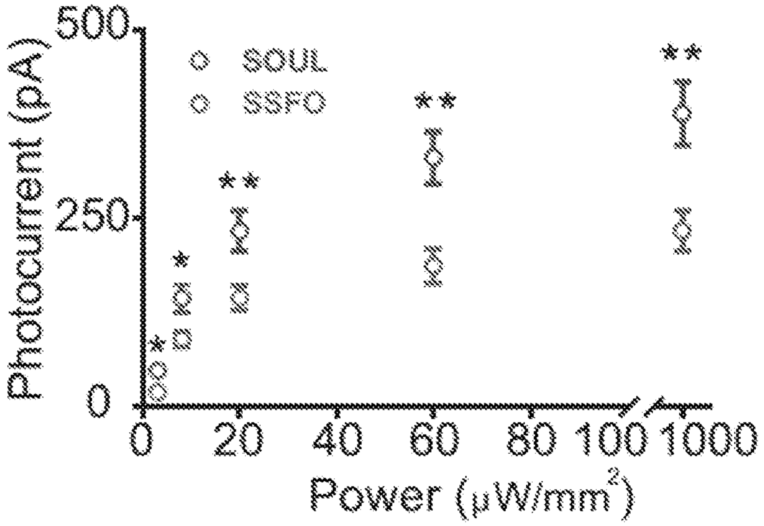
Figure 1C:
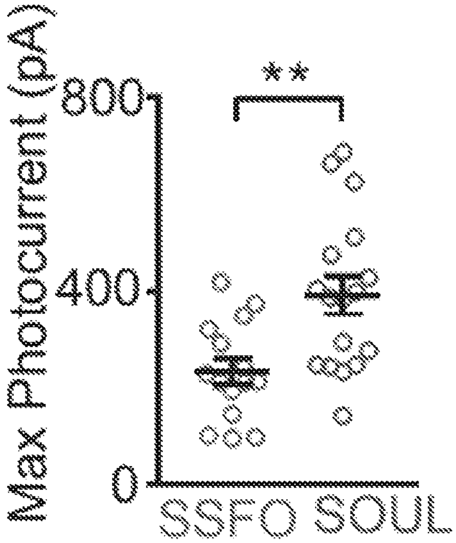

Example 1: Development and Validation of a Cre-Inducible SOUL Knock-In Mouse Line One family of opsins known to possess high light sensitivity, due to their slow off kinetics, is the step-function opsins (SFOs). Therefore, the SFO family was chosen as a parental base and SOUL, a variant with enhanced operational light sensitivity, was created. To create SOUL, the stabilized step-function opsin (SSFO) mutations C128S and D156A (Selimbeyoglu et al., 2017; Yizhar et al., 2011b), known to slow the photocycle kinetics, were combined with the T159C mutation (Berndt et al., 2011; Ullrich et al., 2013), which dramatically increases photocurrents in channelrhodopsin-2 and thus imparts a higher operational light sensitivity (Mattis et al., 2011). The enhanced photocurrent properties of the new opsin were tested compared to the parental opsin SSFO by expressing both opsins in primary cultures of mouse hippocampal neurons and performing whole-cell patch-clamp recordings. It was found that SOUL-expressing neurons had a significantly higher operational light sensitivity compared to SSFO (FIGS. 1A and 1B) and a peak photocurrent amplitude of 391.36±38.88 pA, which was almost double that of SSFO-expressing neurons at 233.66±26.14 pA (FIG. 1C). It was also discovered that the expression of SOUL channels does not affect the basic electrical properties of neurons (FIG. 8).

Figure 9A:
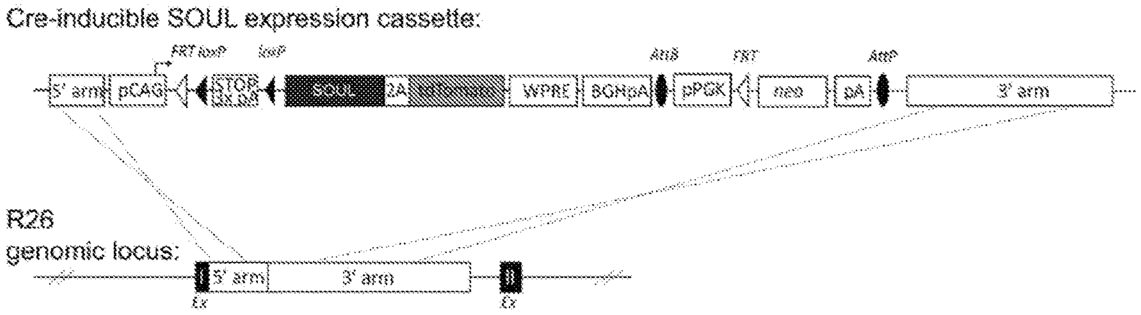
FIGS. 9A and 9B present schematics representing generation of SOUL knock-in mice according to exemplary embodiments of the disclosure.
Figure 9B:
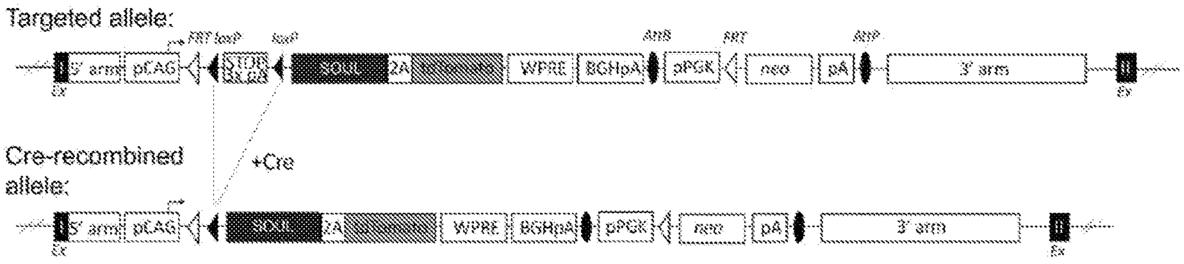
Figure 10A:
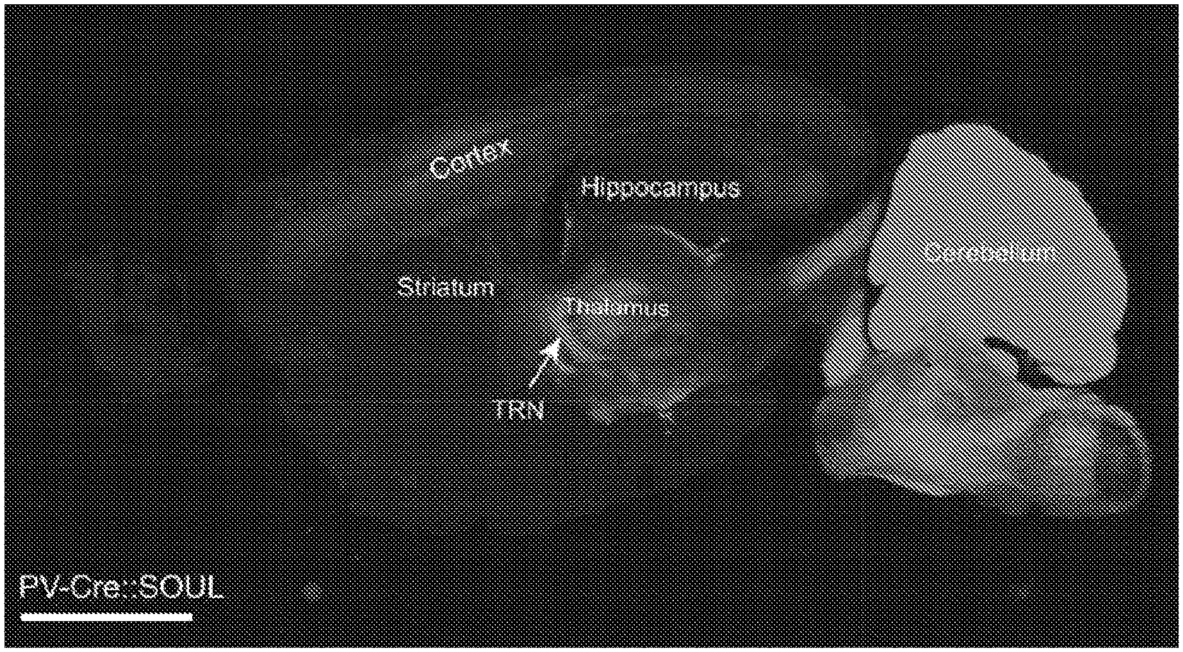
FIGS. 10A and 10B show brain section images from Cre crosses of SOUL knock-in mice according to exemplary embodiments of the disclosure.
Figure 10B:
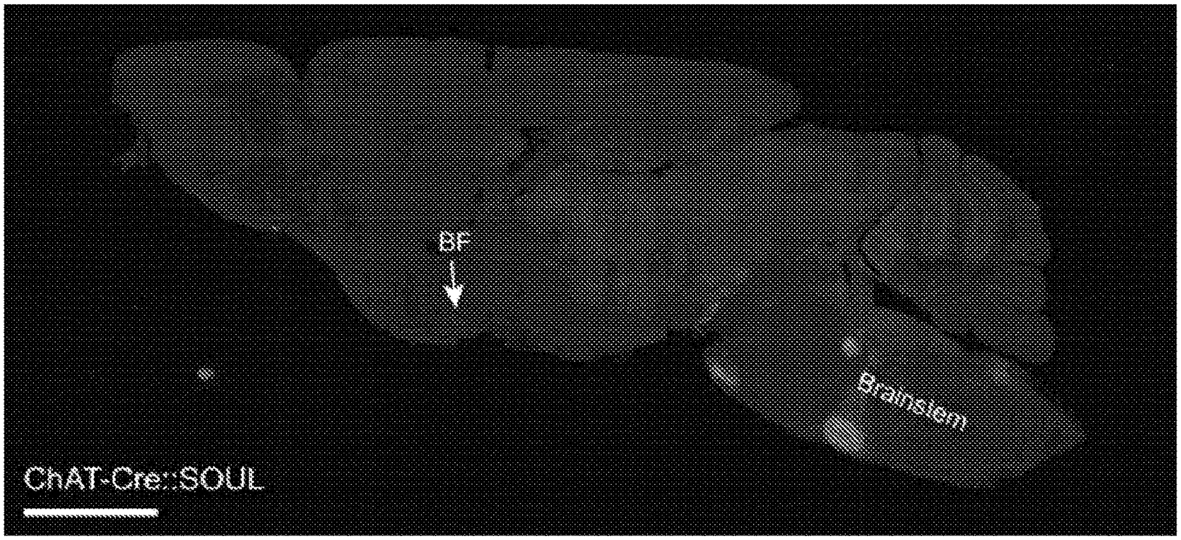
Figure 11A:
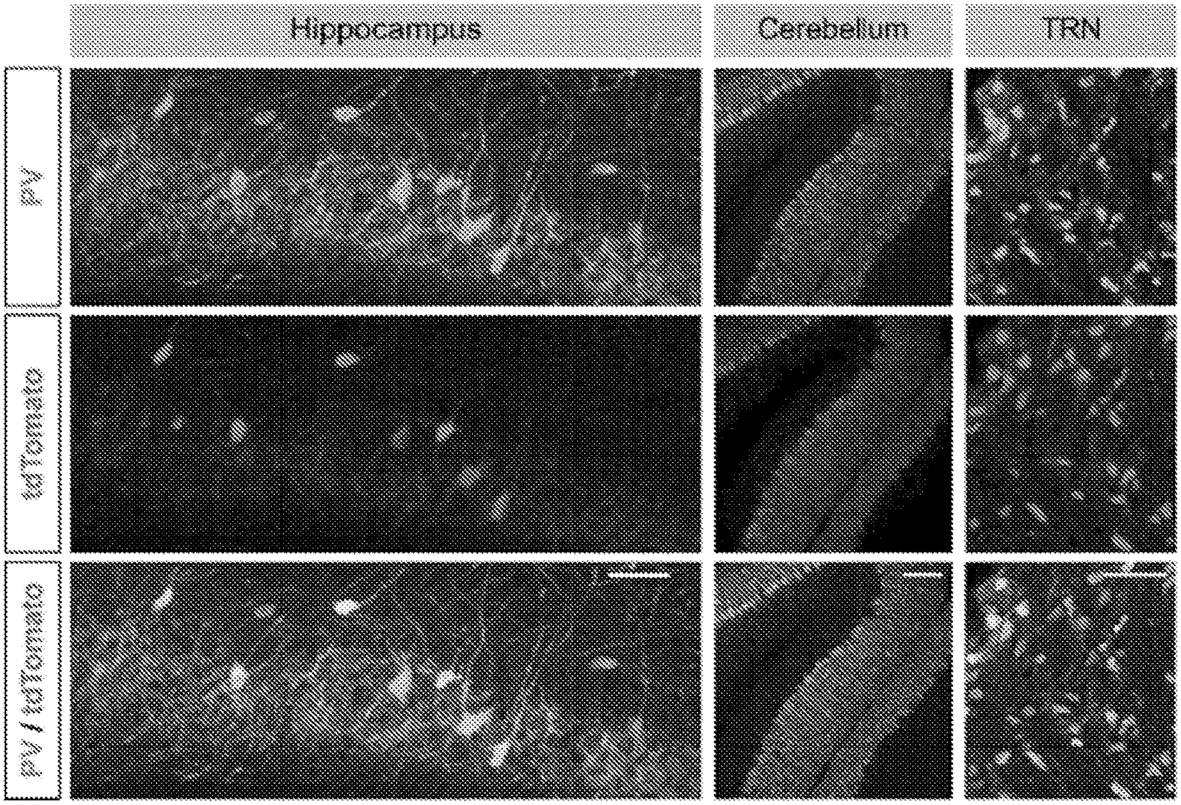
FIGS. 11A to 11C present images of Cre-induced transgene expression in PV-Cre:SOUL mice and ChAT-Cre: SOUL mice according to exemplary embodiments of the disclosure.
Figure 11B:
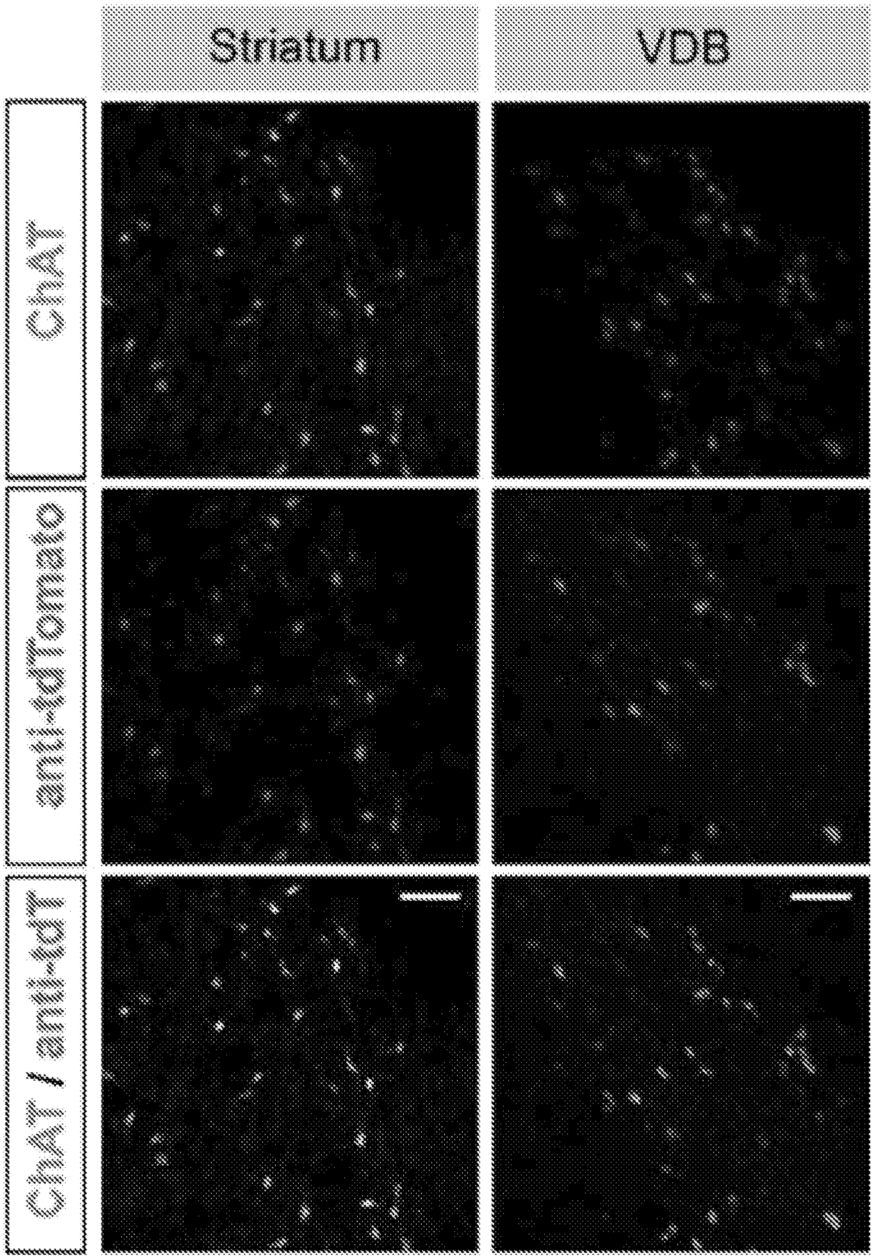

Next, a Cre-inducible SOUL-P2A-tdTomato knock-in mouse line that enables targeted, cell type-specific expression of SOUL was created. The Cre-inducible SOUL expression is under the control of the CAG promoter and the target cassette was inserted into the endogenous Rosa26 locus (FIG. 9A). Expression of Cre recombinase leads to the excision of the floxed-STOP cassette and subsequent expression of SOUL and tdTomato fluorescence (FIG. 9B). To test the Cre-dependent expression of the SOUL knock-in line, the knock-in line was crossed with the parvalbumin (PV)-IRES-Cre and ChAT-Cre driver mouse lines. Both PV-Cre:SOUL mice and ChAT-Cre:SOUL mice displayed robust tdTomato fluorescence that was consistent with the expected recombination patterns for these Cre mouse lines (Hippenmeyer et al., 2005; Rossi et al., 2011; Zhao et al., 2011). PV-Cre:SOUL mice showed strong native fluorescence throughout the brain, including the cortex, globus pallidus, thalamic reticular nucleus, striatum, hippocampus and cerebellum (FIG. 10A); while ChAT-Cre:SOUL mice exhibited tdTomato fluorescence in various brain areas including the basal forebrain, striatum, and brainstem nuclei (FIG. 10B). To further examine the fidelity and completeness of expression in specific neuronal cell types, the expression patterns of tdTomato were compared with endogenous cell type markers using immunostaining with antibodies and found that tdTomato was selectively expressed in the targeted neuronal populations (FIGS. 11A and 11B; Table 1).

TABLE 1

Co-localization of tdTomato and cell markers (PV or ChAT) in PV-Cre:SOUL and ChAT-Cre:SOUL mice.

| PV-Cre:SOUL | | |
|---|---|---|
| Brain Region | Completeness ($tdT^+PV^+/PV^+$)[a] | Fidelity ($tdT^+PV^+/tdT^+$)[a] |
| Cerebellum | 94% | 99% |
| Hippocampus | 73% | 98% |
| TRN | 95% | 94% |
| **ChAT-Cre::SOUL** | | |
| Brain Region | Completeness ($tdT^+ChAT^+/ChAT^+$) | Fidelity ($tdT^+ChAT^+/tdT^+$) |
| CPu | 94% | 99% |

Note:
[a] $tdT^+PV^+/PV^+$ = number (%) of PV staining positive cells that are also SOUL-P2AtdTomato positive;
$tdT^+PV^+/tdT^+$ = number (%) of SOUL-P2A-tdTomato positive cells that are also PV staining positive.
The same definition is used for all lines and columns.
PV: parvalbumin;
ChAT choline acetyltransferase;
TRN: Thalamic reticular nucleus;
CPu: caudate putamen.

Figure 11C:
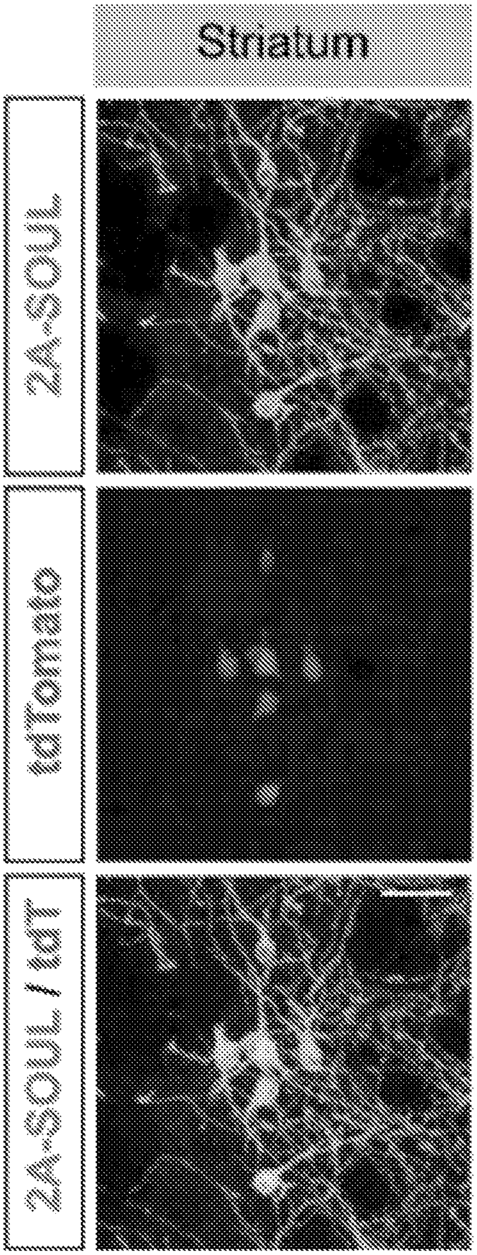

Furthermore, while the cytoplasmic tdTomato fluorescence facilitated visualization of SOUL expressing neurons (FIG. 11C), the P2A-mediated self-cleavage physically uncoupled tdTomato from SOUL (Kim et al., 2011) (as identified by the 2A fragment remaining at the SOUL C-terminus, FIG. 11C), and thus prevented the possible interference of the fluorophore with the opsin's function (Madisen et al., 2012).

Figure 2A:
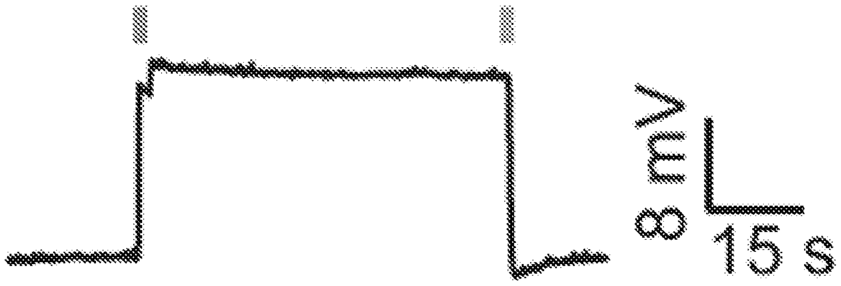
FIG. 2A shows a representative voltage trace over time for a SOUL-expressing PV+ neuron in acute brain slices upon blue-light activation (blue bar) and orange-light deactivation (orange bar). Scale bars: 8 mV and 15 s.
Figure 2B:
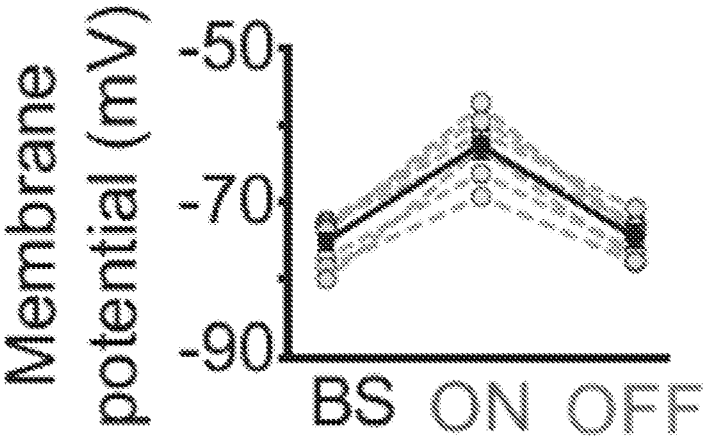
FIG. 2B depicts membrane potentials of individual neurons' (dashed lines) mean (±SEM, solid line) during baseline (BS), upon blue light activation (ON) and orange light deactivation (OFF).
Figure 2C:
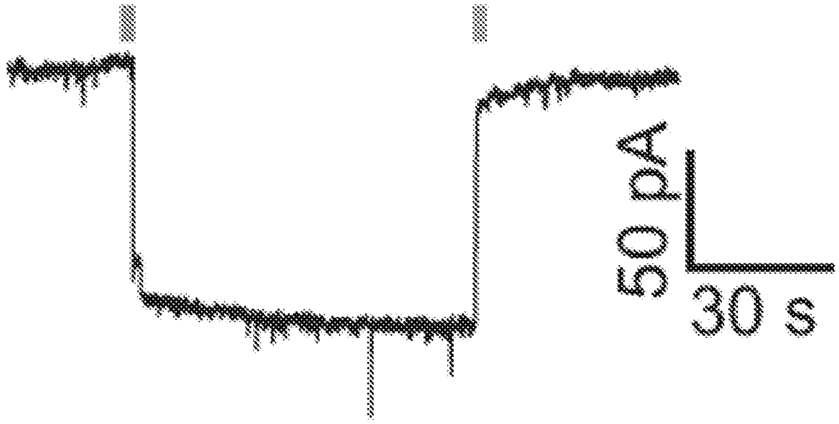
FIG. 2C shows a representative current trace over time for a SOUL-expressing PV neuron upon blue-light activation (blue bar) and orange-light deactivation (orange bar). Scale bars: 50 pA and 30s.
Figure 2D:
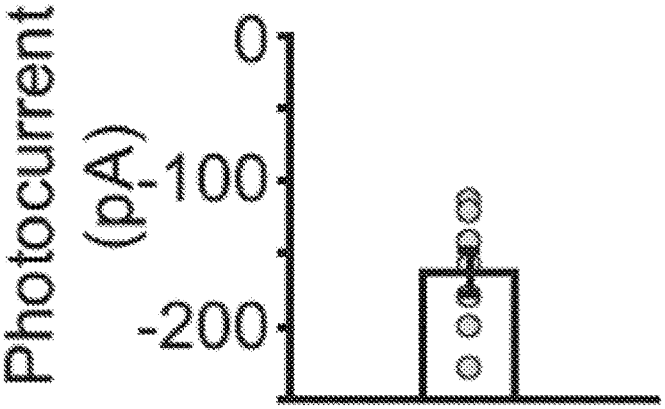
FIG. 2D shows a graph presenting photocurrents of individual neurons (dots) and mean (±SEM, solid line).
Figure 2E:
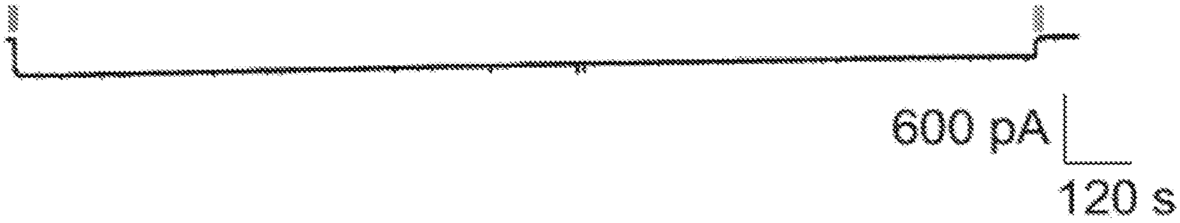
FIG. 2E shows a representative current trace over time for a SOUL-expressing D1 neuron upon SOUL activation (blue bar) and deactivation (orange bar).
Figure 2F:
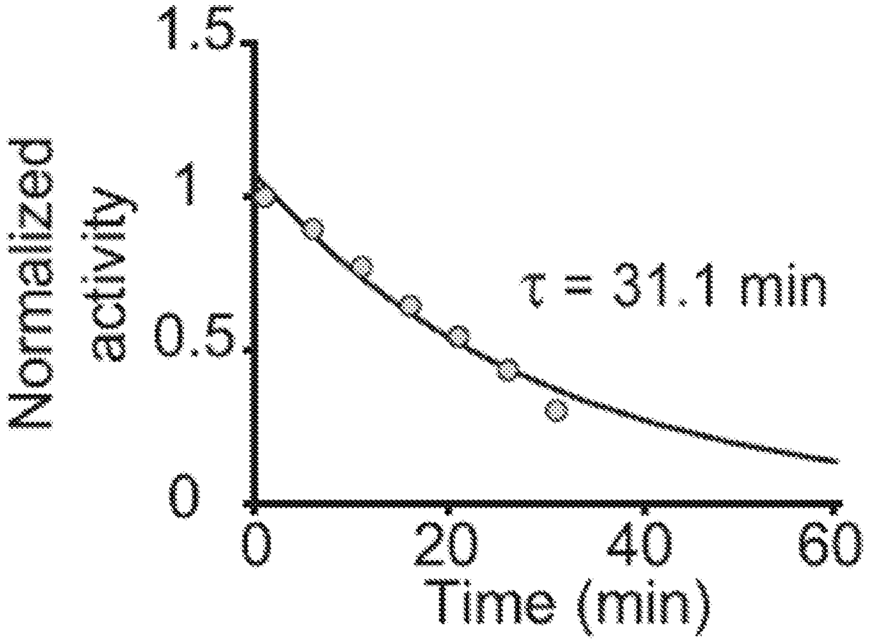
FIG. 2F presents peak current-normalized activity of SOUL over time with a mono-exponential fit (solid line; $\tau=31.1$ min).

To test the ability to optically activate and deactivate SOUL in this mouse line, whole-cell recordings were performed in acute brain slices of SOUL:PV-IRES-Cre mice. Parvalbumin-expressing neurons in the dorsolateral striatum were identified by tdTomato fluorescence. In SOUL-expressing PV neurons, the membrane was depolarized with a brief (2 seconds) blue light pulse and brought back to the resting potential with an equivalent pulse of orange light illumination (FIGS. 2A and 2B). Exposure to blue light initiated a robust photocurrent, and this photocurrent was readily terminated by the orange light (FIGS. 2C and 2D), demonstrating that SOUL is capable of causing a robust and reversible increase in neuronal activity in transgenic mice. In addition, step function opsins are distinguished by their prolonged open state; whole-cell recordings were therefore performed in SOUL-expressing D1 neurons in SOUL: Drdla-Cre mouse brain slices and confirmed that SOUL retains a prolonged open state (deactivation time constant r=31.1 min) which is the hallmark of SFOs (FIGS. 2E and 2F). Thus, SOUL was expressed in a Cre-dependent manner and functions robustly in SOUL knock-in mice, demonstrating that this line may be used to manipulate activity of various types of neurons.

Example 2: Noninvasive Transcranial Activation of SOUL in Mice

As mentioned above, while activation of neurons in vivo using non-invasive transcranial optogenetic stimulation has many advantages, one major challenge is that it requires light to penetrate through various tissues such as skull bone, gray and white matter, and blood vessels, which significantly attenuates light power density due to light scattering and absorption. As a result, the light power reaching the target brain regions is only a small fraction of the source power, making it difficult for opsins to be activated. However, it was reasoned that such low light power may be sufficient to activate SOUL, given its high photosensitivity.

Figure 3A:
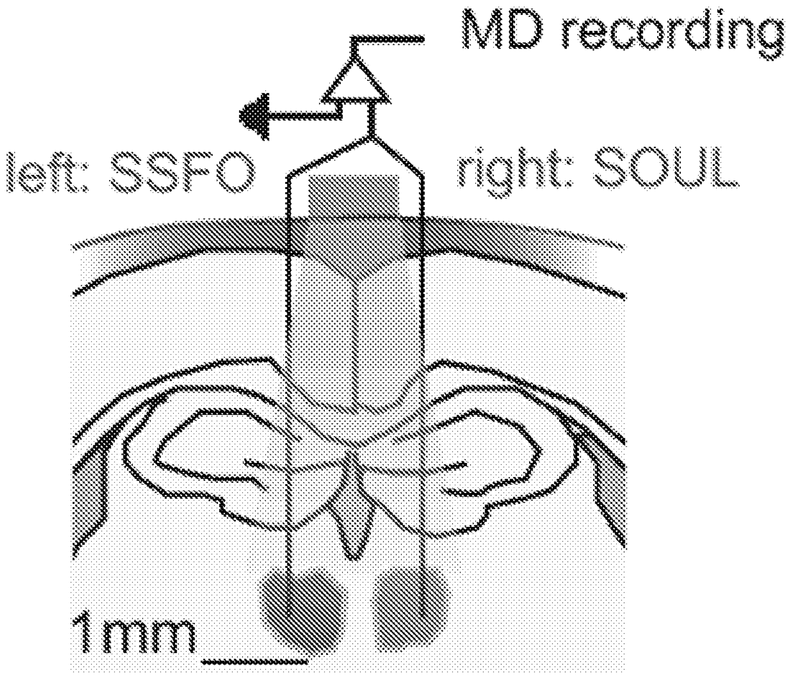
FIGS. 3A to 3H shows schematics, plots, graphs, and images, respectively, representing non-invasive transcranial stimulation of SOUL and SSFO in vivo according to exemplary embodiments of the disclosure.
Figure 3B:
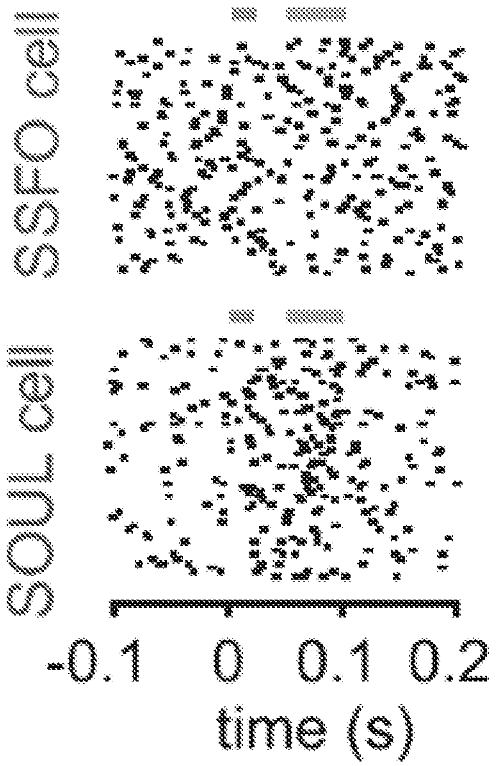
Figure 3C:
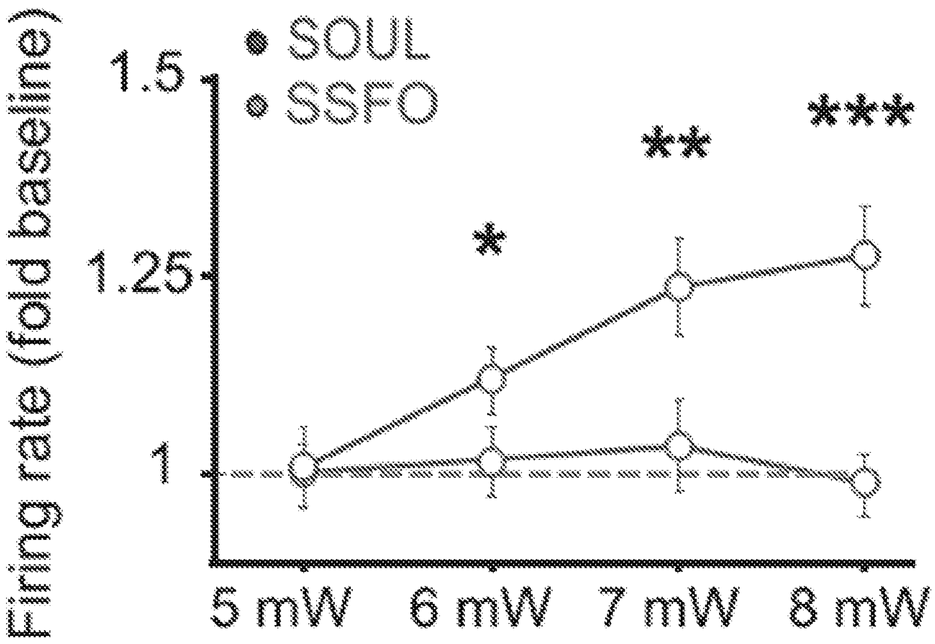
Figure 3D:
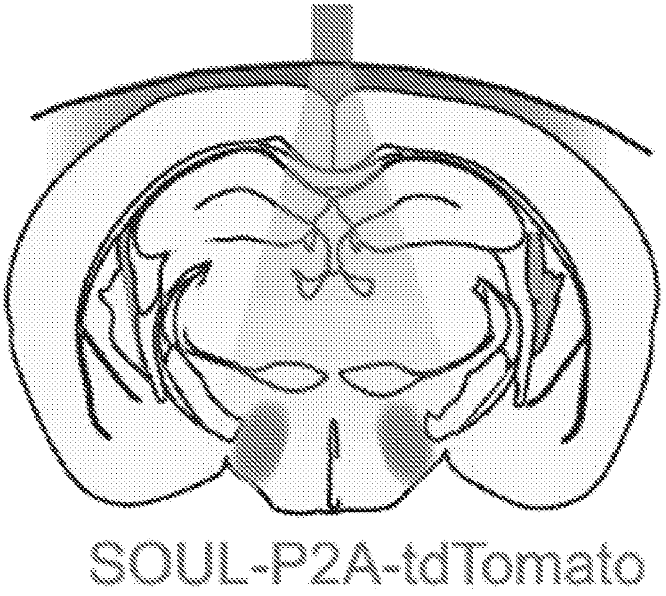
Figure 3E:
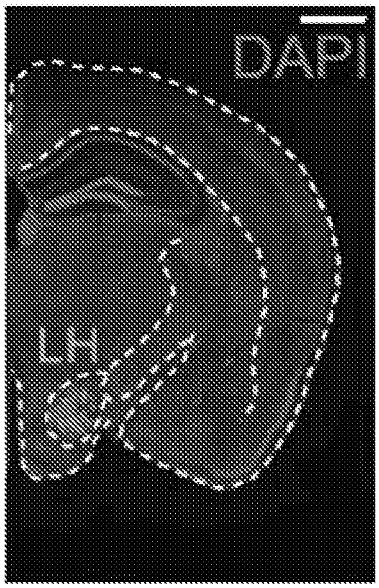
Figure 3F:
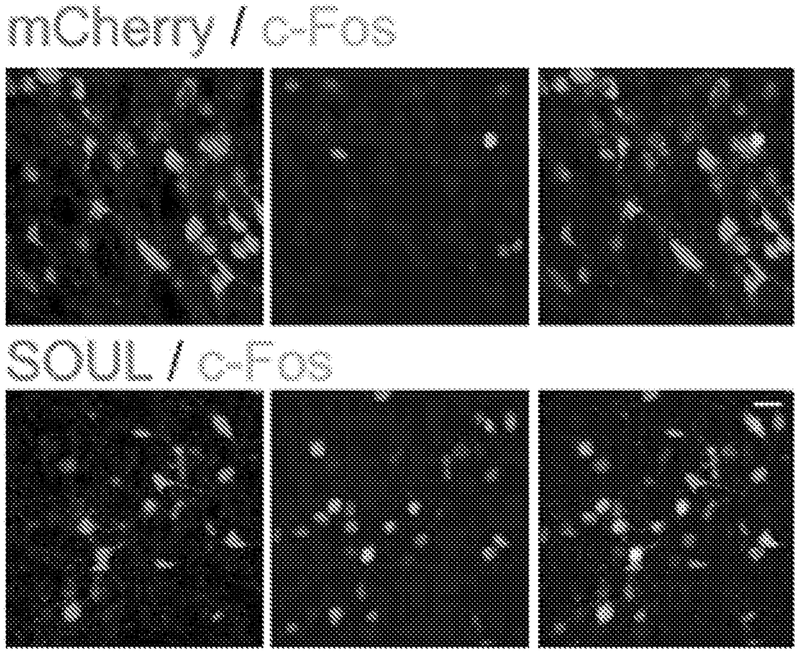
Figure 3G:
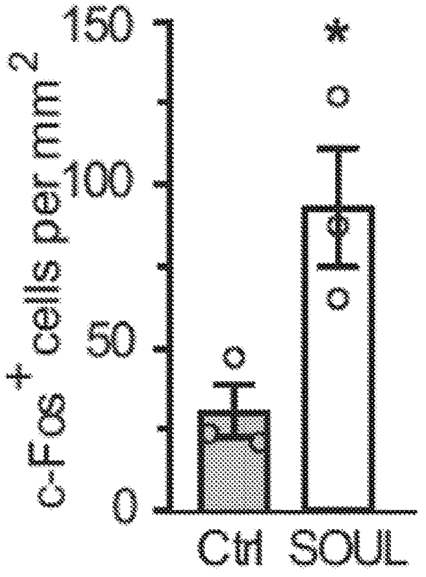
Figure 3H:
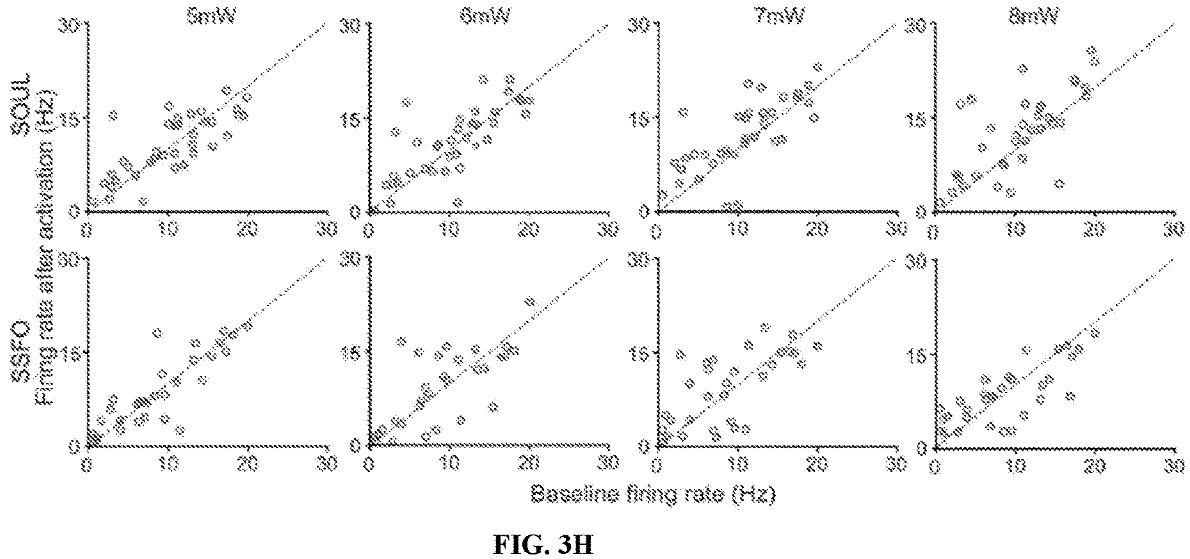
Figure 12A:
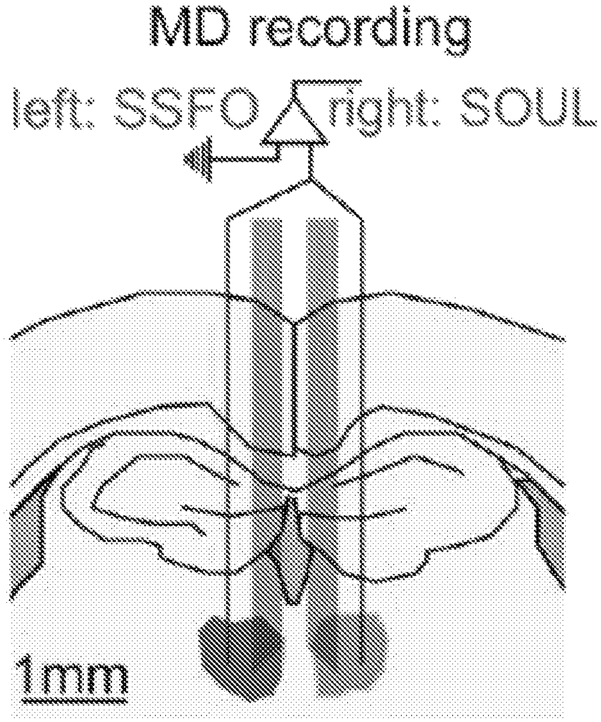
FIGS. 12A to 12C show a schematic, and graphs representing intracranial stimulation of SOUL and SSFO in vivo according to exemplary embodiments of the disclosure.
Figure 12B:
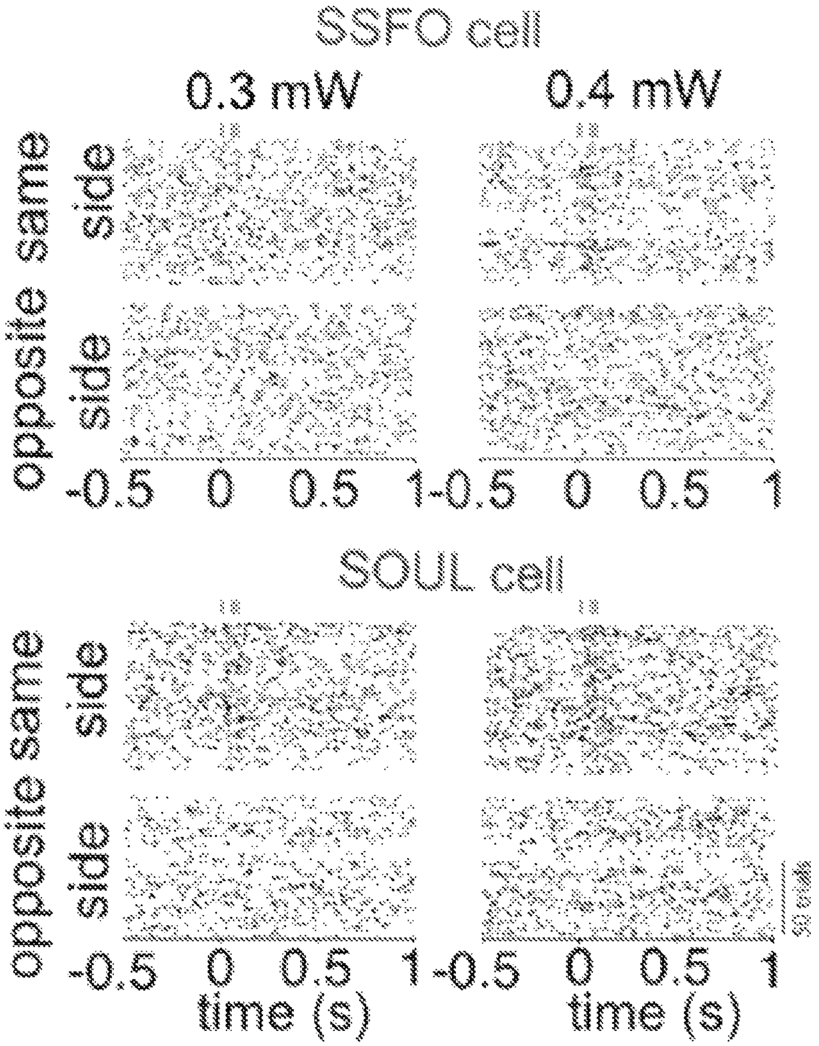
Figure 12C:
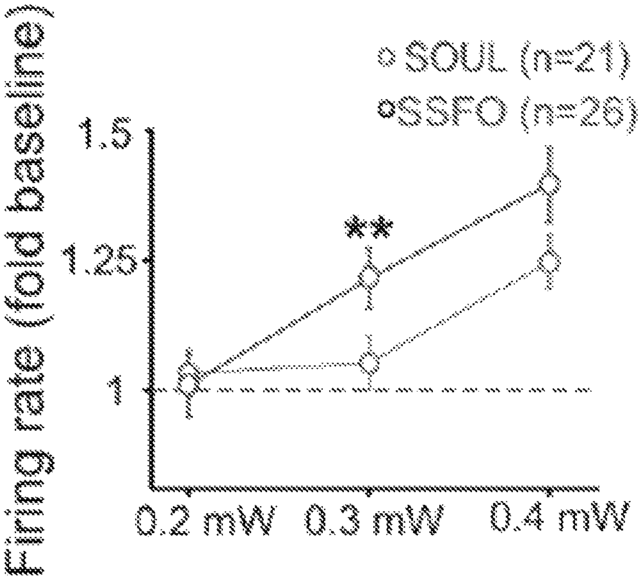
Figure 13A:
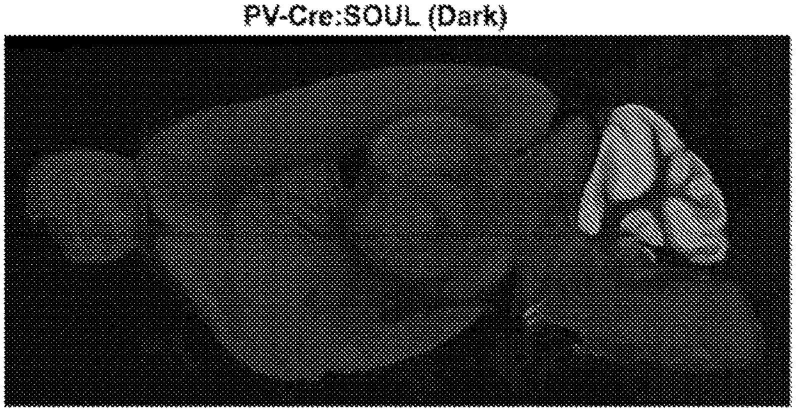
FIGS. 13A to 13D present images depicting the expression of c-fos protein in the brains of PV-Cre:SOUL mice in the dark and under laboratory ambient light according to exemplary embodiments of the disclosure.
Figure 13B:
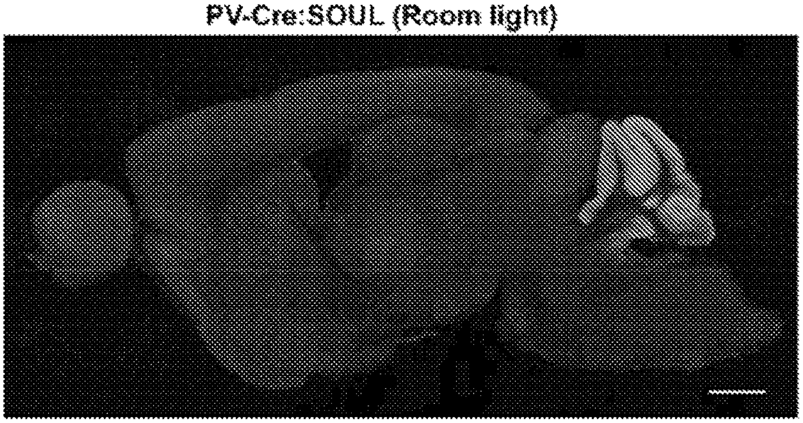
Figure 13C:
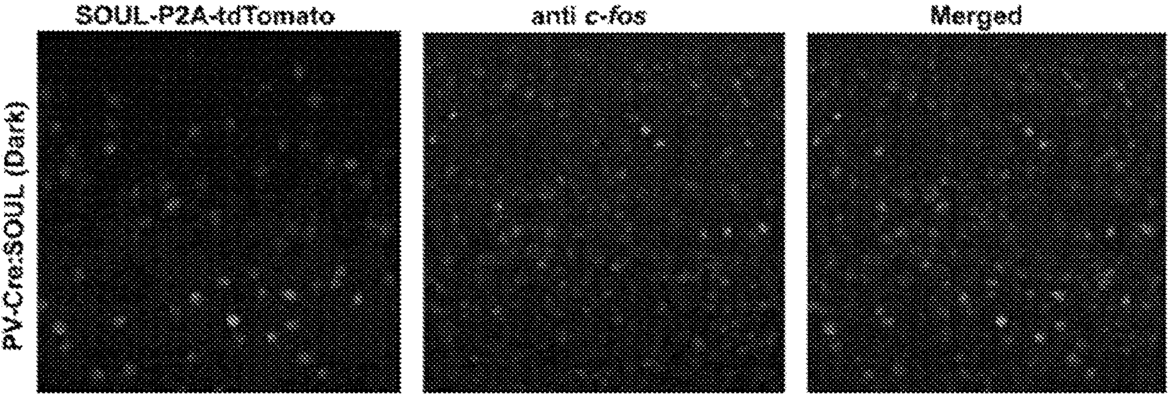
Figure 13D:
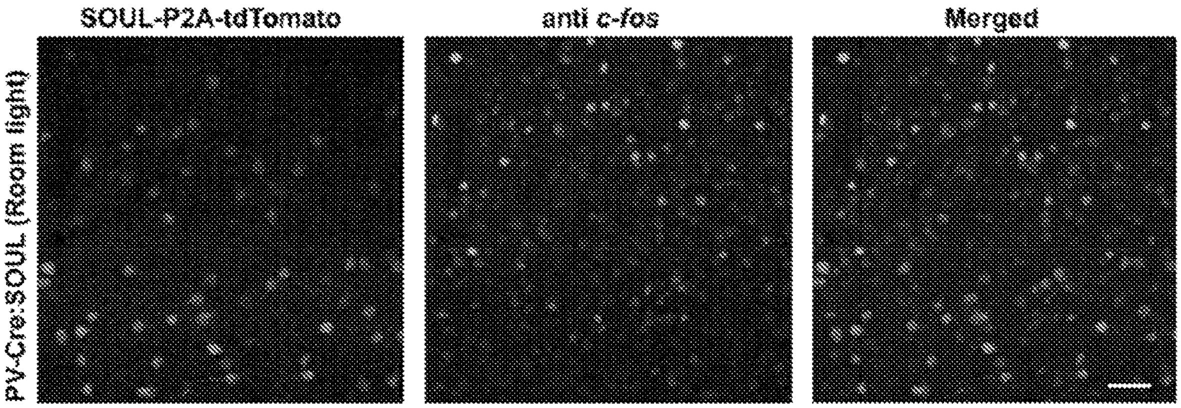
Figure 14A:
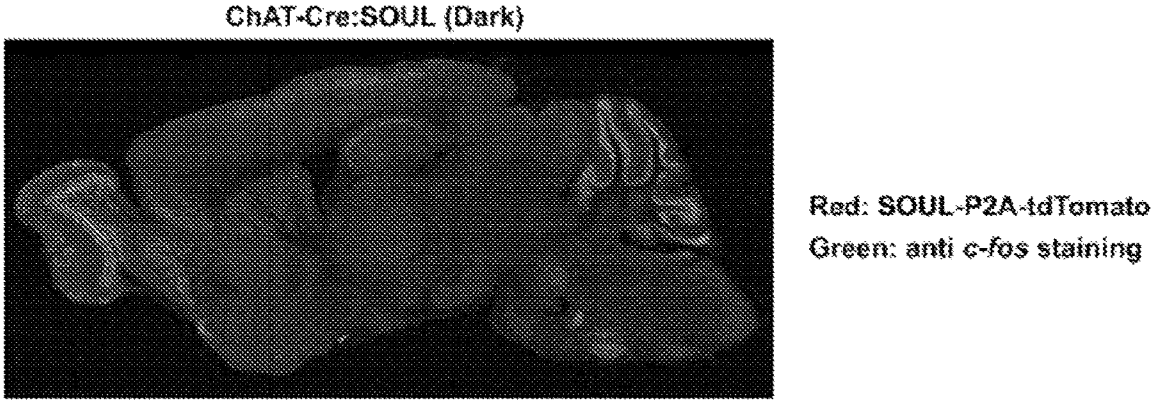
FIGS. 14A to 14E present images and a graph depicting the expression of c-fos in the brains of ChAT-Cre:SOUL mice in the dark and under laboratory ambient light according to exemplary embodiments of the disclosure.
Figure 14B:
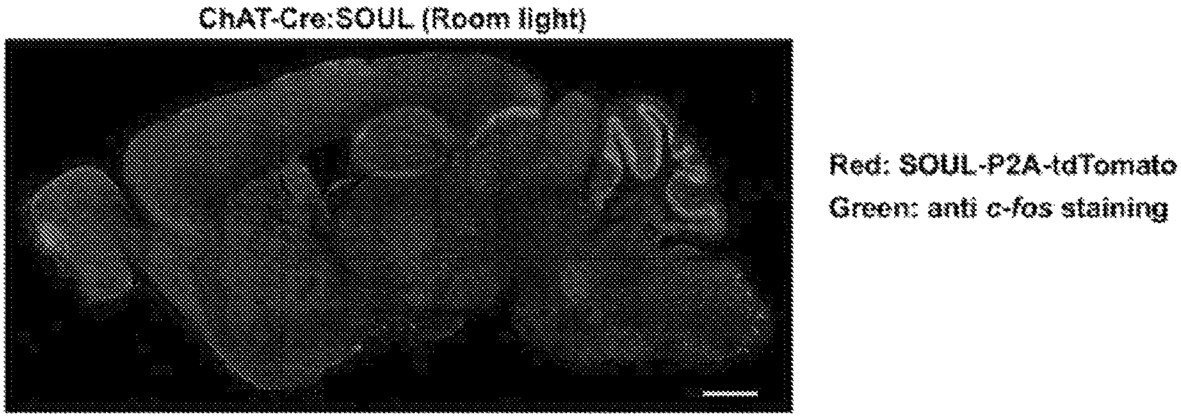
Figure 14C:
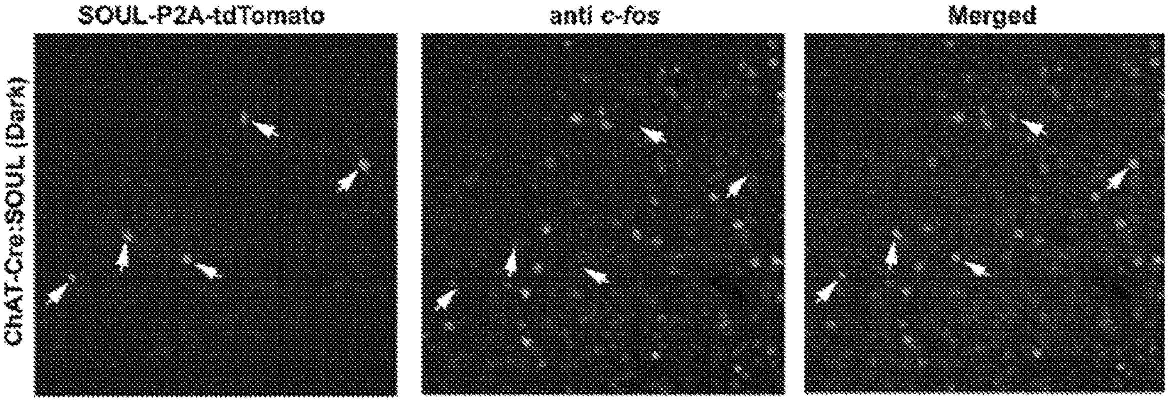
Figure 14D:
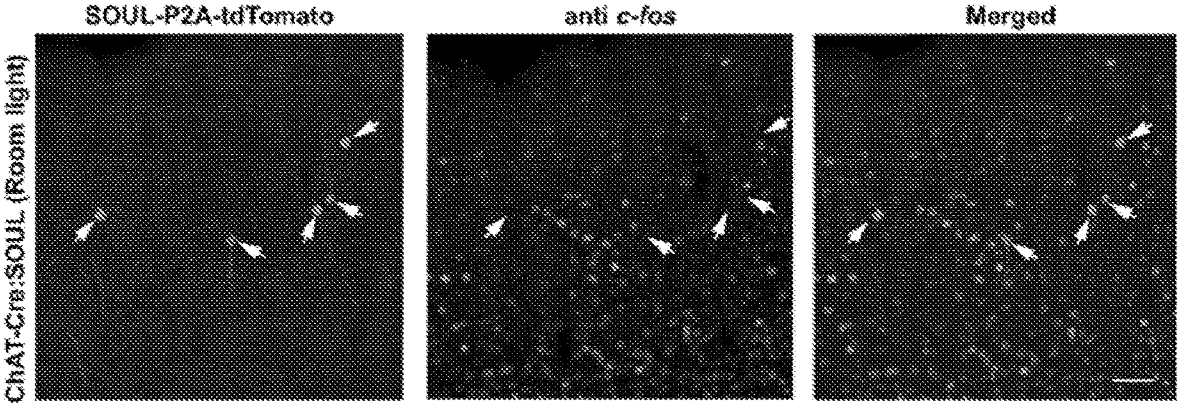
Figure 14E:
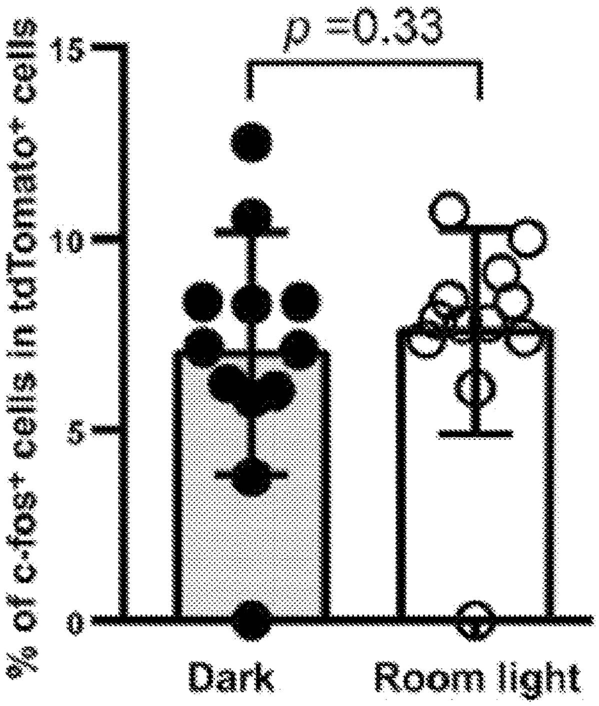

To test the ability of SOUL to modulate neuronal firing rates by transcranial light delivery in vivo, titer-matched adeno-associated viruses (AAVs) encoding SSFO or SOUL were injected into the mediodorsal thalamus (MD) in opposite hemispheres of the same C57BL/6J mice. To achieve adequate virus-mediated expression, a minimum period of at least four weeks was given after injection. Neuronal spiking activity was then recorded while delivering transcranial optical stimulations through an optical fiber positioned above the midline of the intact skull (FIG. 3A). Upon transcranial photostimulation, MD neurons in the SOUL-expressing hemisphere showed a significant increase in firing rate (FIGS. 3B and 3H) that scaled with light power (FIG. 3C), whereas MD neurons in the SSFO-expressing hemisphere were not significantly activated (FIGS. 3B, 3C, and 3H). In contrast, optical stimulation delivered through implanted fibers within the MD thalamus was sufficient to significantly increase the firing rates of neurons in both SOUL and SSFO-expressing MD (FIG. 12). Together, these results demonstrate that under matched conditions, SOUL, but not SSFO, can be activated via transcranial optical stimulation in mice.

Deep brain regions represent the most challenging targets for transcranial optogenetic method since light attenuation increases as a function of the total distance traveled through the skull and brain tissues. To address whether SOUL has sufficient photosensitivity to allow for transcranial optogenetic stimulation of the deepest regions in the mouse brain, lateral hypothalamus (LH) was selected as a target region for two reasons: first, it is one of the deepest areas in the mouse brain (~5.5-6.2 mm below the skull surface); second, it has well-characterized functions that can be readily assessed behaviorally (Jennings et al., 2013).

To test whether transcranial activation of SOUL increases neuronal activity in LH, an AAV encoding SOUL-P2A-tdTomato or a mCherry control fluorophore was injected into the LH of wildtype C57BL/6J mice, waited four weeks, performed transcranial optical stimulation (60s, 50 mW) via a removable optical fiber placed above the midline of the skull, and then stained LH for c-Fos immunoreactivity. In this condition, light had to travel a distance of up to 6.2 mm through the intact skull and brain to reach LH (FIGS. 3D and 3E). Following light stimulation above the skull midline, the number of c-Fos-positive LH neurons was significantly higher in SOUL-expressing mice than in control mice expressing only the fluorophore (FIGS. 3F and 3G). This indicates that non-invasive transcranial optical stimulation can activate SOUL-expressing neurons even in the deepest regions of the mouse brain.

Figure 15A:
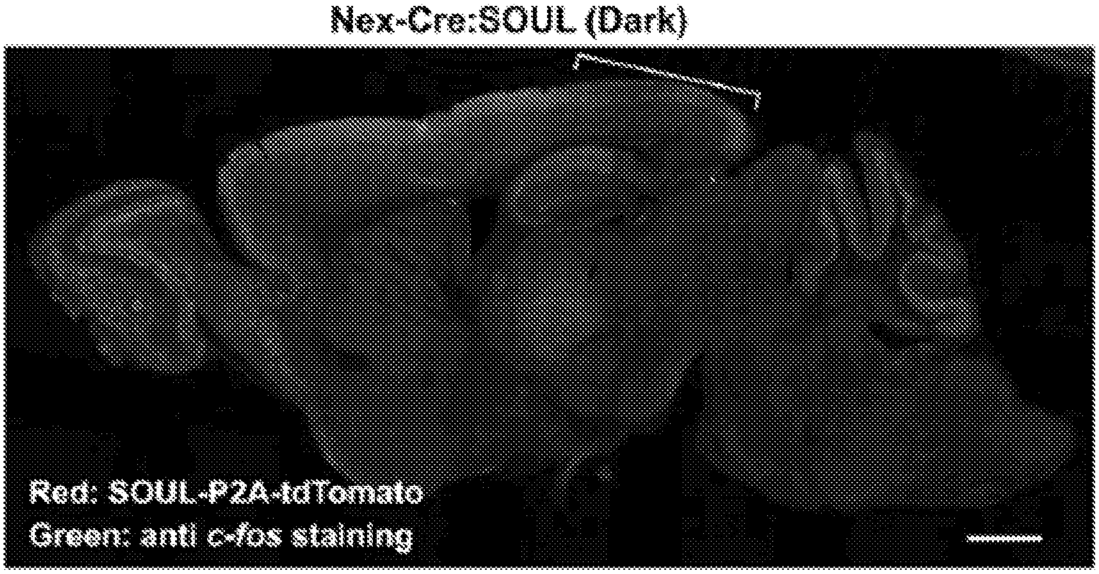
FIGS. 15A to 15D present images depicting the expression of c-fos in the brains of Nex-Cre::SOUL mice in dark and the laboratory ambient light according to exemplary embodiments of the disclosure.
Figure 15B:
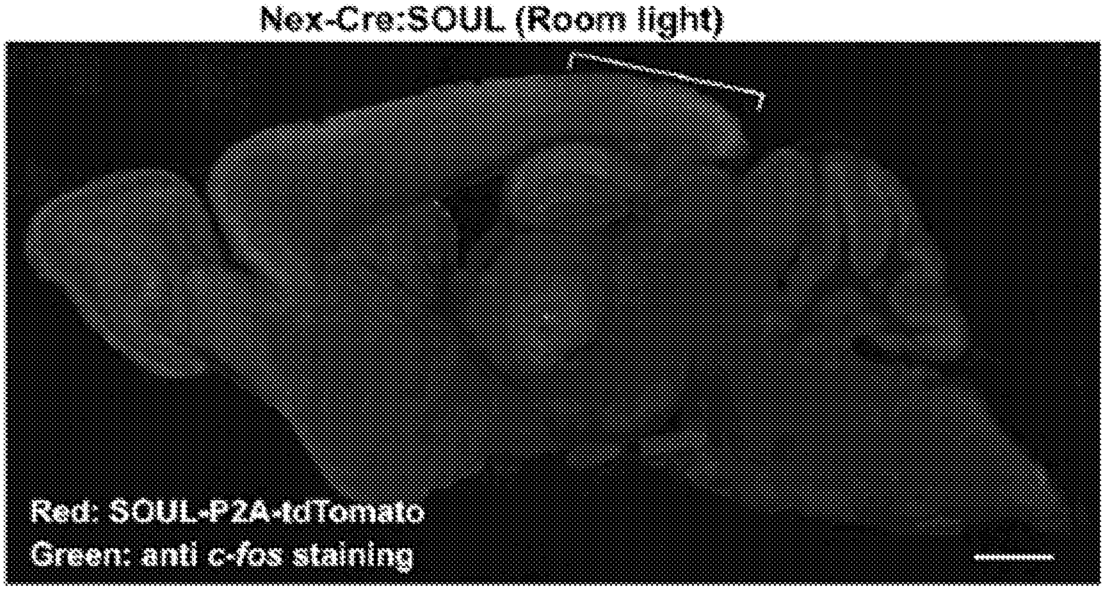
Figure 15C:
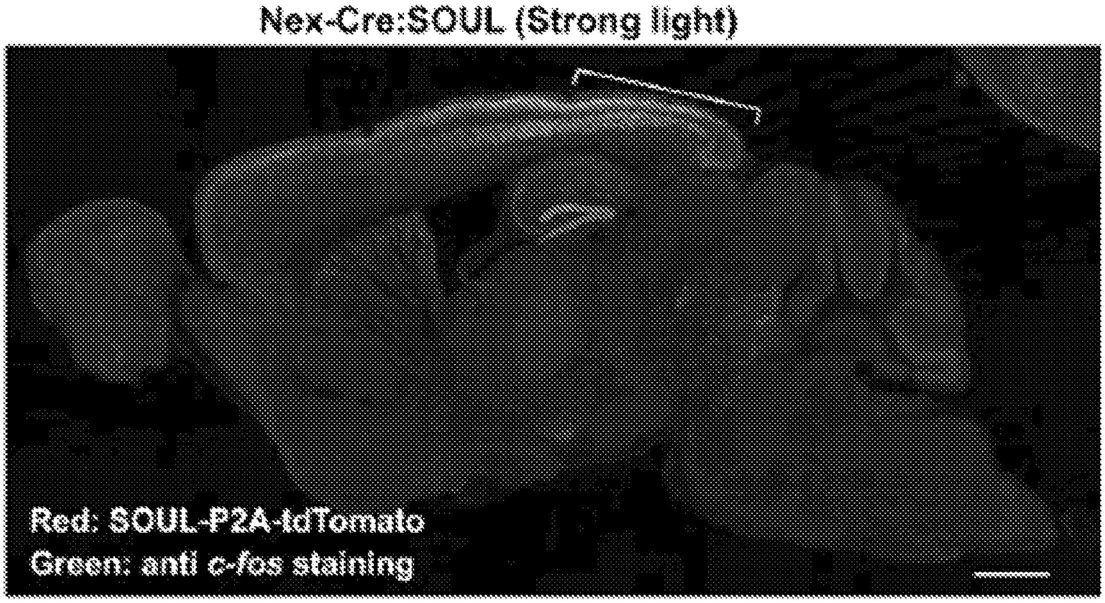

Because of high sensitivity of SOUL it was tested to see whether ambient light will activate SOUL-expressing neurons in the brain. The expression of c-fos protein was examined in SOUL:PV-Cre mice, SOUL:ChAT-Cre mice and SOUL:Nex-Cre mice under dark and room light (150 lux) conditions. No significant differences in c-fos expression were found in the brain of these mice between dark and light conditions (FIGS. 13, 14, 15A, and 15B), suggesting that ambient light will not cause significant activation of SOUL-expression neurons in the mouse brain. However, under strong light (468 lux in a fume hood), it was seen that strong c-fos staining in the brain, especially in the visual and somatosensory cortex (FIG. 15C). Since Nex-Cre is highly expressed in retinal ganglion cells, SOUL-P2A-tdTomato expression was examined in the wholemount retina and noticed a strong tdTomato expression in the retina (FIG. 15D), which may contribute to the cortical neuronal activation under strong light. Thus, cautions should be taken to avoid exposing SOUL-expression mice to strong light.

Example 3: SOUL Allows Transcranial Optogenetic Control of Mouse Behavior

Figure 4A:
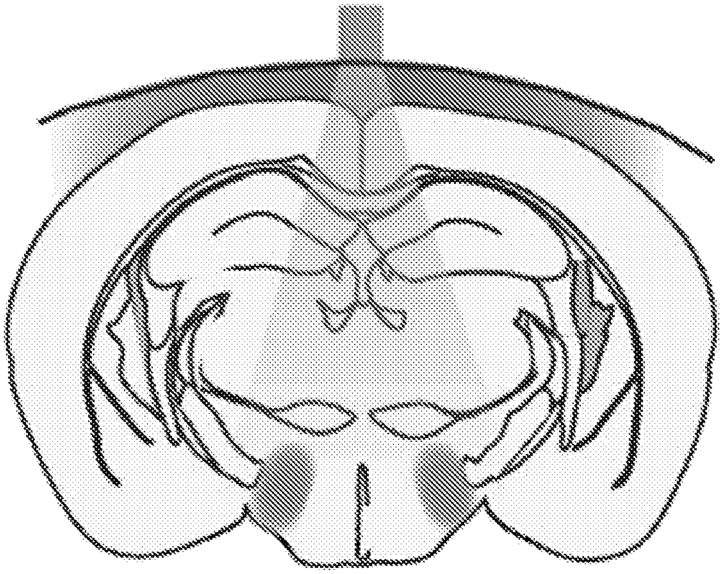
FIGS. 4A to 4D show a schematic, plot, graph, and image, respectively, representing transcranial stimulation of SOUL in LH CaMKII$^+$ neurons inhibits feeding behavior according to exemplary embodiments of the disclosure.
Figure 4B:
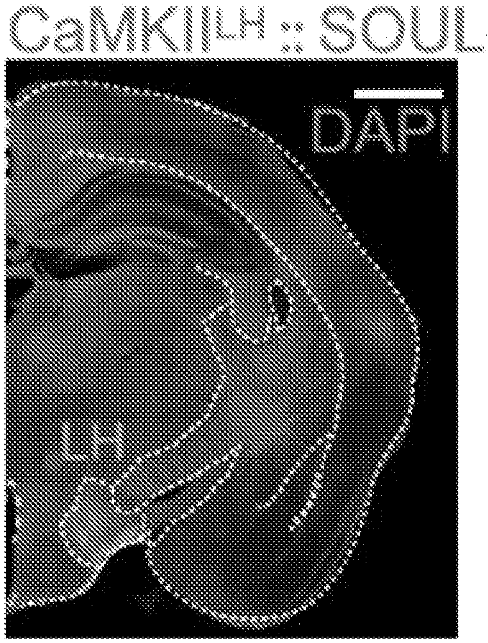
Figure 4C:
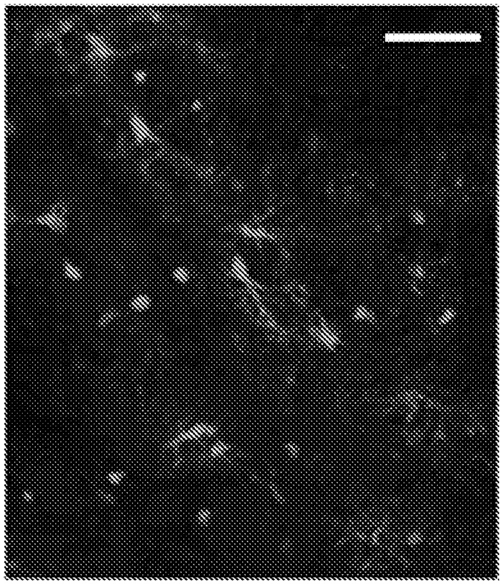
Figure 4D:
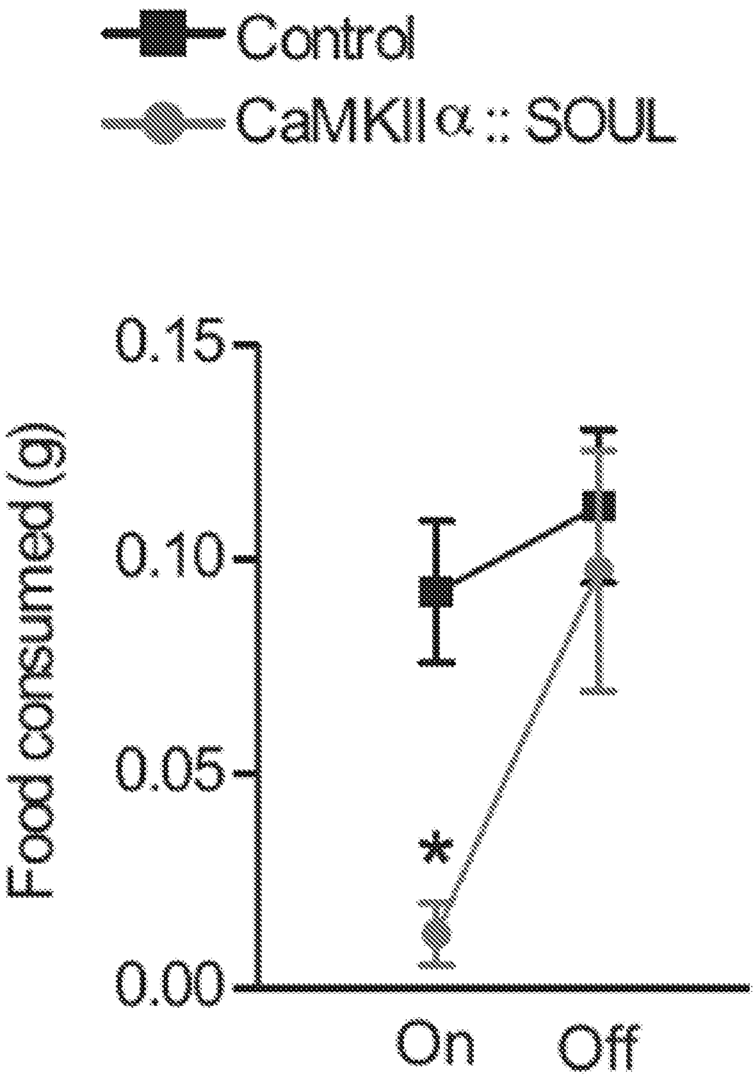
Figure 15D:
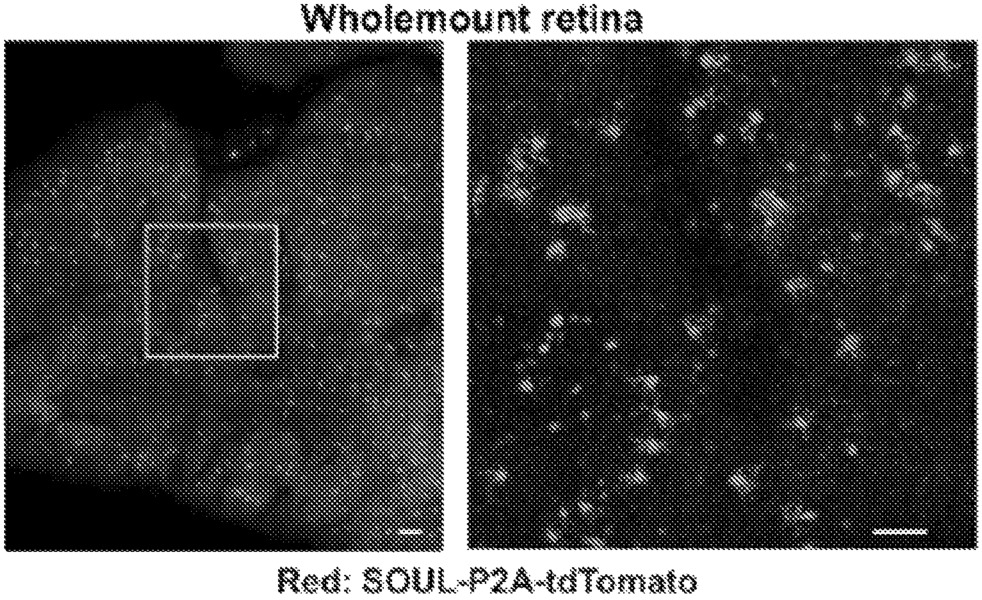
Figure 16A:
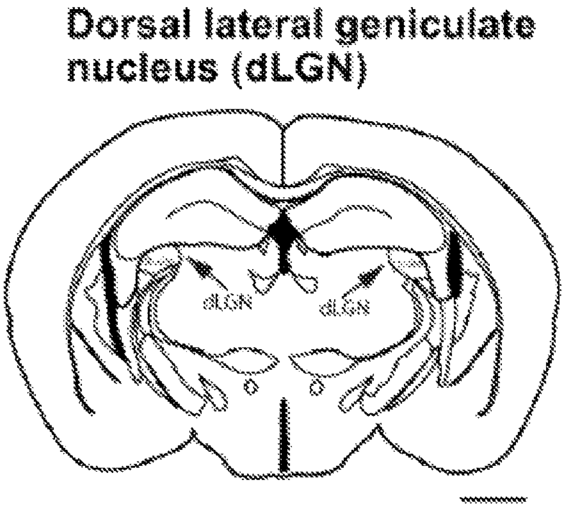
FIGS. 16A to 16F show schematics, graphs, and images showing that transcranial stimulation does not induce visual system activation according to exemplary embodiments of the disclosure.
Figure 16B:
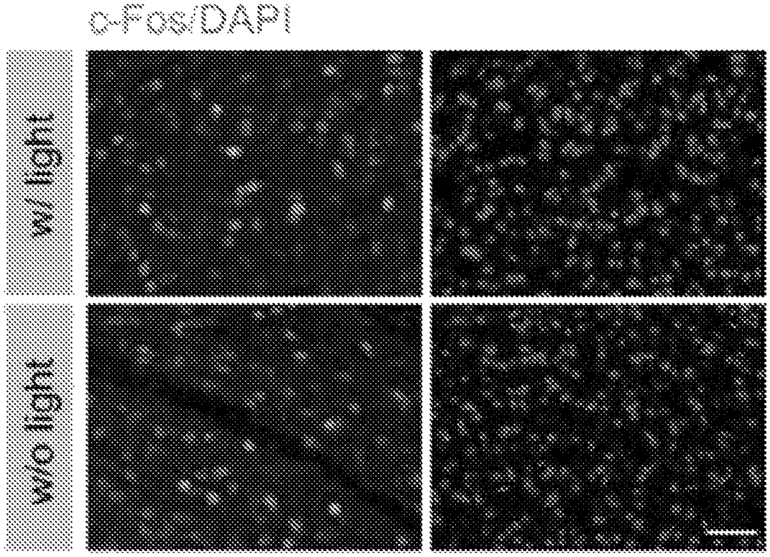
Figure 16C:
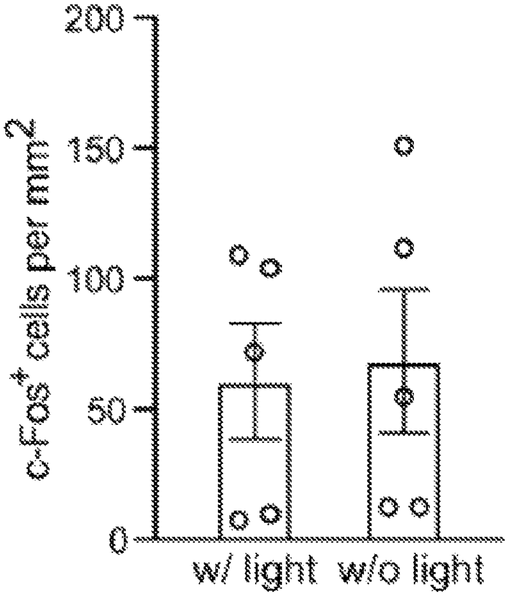
Figure 16D:
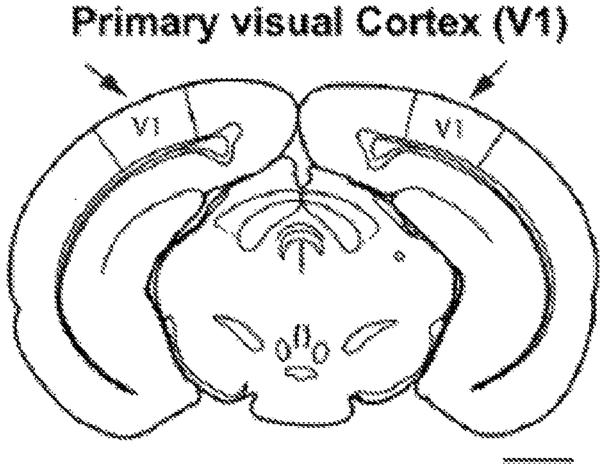
Figure 16E:
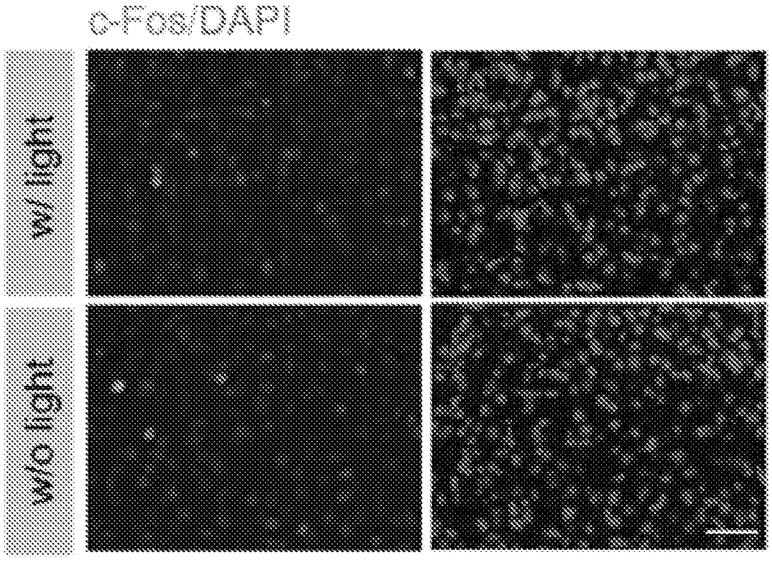
Figure 16F:
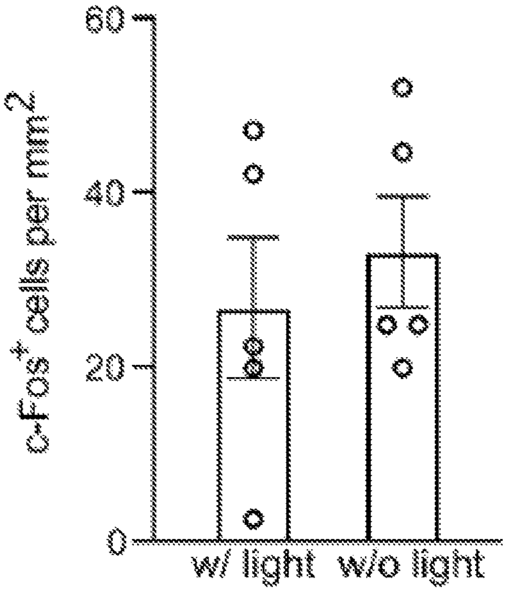

Next, it was tested to assess if transcranial optogenetic activation of LH is sufficient to cause observable behavioral effects in mice. Previously, it has been shown that photoactivation of excitatory neurons in LH suppressed feeding in food-deprived mice (Jennings et al., 2013). It was then tested to see if such effects can be induced by transcranial SOUL activation of CaMKII+LH neurons and reversed by SOUL deactivation. To do this, an AAV encoding CaMKII-Cre was bilaterally injected into the LH of SOUL knock-in mice, thereby specifically expressing SOUL in CaMKII+LH neurons (FIGS. 4*a-c*). AAV encoding mCherry under CaMKII promoter was used for control group. Light was delivered through a removable patch cable placed above the skull midline, allowing equivalent illumination of LH in both hemispheres (FIG. 4A). Food-deprived SOUL-expressing mice showed significantly reduced food consumption during a 10-minute window after SOUL activation by blue light (473 nm, 60 s, 50 mW). Moreover, this behavioral effect was completely reversed following deactivation of SOUL via transcranial illumination with orange light (589 nm, 100 s, 25 mW; FIG. 15D). Also, the illumination itself did not activate the mouse's visual system (FIG. 16). These results showed that SOUL can be used to manipulate neuronal activity and behavior through non-invasive transcranial delivery of light in a mouse brain region as deep as the LH.

Figure 5A:
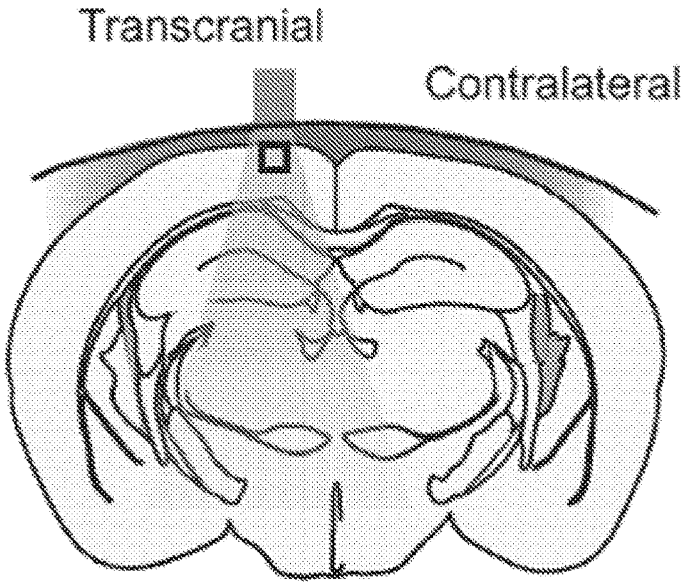
FIGS. 5A to 5C show a schematics, confocal images, and graphs representing Microglia activity in response to transcranial optical stimulation or fiber implantation according to exemplary embodiments of the disclosure.
Figure 5B:
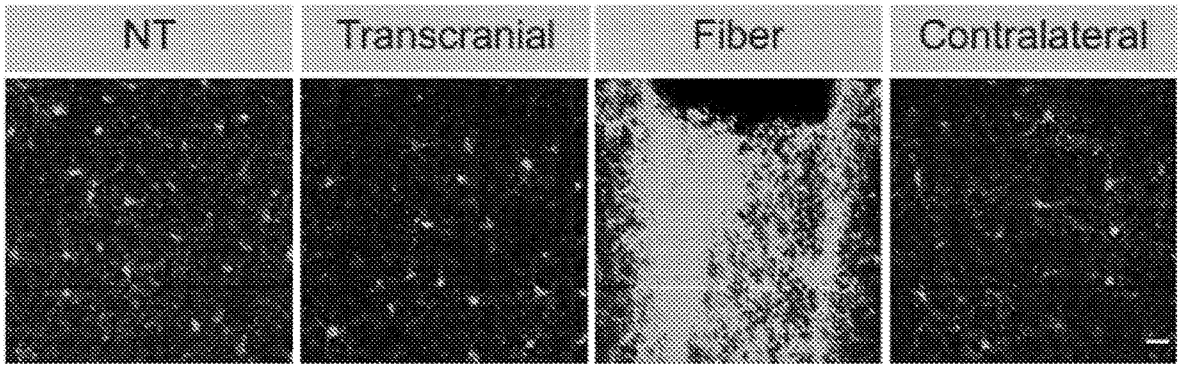
Figure 5C:
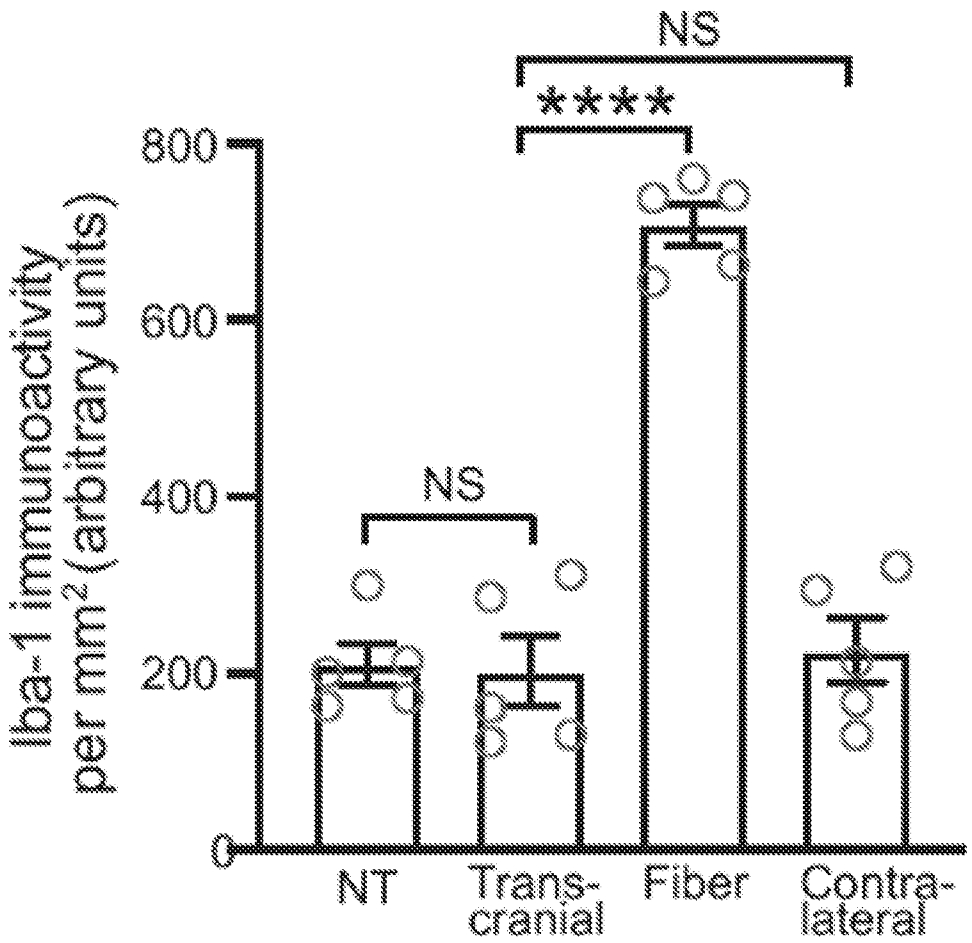

Next, the safety of transcranial light stimulations was assessed as well as intracranial and transcranial stimulation methods in terms of brain tissue injury were compared. Potential cell inflammation and injury was assessed by microglia activation (Kreutzberg, 1996). For this purpose, Iba-1 immunoreactivity was measured 24 hours after transcranial light delivery (same procedure as those used in the feeding behavior experiment) to naïve WT mice (no viral injection) or two weeks after fiber implantation in naïve WT mice. Naïve WT mice were also included without any treatment as a baseline control group. There was no increase in lba-1 immunoreactivity in mice after transcranial light stimulation as compared to control mice. In contrast, the lba-1 immunoreactivity of mice with fiber implantation was 2.4-fold greater than that of control mice (FIG. 5, One-way ANOVA, P<0.0001), indicating a significant inflammatory response. Therefore, in addition to its ability to reversibly modulate the activity of large, deep brain regions in mice, transcranial stimulation of SOUL does not cause brain inflammation and injury that can be associated with optogenetic fiber implantation (as indicated by elevated level of microglia activity).

Figure 6A:
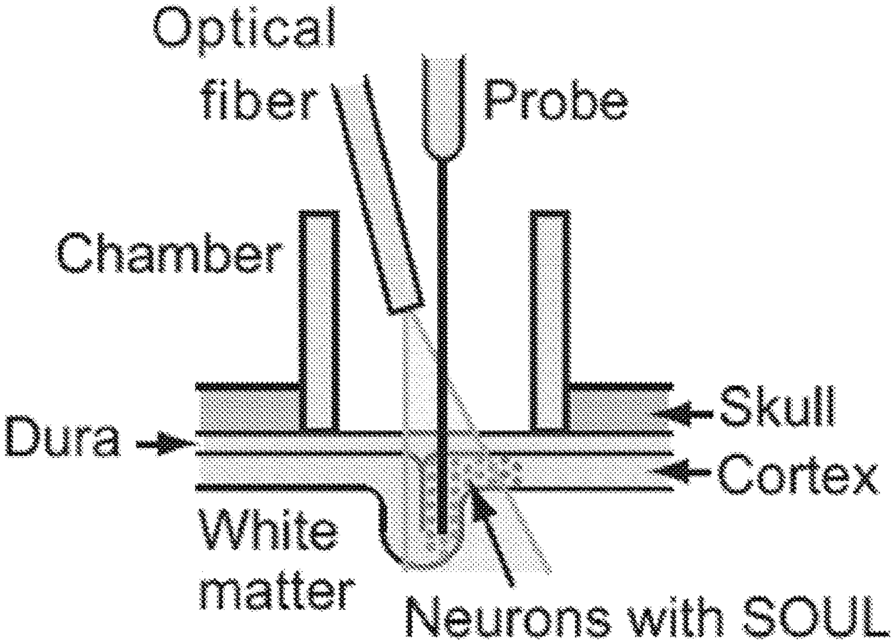
FIGS. 6A to 6K show schematics, plots, graphs, and images representing SOUL-mediated modulation of spiking activity in macaque neurons by transdural optical stimulation according to exemplary embodiments of the disclosure.

Example 4: SOUL-Mediated Large-Scale Optogenetic Activation of Macaque Cortex by Transdural Illumination Having demonstrated the capability of SOUL to be transcranially activated in mice, a method for large-scale, minimally invasive optogenetic stimulation of macaque cortical neurons by transdural illumination was tested. By replacing the traditional illumination approach—an implanted optical fiber—with an external fiber outside the dura, the limitation imposed by an implanted fiber on the total volume of brain tissue that can be illuminated was overcome, since the volume can be increased by increasing the diameter of the beam that illuminates the cortical surface while increasing the total power to maintain the same power density. Furthermore, transdural illumination not only prevents the damage typically caused by implantation of light delivery devices, but further minimizes potential inflammation or infections caused by perforating the dura to reach the brain. It was hypothesized that the high photosensitivity of SOUL would allow it to activate deep cortical neurons in macaques by light delivered above the dura, despite light attenuation by both the dura and the brain (FIG. 6A).

While keeping the dura intact, a standard cranial chamber was implanted around a craniotomy performed above the left lateral prefrontal cortex (area 8A (Paxinos, 2000)) of a Rhesus macaque monkey (*Macaca mulatta*). This allowed the region of interest to be accessible for virus injections, laser illumination and electrophysiological recordings. Injections of AAV9 encoding SOUL-P2A-tdTomato were performed under the human synapsin (hSyn) promoter along three penetrations 2 mm from each other, forming a triangle. In each penetration, injections were made at 7 depths from the brain surface distributed between 0.5 and 5.6 mm. Injections into cortex at such depths were possible due to their placement near the dorsal lip of the principal sulcus. The total superficial cortical area with opsin expression was measured to be 28 mm2 (see Example 6 and FIGS. 17A and 17B). Based on this observation and on the pattern of injection depths, the cortical volume with expression was estimated to be approximately 140 mm3.

Before each recording session, a step-index optical fiber was placed 4 to 10 mm above the dura, which helped generate a blue or orange light beam between 1.8 mm and 4.4 mm in diameter covering a cortical area of up to 15 mm2 with a lower power distribution disparity than a regular fiber or an implanted fiber. Single neuron and multiunit activity were recorded with a 16- or 32-channel linear probe implanted within the injected region (FIG. 6A; see Example 6). In each trial, 30 s of baseline activity was recorded, and then 10 s of blue light was delivered. Two minutes later, 20 s of orange light was delivered. This regime was repeated multiple times.

Figure 18A:
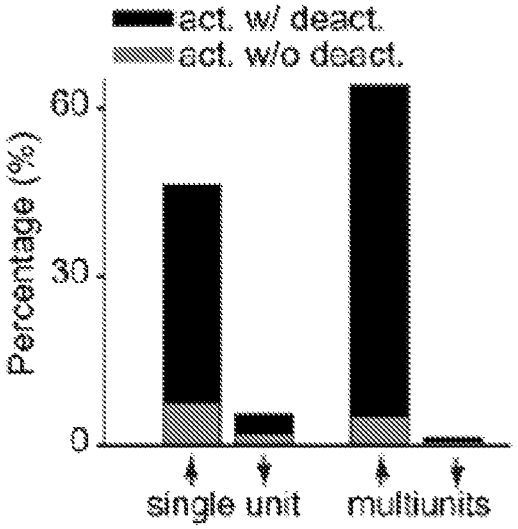
FIGS. 18A to 18C show graphs representing modulation of single neurons and multiunits, and modulation magnitude of non-significant units according to exemplary embodiments of the disclosure.
Figure 18B:
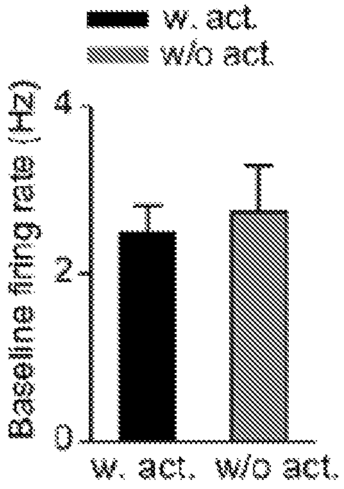
Figure 19:
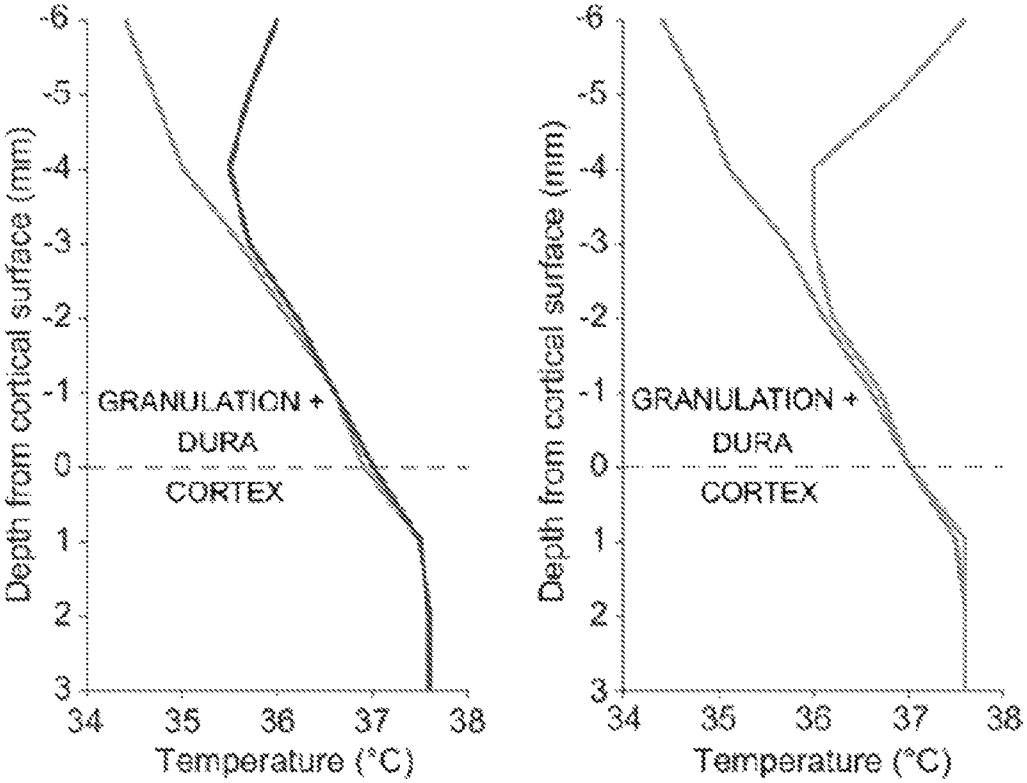
FIG. 19 shows graphs representing temperature measurements during light stimulation according to exemplary embodiments of the disclosure.

As shown in FIGS. 6B to 6E for two example single neurons, spiking activity increased upon blue light delivery and remained elevated after blue light offset (post-blue period, PB). After orange light delivery (post-orange period, PO), activity decreased back to baseline (BS, before blue delivery). To test whether each single neuron and multiunit was activated by blue light (e.g., FIGS. 6C and 6E), the firing rates during baseline and post-blue periods were statistically compared; to test the effectiveness of the orange light deactivation, the firing rate during the baseline and post-orange periods was compared. It was found that for 60% of all recorded units (128/215), the firing rate was significantly increased after blue light delivery (FIGS. 6F and 18A; paired t-test, $P<0.05$). Among all significantly activated units, 89% returned to baseline activity following orange light delivery (FIGS. 6F and 18A; paired t-test, $P<0.05$). Interestingly, other response types were observed in a minority of units: 3.4% of all units showed no significant activity increases after blue light but significant activity decreases after orange light, and 2.3% showed a significant decrease in activity in the post-blue period (FIGS. 6F and 18A), a phenomenon that may be due to inhibition either by SOUL-expressing interneurons or by inhibitory interneurons activated by SOUL-expressing pyramidal neurons. It was tested to assess whether there was a relationship between each unit's baseline firing rate and the presence of significant activation, but found no significant difference in baseline firing rate between units that showed activation and those that did not (FIG. 18B; Wilcoxon rank-sum test, $P=0.13$). Importantly, the discussed light stimulation paradigm did not cause any observable temperature increases inside the cortex, as measured by a temperature probe placed at multiple depths from the cortical surface (FIG. 19; see Example 6).

For all units showing significant increased activity in the post-blue period, the magnitude, latency, and duration of this effect were quantified. On average across these units, firing rates during the post-blue period were more than double the baseline (FIG. 6G; magnitude of activity increase=113%, std. dev.=214%, n=128). This effect emerged around 4.6s after blue light onset (median latency), varying largely across units (FIG. 6H; std. dev.=28.7 s). In 43% of the modulated units, the firing rate remained elevated for the entire 2 minutes post-blue period and returned to baseline only after orange light illumination (FIG. 6I).

Figure 18C:
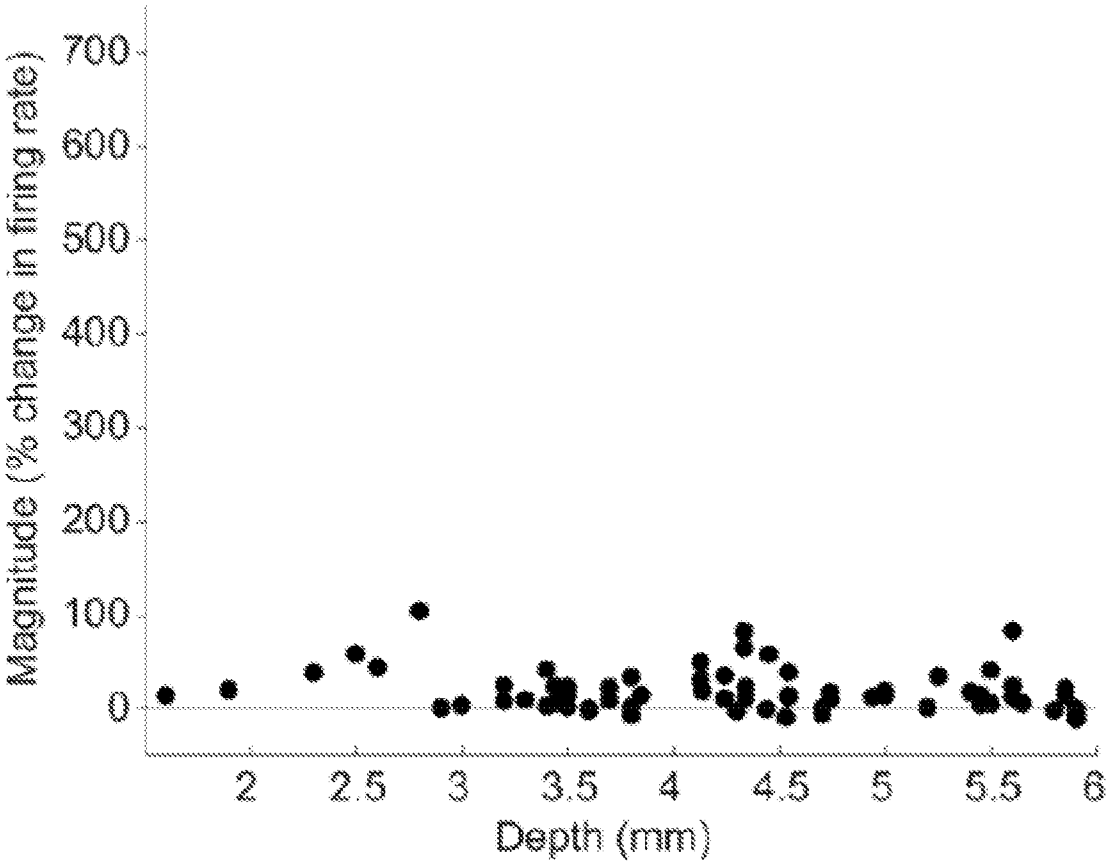

To examine the effects of optogenetic stimulation on units at various cortical depths, the units were using a multi-contact linear electrophysiological probe (FIG. 6A). Modulated units were found across all recorded depths, including the deepest recordings. Across significant units (but not across non-significant units; FIG. 18C), mean magnitude showed an overall decrease as a function of depth (FIG. 6J, correlation coefficient=−0.26, $p=9.6\times10{-5}$), while the highest percentage of modulated units was observed between 2 and 3 mm deep (FIG. 6K). Since the thickness of Rhesus macaque cortex typically ranges between 2 and 3 mm, the results indicate that external optical stimulation of SOUL allows activation of neurons across all depths in superficial cortical regions. To what extent neurons in deeper brain regions can be activated with external stimulation of SOUL remains to be determined by additional tests with injections and recordings in a wider range of regions and depths.

Figure 17A:
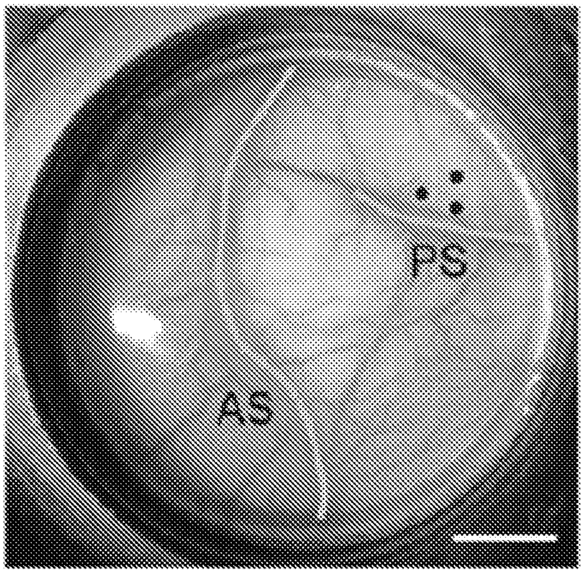
FIGS. 17A to 17D show images, plots and, graphs and images representing SOUL-mediated modulation of spiking activity by optical stimulation through artificial dura according to exemplary embodiments of the disclosure.
Figure 17B:
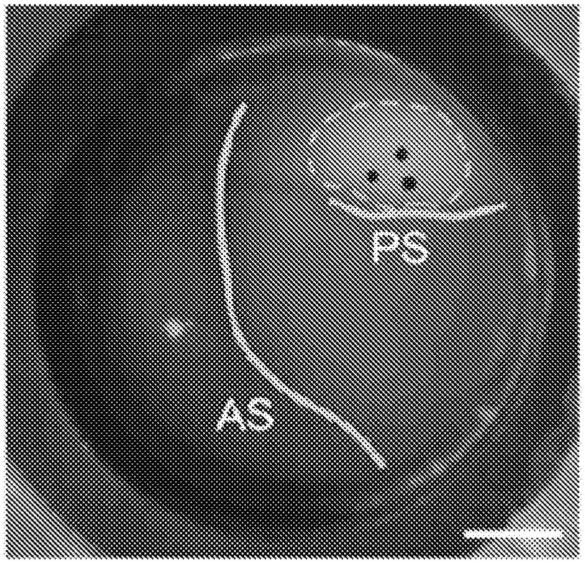

In addition to the experimental procedures performed on the left prefrontal cortex chamber, identical virus injections were performed in a chamber placed over the right prefrontal cortex of the same animal, where the native dura was surgically removed and replaced with a transparent artificial dura (FIG. 17A, see Example 6). These injections were performed on the same day as those on the left prefrontal cortex. The transparency of the artificial dura provided visual access to the cortical surface, thus allowing the tracking of the spatial pattern of SOUL expression across the cortical surface over time by measuring red fluorescence due to co-expression of tdTomato. This procedure thus allowed scheduling the experimental sessions on the left prefrontal chamber (intact native dura) for a period during which high levels of tdTomato fluorescence were visible on the right prefrontal chamber (artificial dura). High levels of red fluorescence were visible as early as 14 days, and as late as 5 months, after virus injections (FIG. 17B). All experimental sessions were performed during this period. Viruses may have persisted for longer, but it was not monitored beyond this period. Fluorescence covered an oval area of 28 mm2 around the 3 injection locations and the average expression radius around each location was 2.1 mm (see Example 6).

Figure 17C:
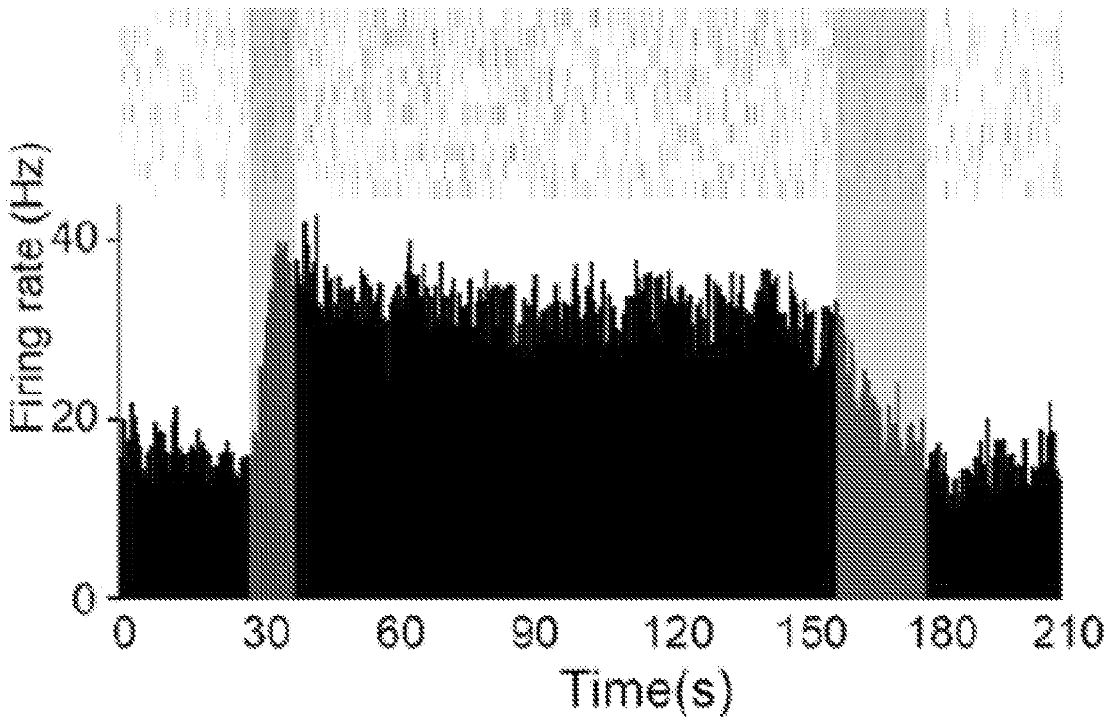
Figure 17D:
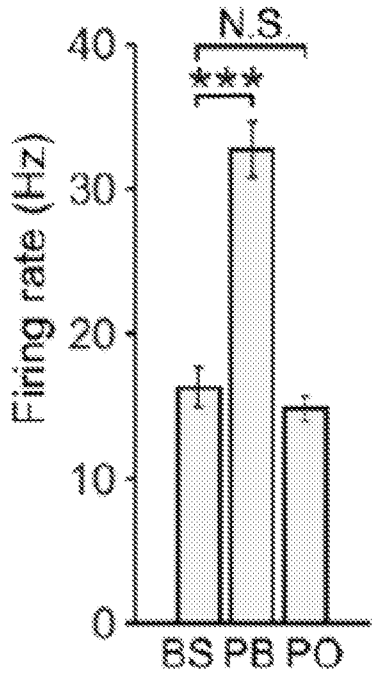

Measuring the spatial extent of expression served as a guide in deciding the extent of locations of electrode penetrations and the diameter of the laser beam. By further recording spiking activity with a linear electrode implanted through the artificial dura, it was confirmed that neurons showed activation and deactivation in response to blue and orange light illumination, respectively (FIGS. 17C and 17D). This demonstrates the feasibility of SOUL-mediated optogenetic activation using an artificial dura method. While an artificial dura implant is more invasive and may require additional care than an intact dura chamber to prevent infections or inflammation, it has the advantage of allowing experimenters to track the spatial and temporal patterns of virus expression in order to optimize the performance of experimental procedures, as the presented results demonstrate.

Example 5: SOUL Induces Local Field Potential Oscillations in Macaque Cortex

Figure 7A:
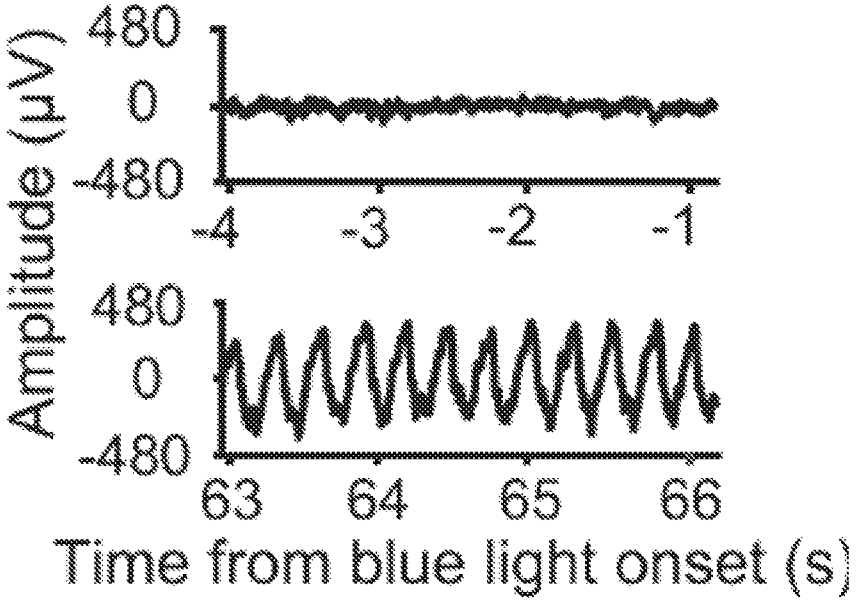
FIGS. 7A to 7G show local field potential amplitudes, spectrograms, and graphs representing modulation of LFP oscillations in macaque cortex by transdural optical stimulation of SOUL according to exemplary embodiments of the disclosure.
Figure 7B:
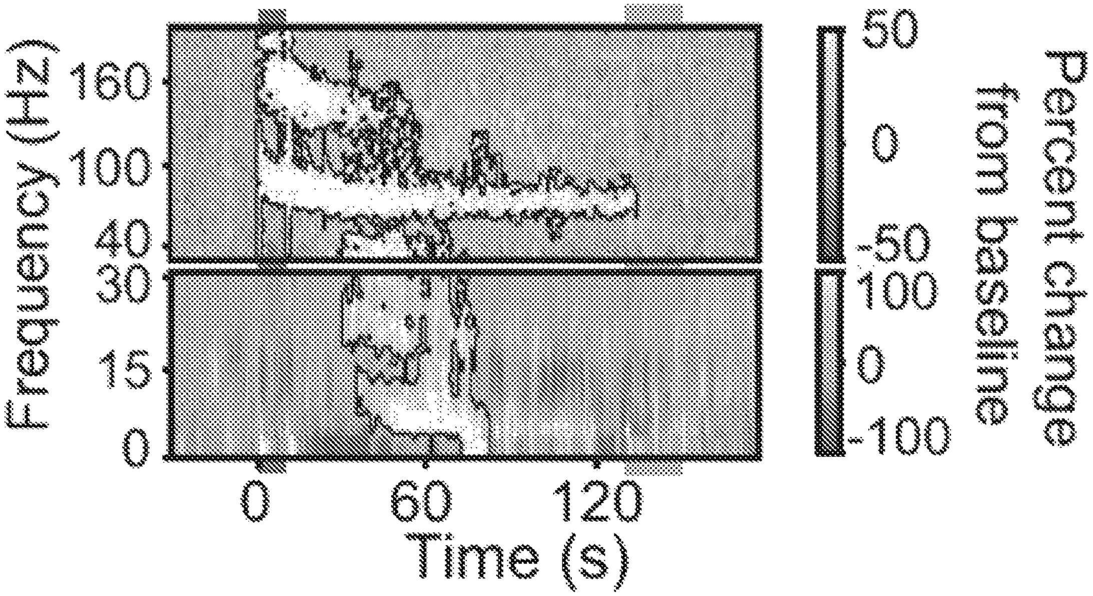
Figure 7C:
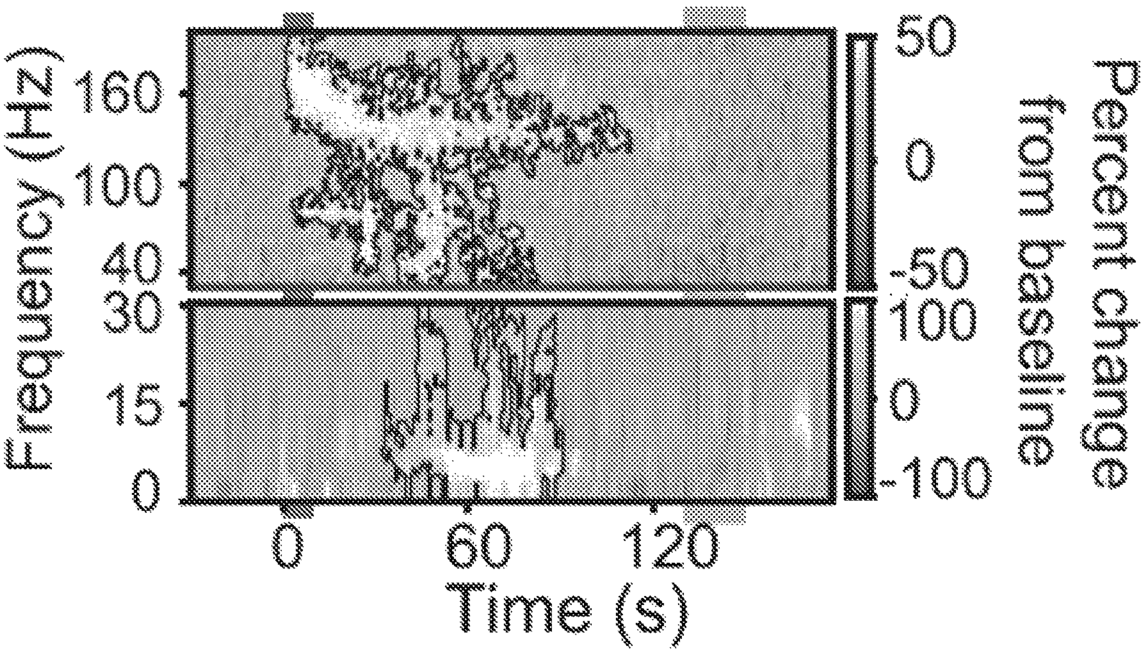

Visual inspection of the raw electrophysiological signals recorded during most sessions revealed the presence of strong rhythmic fluctuations in the local field potentials (LFPs) following blue light delivery (FIG. 7A). This suggested the possibility that optogenetic activation of macaque cortex expressing hSyn-SOUL-P2A-tdTomato induced synchronized oscillations in the synaptic activity of the underlying neuronal population. Time-frequency power analysis was performed in each recorded channel to examine whether the power at different LFP oscillatory frequencies was modulated upon blue light delivery compared to the baseline period. As shown in FIGS. 7B and 7C for two example LFP channels, the power of oscillations in several frequency bands was significantly elevated during the post-blue period with respect to the baseline period (cluster-based randomization test, alpha<0.05, See Example 6).

The above analysis was repeated for each of the 160 recorded channels and the percentage of channels showing a significant modulation in power at each frequency during the post-blue period with respect to the baseline period (FIG.

7D) was calculated. Among all channels, only significant power increases, but not decreases, were present. It was found that LFP power modulation did not occur randomly throughout all frequencies but was instead clustered into 3 large peaks (labeled alpha/theta, gamma2, and gamma3), and a smaller but still significant peak (labeled gamma1). These 4 peaks were detected using a quantitative analysis (see Example 6).

Figure 7D:
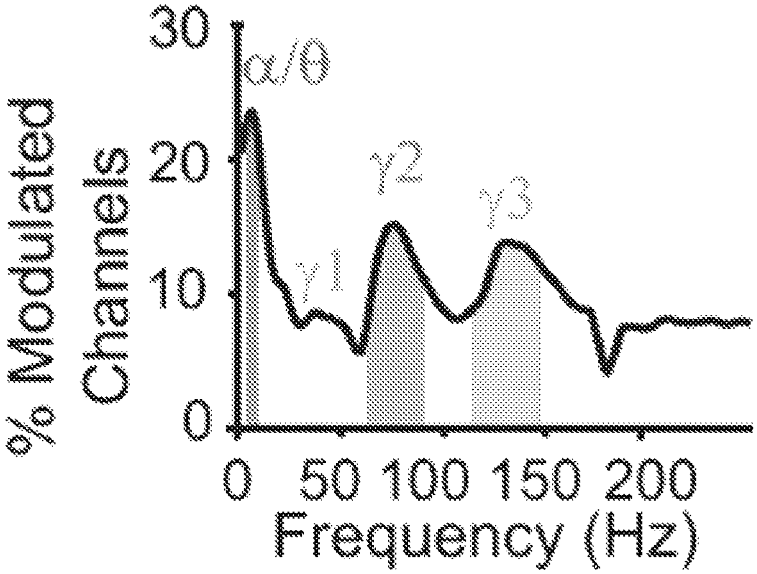
Figure 7E:
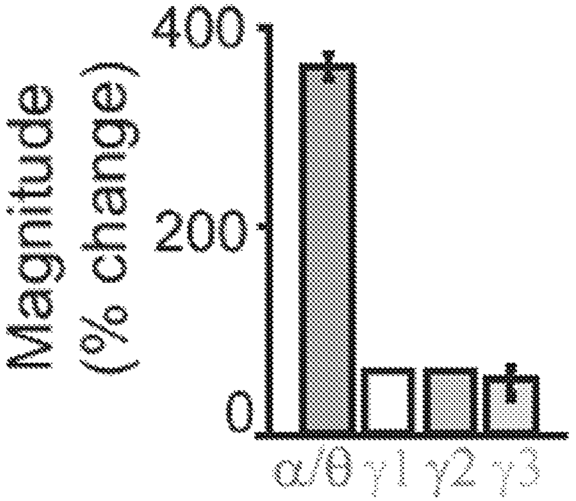
Figure 7F:
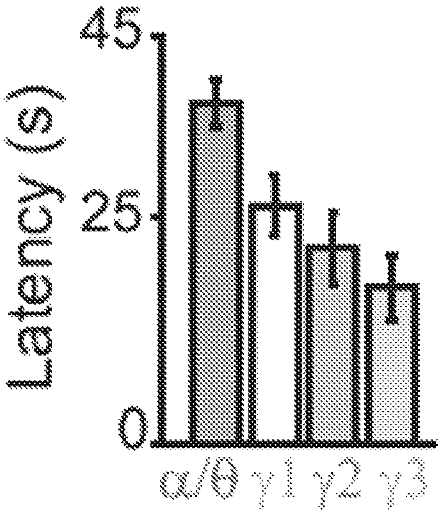
Figure 7G:
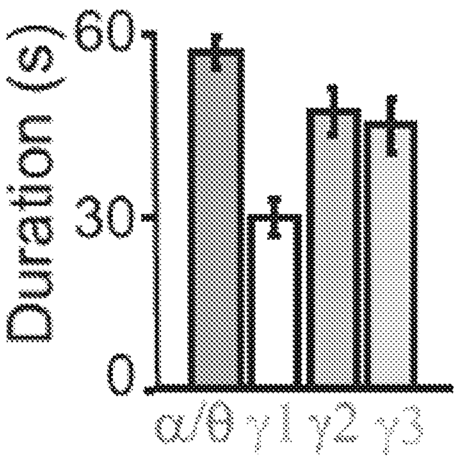
Figure 8A:
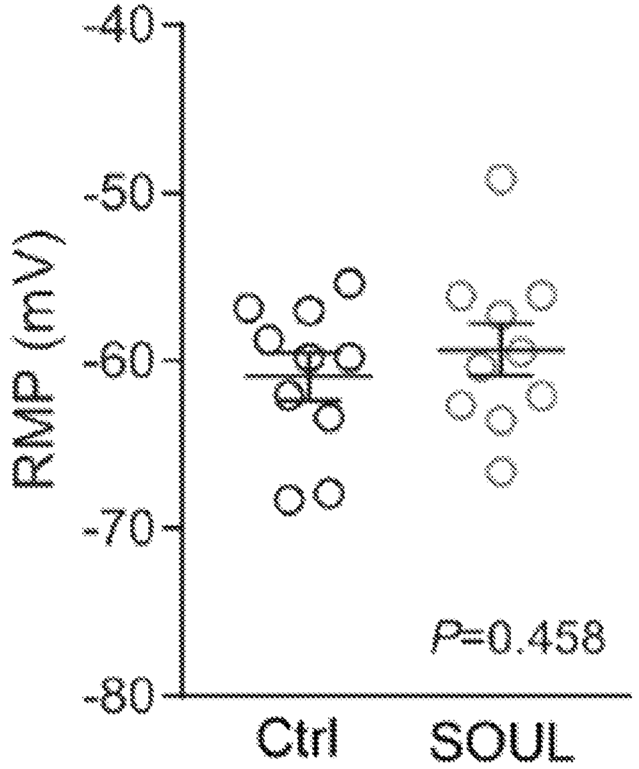
FIGS. 8A to 8D present graphs representing basic electrical properties of SOUL-expressing neurons according to exemplary embodiments of the disclosure.
Figure 8B:
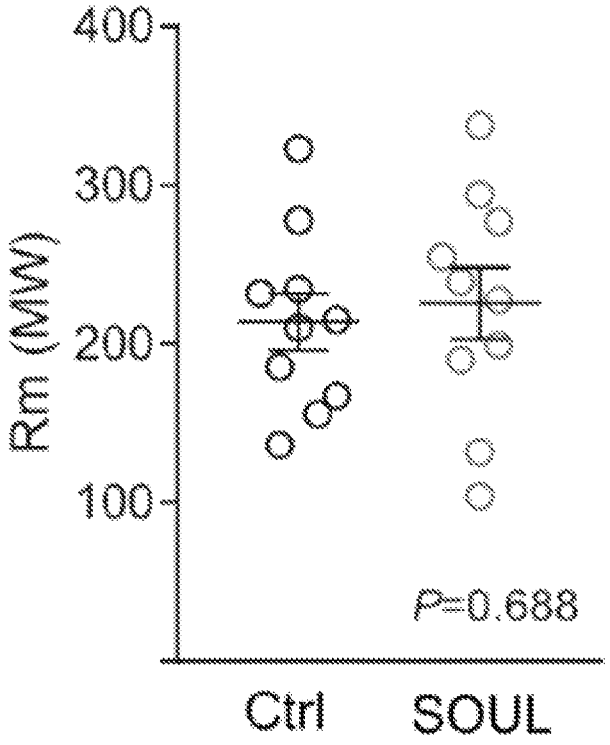
Figure 8C:
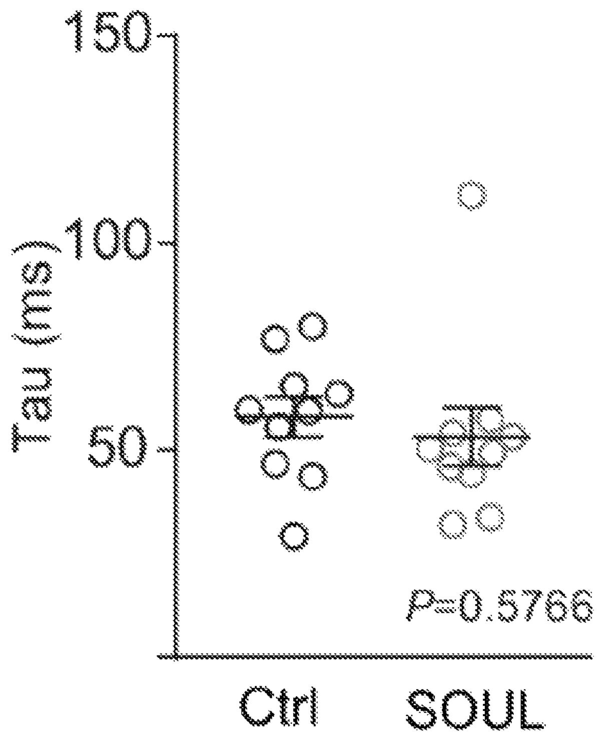
Figure 8D:
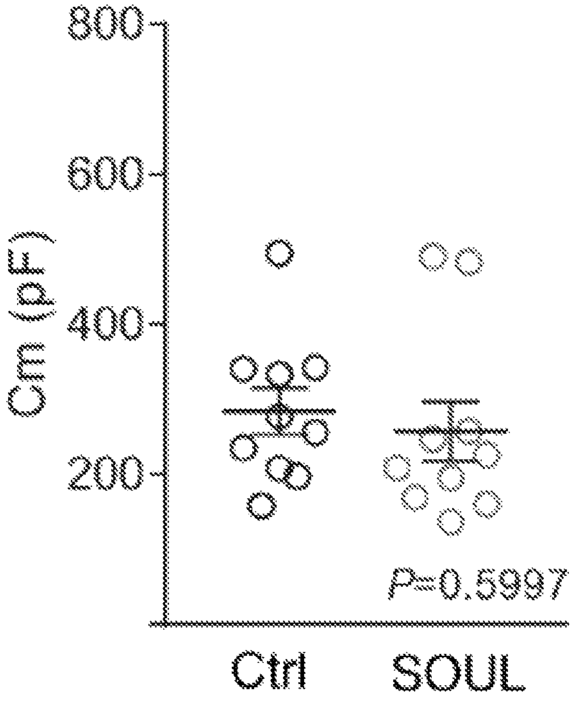

Across all channels, the increases in power were strongest in the alpha/theta band, with a 361% average increase from baseline, while increases of 53-63% were observed in the gamma bands (FIG. 7E). For each of the above frequency bands, the latency and duration of the power modulation between the blue light onset and the orange light offset were quantified. Across all channels, the mean latency showed an inverse relationship with the frequency of each band, with the highest frequency band (gamma3) showing the earliest effect (17 s), and the lowest band (alpha/theta) showing the latest effect (37 s, FIG. 7F). The alpha/theta band had the longest mean duration of modulation (58 s), in contrast with 30-45s for the gamma bands (FIG. 7G).

Lastly, to examine whether the power modulation in each frequency band ceased with orange light delivery, for each modulated channel it was tested whether the modulation remained present in the post-orange period. In 91% of modulated channels, the alpha/theta power modulation ceased after orange laser illumination, while the modulation in all gamma bands ceased in 100% of the channels. This indicates that deactivation of SOUL disrupts the optogenetically-induced oscillations.

Example 6: Therapeutic Use of SOUL in a Mouse Model of Parkinson's Disease (PD)

To assess therapeutic use of SOUL in a PD mouse model, three assays commonly used to detect despair/depression-like states were employed: sucrose preference test (SPT), forced swim test (FST), and tail suspension test (TST). While none of the three distinct PF populations (PF→CPu, PF→STN and PF→NAc) played a role in anxiety-like behavior (as measured by the zero maze test), inhibition of PF→NAc neurons led to a decrease in sucrose preference in SPT and an increase in immobility in both FST and TST, which indicated that this manipulation induced a despair/depression-like state in mice.

Figure 20A:
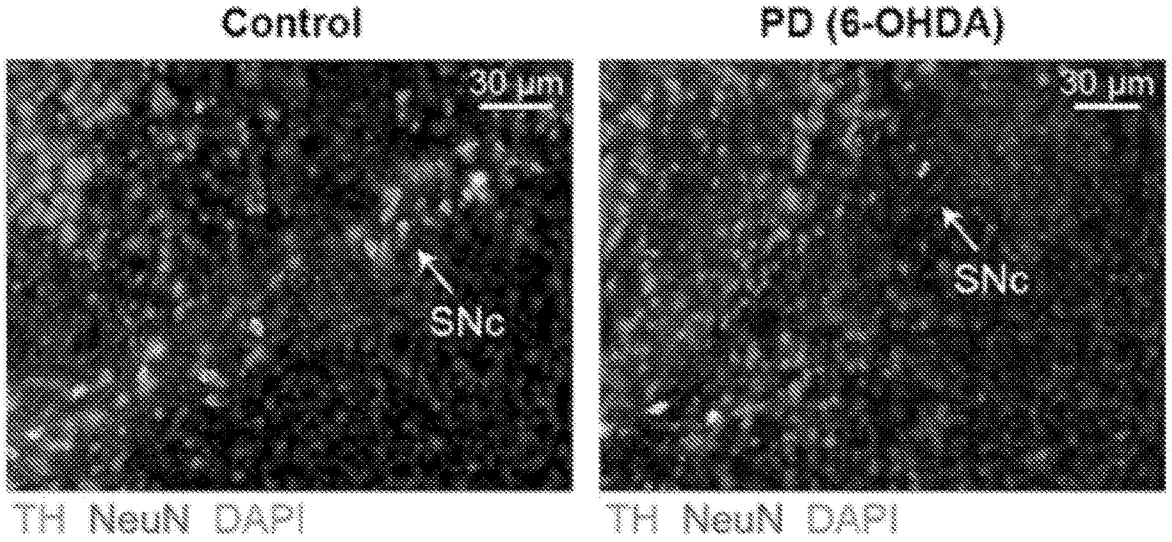
FIGS. 20A to 20E show that targeting of the parafascicular (PF) thalamus-to-nucleus accumbens (NAc) neuronal circuit with SOUL rescued depression-like behaviors in parkinsonian mice.
Figure 20B:
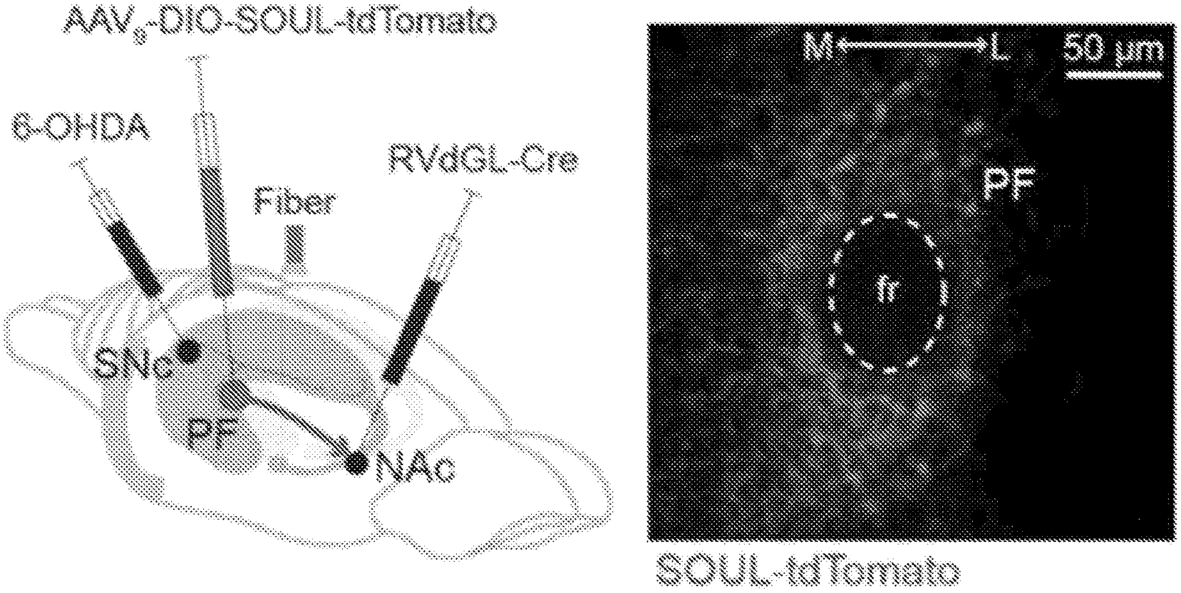
Figure 20C:
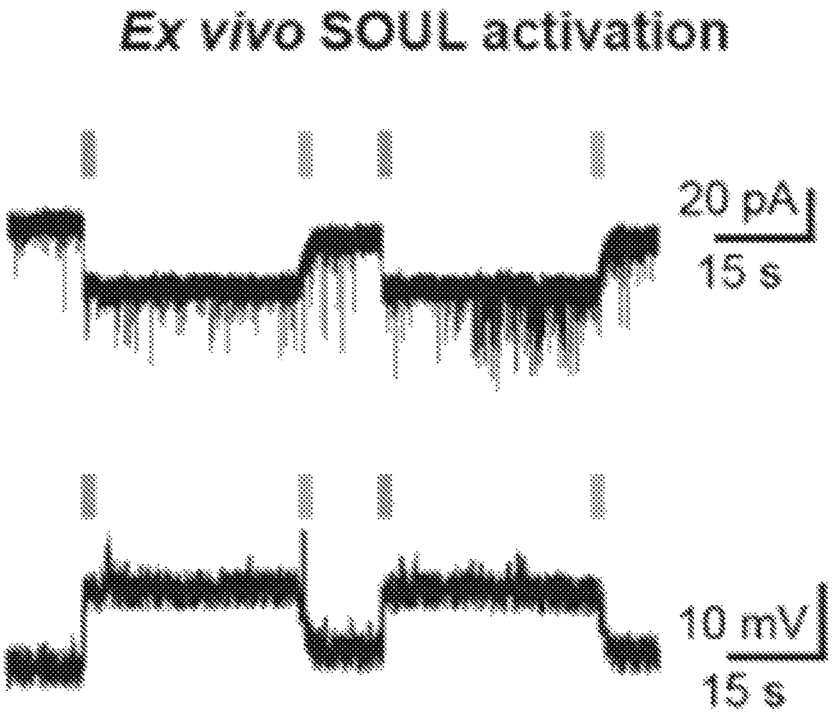
Figure 20D:
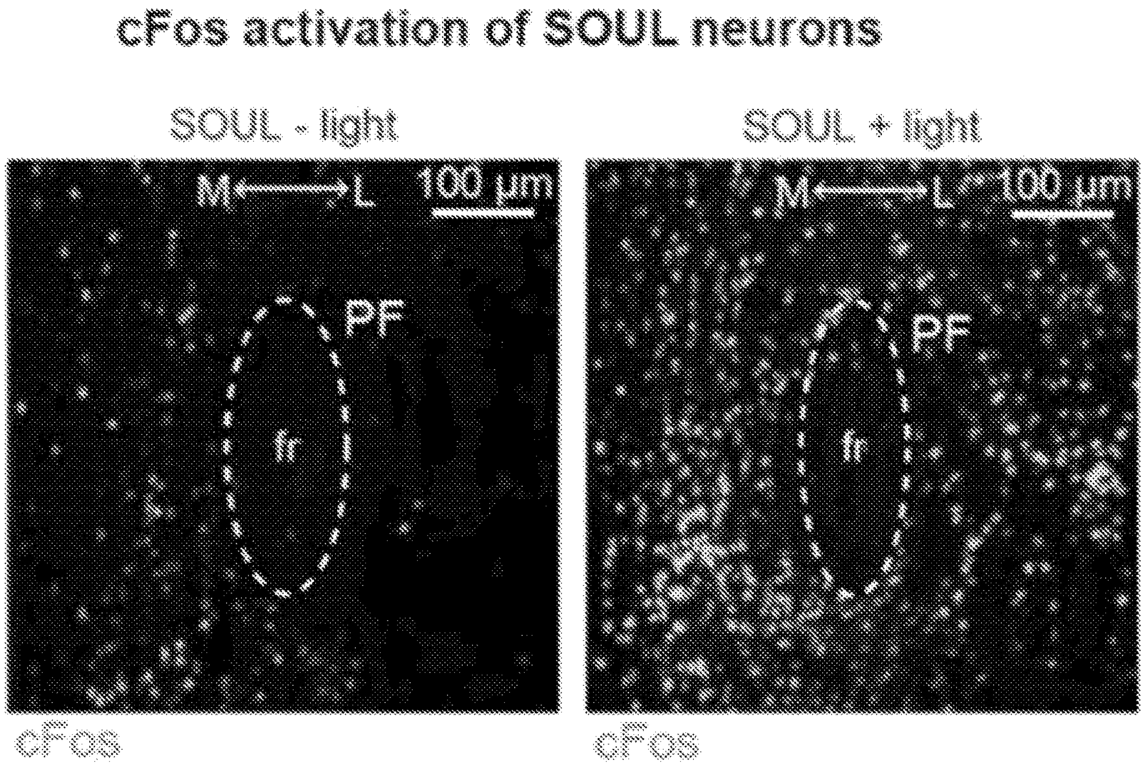
Figure 20E:
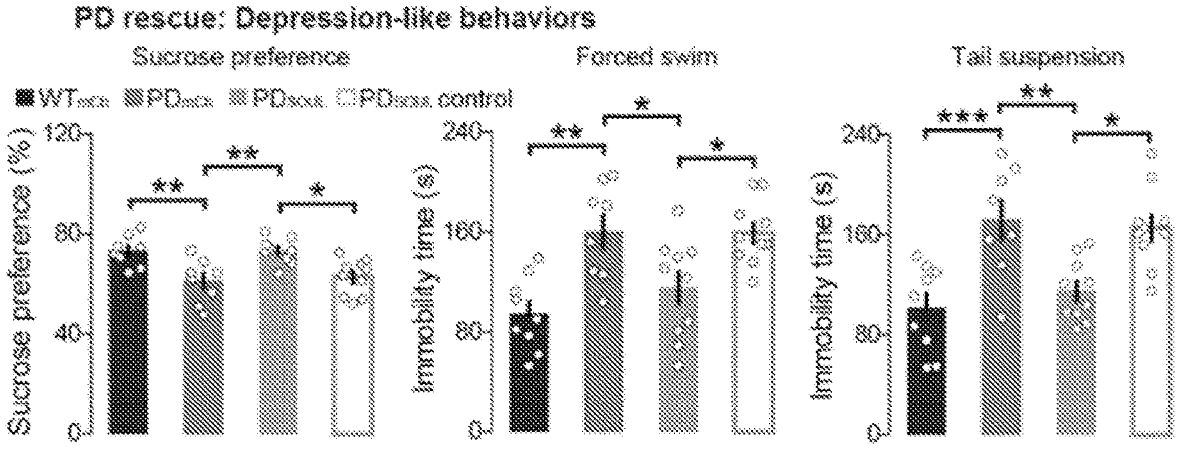

Next, it was examined whether PF→NAc neurons play an important role in PD mice. PD mouse models were generated by bilateral injections of 6-hydroxydopamine (6-OHDA) in substantia *nigra pars compacta* (SNc; Deumens et al.), which led to the loss of dopaminergic cell bodies in SNc (FIG. 20A). As expected (based on Carvalho et al.), PD mice exhibited a decrease in locomotion using the open field paradigm. Depression was then assessed, which has been identified as a common non-motor deficit in PD (Poewe). PD mice showed decreased preference in SPT, along with increased immobility in both FST and TST, which indicated a despair/depression-like state. It was speculated herein that increasing PF→NAc neuronal activity during behavioral assays might be sufficient to rescue depression-like phenotypes. We generated a Cre-dependent SOUL AAV was generated as described elsewhere herein, and PF→NAc viral labeling was verified (FIG. 20B). The ability to activate these neurons ex vivo within a user-defined time window (i.e., blue light-activated and orange light-inactivated) (FIG. 20C) as well as in vivo (FIG. 20D) was validated. Activating PF→NAc neurons in PD mice using light stimulation from outside the skull improved performance in all three assays used to detect despair/depression-like states, namely SPT, FST, and TST (FIG. 20E). Therefore, modulating PF circuits using SOUL was identified as an effective approach to rescue non-motor behavioral deficits in PD mice.

Example 7: Materials and Methods

Hippocampal Neuron Cultures

Hippocampal neurons were prepared from postnatal day 0-3 Swiss Webster (Taconic) mice as previously described (Chow et al., 2010; Klapoetke et al., 2014) but with the following modifications: dissected hippocampal tissue was digested with 100-200 units of papain (Worthington Biochem) for 8 min, and the digestion was stopped with ovomucoid trypsin inhibitor (Worthington Biochem). Cells were plated at a density of 52,000-64,000 per glass coverslip coated with Matrigel (BD Biosciences). Neurons were seeded in 75 ul Plating Medium containing MEM (500 mL, Life Technologies), glucose (2.5 g, Sigma), transferrin (50 mg, Sigma), Hepes (1.19 g, Sigma), glutagro (5 mL, 200 mM stock, Corning), insulin (1 mL, 12.5 mg/mL stock, Millipore), B27 supplement (10 mL, Gibco), heat inactivated fetal bovine serum (50 mL, Corning). After cell adhesion, additional 1 mL of Plating Medium was added. When glia density was 50-70% (about 2 days later), 1 mL of AraC Medium containing MEM (500 mL, Life Technologies), glucose (2.5 g, Sigma), transferrin (50 mg, Sigma), Hepes (1.19 g, Sigma), glutagro (1.25 mL, 200 mM stock, Corning), AraC (500 uL, 4 mM stock, Millipore), B27 supplement (10 mL, Gibco), heat inactivated fetal bovine serum (25 mL, Corning) was added. Neurons were grown at 37 C degree and 5% C02 in a humidified atmosphere. Cell plating density was determined using Countess II cell counter (Thermofisher).

Mouse Lines

All husbandry and experimental procedures in this study were approved by the Committee for Animal Care of the Massachusetts Institute of Technology, conformed to the guidelines of the Division of Comparative Medicine, and were consistent with the Guide for Care and Use of Laboratory Animals (Eighth Edition, 2011). The following mouse lines were used to crossed with the SOUL knock-in mice generated in this study: Parvalbumin-IRES-Cre (PV-Cre or PV-IRES-Cre, Stock No. 017320, The Jackson Laboratory), Drdla-Cre (D1-Cre, GENSAT BAC transgenic EY217) or ChAT-IRES-Cre driver mice (ChAT-Cre, Stock No. 006410, The Jackson Laboratory), to generate PV-Cre:SOUL, D1-Cre:SOUL and ChAT-Cre:SOUL mice. C57Bl/6J mice (Stock no. 000664, The Jackson Laboratory) were used for virus injection and behavior test. Adult mice of both genders, between 12-20 weeks old were used. Mice were housed at 22-25° C. on a circadian cycle of 12-hour light and 12-hour dark with ad-libitum access to food and water, unless placed on the food restriction schedule. In selected experiments, mice were food deprived the night before and given ad libitum food during the experiment (fasting not to exceed 16 hours in total). Mice were housed with cage mates except after surgery when they were housed individually.

Macaque

All procedures were approved by the Committee for Animal Care of the Massachusetts Institute of Technology, conformed to the guidelines of the Division of Comparative Medicine, and in accordance with NIH guidelines for animal research. A 19-year old adult male rhesus macaque (*Macaca mulatta*) weighing 12.5 kg was used in the study. The animal was housed in a cage on a circadian cycle of 12-hour light and 12-hour dark, with ad-libitum access to food and water, as well as toys and other objects for environmental enrichment.

Mouse Methods

Cre-Dependent SOUL Knock-In Mouse Line

The SOUL construct was created by introducing the T159C mutation into the SSFO (ChR2 C128S/D156A) cDNA by Quikchange mutagenesis. The SOUL cDNA was subcloned into the rAAV-hSyn1-P2A-tdTomato vector using Nhel and Hpal restriction enzyme sites, thereby generating rAAV-hSyn1-SOUL-P2A-tdTomato construct. To create the Rosa26 targeting vector, first, the Ai9 targeting vector (a gift from Hongkui Zeng; Addgene vector #22799) was modified by replacing the FseI-tdTomato-FseI fragment with a new FseI-BstBI-EYFP-MluI-FseI fragment, yielding vector Ai9-EYFPmod. The SOUL-P2A-tdTomato expression cassette was then subcloned into Ai9-EYFPmod using BstBI and MluI restriction sites on the vector and BstBI and AscI restriction sites on the insert. The ligation reaction reconstituted the 5' BstBI site but destroyed the 3' MluI site in the resultant Ai9-SOUL-P2A-tdTomato targeting vector. Critical elements were verified by DNA sequencing. The targeting vector was linearized with KpnI and purified by phenol/choloroform extraction prior to electroporation into R1 mouse embryonic stem cells for homologous recombination. ES cells were grown under G418 selection, and correctly targeted ES cell clones were identified by PCR screening with primers R26SA-F5: 5'-TTGGTGCGTTTGCGGGGATG-3' (SEQ ID NO: 4) and CAG02B: 5'-GTTATGTAACGCGGAACTCC-3' (SEQ ID NO: 5) (~1.1 kb band), and subsequently injected into blastocysts derived from C57BL/6 donor mice. High percentage chimeric male mice were mated to wild-type C57BL/6 female mice for obtaining germline transmission of the Cre-inducible SOUL allele and establishment of the line. Subsequent genotyping was carried out by polymerase chain reaction using the following primers: Rosa01F 5'-CACTTGCTCTCCCAAAGTCG-3' (SEQ ID NO: 6), Rosa02B 5'-TAGTCTAACTCGCGACACTG-3' (SEQ ID NO: 7), and CAG-02B 5'-GTTATGTAACGCGGAACTCC-3' (SEQ ID NO: 8). The product from the endogenous Rosa26 allele is 550 bp and the product that is specific for the modified Rosa26 allele is 325 bp. The mice were backcrossed to C57Bl6/J mice for at least 11 generations prior to breeding animals for experiments. This SOUL knock-in mice will be available from The Jackson Laboratory as Stock No. 032301.

In Vitro Recording

Neurons were transduced at ~2 days in vitro with AAV encoding hSyn-SSFO-P2A-tdTomto (Boston Children's Hospital Viral Core, 2 ul) or hSyn-SOUL-P2A-tdTomato (Boston Children's Hospital Viral Core, 1.5 ul) per well. For the assessments of photocurrent and intrinsic properties on the cultured mouse primary hippocampal neurons, whole-cell patch clamp recordings were performed as described (Nehme et al., 2018). Recording pipettes were pulled from thin-walled borosilicate glass capillary tubing (KG33, King Precision Glass, CA, USA) on a P-97 puller (Sutter Instrument, CA, USA) and had resistances of 3-5 MΩ when filled with internal solution (in mM: 128 K-gluconate, 10 HEPES, 10 phosphocreatine sodium salt, 1.1 EGTA, 5 ATP magnesium salt and 0.4 GTP sodium salt, pH=7.3, 300-305 mOsm). The cultured cells were constantly perfused at a speed of 3 ml/min with the extracellular solution containing (in mM: 119 NaCl, 2.3 KCl, 2 $CaCl_2$), 1 MgCl2, 15 HEPES, 5 glucose, pH=7.3-7.4, Osmolarity was adjusted to 325 mOsm with sucrose). All the experiments including the coverslips transferring and recordings were strictly performed at dark to avoid any activation by the light from the environments.

Cells were visualized with a 40× water-immersion objective on an upright microscope (Olympus, Japan) equipped with IR-DIC. Recordings were made using a Multiclamp 700B amplifier (Molecular Devices, CA, USA) and Clampex 10.7 software (Molecular Devices, CA, USA). In voltage clamp mode, 5s of 470 nm light pulses of different level of powers (3 j·tW/mm$^2$, 8 j·tW/mm$^2$, 20 j·tW/mm$^2$, 60 j·tW/mm$^2$, 1 mW/mm$^2$) were delivered to photoactivate the cells, and used 5s 1 mW/mm$^2$ 589 nm orange light to deactivate the SSFO or SOUL. The membrane potential was held at −60 mV in the presence of 100 jtM PTX and 50 jtM NBQX to block GABAergic inhibitory and AMPA mediated excitatory synaptic transmission. Subsequent analysis was performed using Clampfit 10.7 software (Molecular Devices, CA, USA). The data were stored on a computer for subsequent off-line analysis. Any cells with Rs more than 20 M9 at any time during the recordings were discarded.

Slice Recording

Acute brain slices were prepared from 1.5 to 4-month-old mice. Animals were anesthetized by intraperitoneal injection of avertin (tribromoethanol, 20 mg/ml, 0.5 mg per g body weight) and perfused with ice-cold NMDG-based solution: 92 mM N-methyl-d-glucamine (NMDG), 2.5 mM KCl, 1.20 mM NaH4PO4, 30 mM $NaHCO_3$, 20 mM HEPES, 25 mM glucose, 2 mM thiourea, 5 mM Na-ascorbate, 3 mM Na-pyruvate, 0.5 mM $CaCl_2$) and 10 mM MgSO4 (~300 mOsm, 7.2-7.4 pH). Following decapitation, brains were removed for coronal sectioning (300 m) in the same NMDG-based solution using a Vibratome 1000 Plus, Leica Microsystems, USA. Slices were then recovered in carbonated regular aCSF: 119 mM NaCl, 2.5 mM KCl, 1.2 mM NaH2PO4, 24 mM NaHCO3, 12.5 mM glucose, 2 mM MgSO4·7H2O, 2 mM CaCl2·2H2O (~300 mOsm, 7.2-7.4 pH) at 32-34° C. for 10 min and transferred to room temperature carbonated regular aCSF. Slices were allowed to recover for at least 1 h prior to all recordings. Slices were transferred into a recording chamber (RC-27L, Warner Instruments) and constantly perfused at room temperature (20-24° C.) with carbonated regular aCSF at a rate of approximately 2 mL/min. Borosilicate glass recording microelectrodes (King Precision Glass) were pulled on a P-97 horizontal puller (Sutter Instruments) and backfilled with KGlu internal recording solution (145 mM K-Gluconate, 10 mM HEPES, 1 mM EGTA, 2 mM Mg-ATP, 0.3 mM Na2-GTP, and 2 mM MgCl2). The internal pH was adjusted to ~7.3 with KOH and osmolarity adjusted to ~300 mOsm with K2SO4. The electrode tip resistance in the bath when filled with this internal solution was 3-5 MOhms. Recordings were performed in the dark after initially illuminating the slices with a custom mKate2 microscope filter (Ex max 590 nm, Em max 635 nm) and a mercury arc lamp. Cells were visually identified based on visualization of the tdTomato fluorophore. Recordings were initiated after seal rupture, initial stabilization, and equilibration of the whole-cell configuration for at least 3 min to allow dialysis of the internal recording solution. In order to measure the rheobase current, current clamp traces were recorded with 40 sweeps of current injections, each lasting 500 ms and starting from −150 pA with increments of 25 pA with (ON) or without (OFF) a 2s period of light pulse preceding the injection. Resting membrane potentials were determined in current clamp setting at baseline, after a 2s pulse of ON light (GFP filter), and after a 2s pulse of OFF light (mKate2). Photocurrents were measured in voltage clamp while holding the cell at −70V. The firing facilitation of SOUL was determined by examining the number of action potentials elicited upon current injection for several steps with or without prior 2s illumination with ON light (GFP filter) in voltage clamp configuration. For the membrane time constant, voltage-clamp trace recording followed a 2s ON light pulse (GFP filter) for 20-30 min, followed by a 2s OFF light pulse (mKate2) to return to baseline. The time constant was calculated by averaging the current for several time bins (each 1 min). The current of each bin was normalized to the peak current bin (first time bin). Tau (defined as the time when current is 1/e of max) was calculated from a mono-exponential fit. Data were acquired using a MultiClamp 700B amplifier and a Digidata 1440A. All analysis was performed using pCLAMP10 (Axon Instruments, Molecular Devices) and MATLAB.

Virus Injection

Mice were primed for anesthesia in an induction chamber with a mix of 5% isofluorane/O2 circulated at a rate of 1 L/min. Deeply anesthetized mice were maintained under anesthesia with 1-1.5% isoflurane/O2 and mounted on a stereotactic frame. The animals' heads were shaved, and the remaining hair was removed with Nair. Body temperature was measured through a rectal probe and maintained using an electrical heating pad. Injections were performed with a glass micropipette (7-9 μm diameter). The injection speed was controlled at 100 nl/min with a micromanipulator (Quintessential Stereotaxic Injector, Stoelting). For in vivo electrophysiology experiment in mouse, titer-matched adeno-associated virus (AAV) encoding hSyn-SSFO-P2A-tdTomto (Boston Children's Hospital Viral Core, total volume of 150 nl) or hSyn-SOUL-P2A-tdTomato (Boston Children's Hospital Viral Core, total volume of 150 nl) was injected into the mediodorsal thalamus (MD) on opposite hemispheres of the same C57Bl/6J mice at the following coordinate: anterior posterior (AP) −1.3 mm, medial lateral (ML)±0.6 mm, dorsoventral (DV) −3 mm. For the optical stimulation-evoked c-Fos staining experiments, AAV encoding hSyn-SOUL-P2A-tdTomato (Boston Children's Hospital Viral Core, total volume of 120 nl) or mCherry (Penn Vector Core, total volume of 120 nl) was injected into the lateral hypothalamus (LH) of C57Bl/6J mice at the following coordinate: AP −1.6 mm, ML±1.0 mm, DV −5.7 mm. For the feeding behavior test, AAV encoding Cre or mCherry under CaMKII promoter (both from Penn Vector Core, total volume of 120 nl) was injected into the bilateral LH at the following coordinate: AP −1.6 mm; ML±1.0 mm; DV −5.7 mm. All viral vector titers were in the range of $2\text{-}9\times10^{13}$ genome copies (GC) per mL. Experiments were performed at least 2-4 weeks after virus injection.

Implantation of Sleeve and Optical Fiber(s)

For optical stimulation of LH, a mating sleeve to be connected to the patch cable was implanted above the skull midline at AP=−1.6 mm. For in vivo comparison of SSFO and SOUL in MD, a 400 μm diameter optic fiber (Doric lenses, Quebec, Canada) was embedded centrally above the skull midline at AP −1.4 mm to deliver the transcranial stimulation and 200 μm diameter fibers equipped with a 45 degree mirror tip were bilaterally implanted adjacent to the electrode arrays for direct stimulation of MD thalamus in each hemisphere separately. For the analysis of microglia activity in response to fiber implantation, an optic fiber was implanted into the cortex at the following coordinates: AP+1.6 mm, ML 1.0 mm, DV −0.5 mm. Mice had at least 2 weeks to recover after surgery.

In Vivo Electrophysiology in Mice

For multi-electrode array construction and implantation, custom multi-electrode array scaffolds (drive bodies) were designed using 3D CAD software (SolidWorks) and printed in Accura 55 plastic (American Precision Prototyping) as described previously (Brunetti et al., 2014; Liang et al., 2017). Prior to implantation, each array scaffold was loaded with 16-24 independently movable micro-drives carrying 12.5 μm nichrome (California Fine Wire Company) tetrodes. Electrodes were pinned to custom-designed 96- or 128-channel electrode interface boards (EIB, Sunstone Circuits) along with a common reference wire (A-M systems). For surgical implantation, after the preparation procedure similar to that of virus injection, an incision in the skin allowed access to the skull. Two ~1.2×1.6 mm craniotomies were drilled centered at (in mm from Bregma) AP −1.2, ML ±0.5. The dura was carefully removed, and the drive implant was lowered into the craniotomy using a stereotactic arm until the shortest tetrodes touched the cortical surface. Surgilube (Savage Laboratories) was applied around electrodes to guard against fixation through dental cement. Stainless-steel screws were implanted into the skull to provide electrical and mechanical stability and the entire array was secured to the skull using dental cement. The skin was subsequently closed with Vetbond and the animal was allowed to recover on a heating blanket. For electrophysiological recordings and spike sorting, signals were acquired using a Neuralynx multiplexing digital recording system (Neuralynx) through a combination of 32-channel and 64-channel digital multiplexing head stages plugged into the EIB of the implant. Signals from each electrode were amplified, filtered between 0.1 Hz and 9 kHz, and digitized at 30 kHz. Spike sorting was done automatically using MountainSort. Following sorting each cluster was manually inspected for quality. Clusters with spike waveforms that were symmetrical around their peak, indicative of an electrical noise signal, or showed inter-spike interval (ISI) distributions with more than 1% spikes<1 ms, indication of potential noise or multi-unit contamination, were excluded. For analysis of firing rate, changes in firing rate associated with optical stimulation were assessed using peri-stimulus time histograms (PSTHs). PSTHs were computed using a 1-ms bin width for individual neurons in each recording session convolved with a Gaussian kernel (30 ms variance) to create a spike density function (SDF) and the difference between baseline (200 ms before laser) and during laser was computed.

c-Fos Expression Under Dark and Ambient Light

For checking the c-fos expression in dark, mice were taken from the animal facility before the light on and perfused under the red light with PBS and 4% PFA. For checking the c-fos expression in laboratory ambient light, mice were taken from the animal facility 4 hours after the light on and perfused with PBS and 4% PFA. Brains were dissected out and sliced in 50 m-thickness slices with vibratome (Leica VT1000S). The light intensity was measured using light meter (Fisher Scientific). The c-fos antibody was used (Cell Signaling Technology, #2250 1:500) to perform the immunostaining and images were taken using confocal microscope (FV1000, Olympus).

Histology, Immunohistochemistry, and Microscopy

Mice were deeply anesthetized with isoflurane and transcardially perfused with cold phosphate-buffered saline (PBS), followed by ice-cold 4% paraformaldehyde (PFA; Sigma) in PBS. Brains were removed and submerged in 4% PFA at 4° C. overnight for post-fixation. Brains were sectioned using a vibratome (Leica VT100S) or transferred to 30% sucrose to equilibrate for sectioning with a cryostat microtome (Lecia CM1950, Germany). 60-100 μm sections were obtained. For immunostaining of PV, RFP, 2A peptide, c-Fos and lba-1, free-floating sections were sequentially washed with PBS, 0.5% Triton-100 in PBS (2 h at room temperature), and blocking solution (0.2% Triton-100, 5% Bovine serum albumin, and 15% normal goat serum in PBS, 1 h at room temperature). Sections were then incubated in primary antiserum (rabbit anti-c-Fos, 1:1000, SC-52, Santa Cruz Biotechnology; rabbit anti-RFP, 1:1000, 600-401-379, Rockland; rabbit anti-PV, 1:5000, PV-27, Swant; rabbit anti-lba-1, 1:1000, LAP0868, Wako; rabbit anti-2A peptide, 1:1000, ABS31, Millipore) diluted in blocking solution for 12-48 hours. After washing 3 times with 0.2% Triton in PBS, the sections were incubated with secondary antibodies (Alexa Fluor 647 or 555 goat anti-rabbit, both 1:500, Invitrogen) overnight at 4° C. Slices were then washed with 0.3 μmol DAPI in PBS for 20 min, twice with 0.1% Tween-20 in PBS for 15 min, and once with PBS for 20 min. For immunostaining of ChAT (choline acetyltransferase), the above procedure was followed, except that PBS was replaced with 0.1M Tris (PH=7.6). The primary antibody was goat anti-ChAT (1:200, AB144p, Millipore) and the secondary antibody was Alexa Fluor 647 donkey anti-goat (1:500, Invitrogen). Donkey serum was used instead of goat serum.

After staining, sections were mounted with Fluoro-Gel mounting medium with Tris buffer (50-247-04, Electron Microscopy Sciences). Widefield epifluorescence images were capture by an Olympus BX61 microscope equipped with 4×, 10×, 20×, and 60× objectives, a PRIOR ProScan III motorized stage (Prior Scientific Instruments, UK) and CellSens Dimension 1.11 stitching software (Olympus). For the PV-tdTomato or ChAT-tdTomato co-expression analysis, sections from three mice were imaged using an Olympus Fluoview FV1000 confocal microscope with a 20× lens. The maximum projection of z-stacks of three high-power fields (approximately 200 cells per region) was counted manually with ImageJ (Schindelin et al., 2012). For the optical stimulation-evoked c-Fos staining experiments in LH, mice were sacrificed 1.5 hr post blue light stimulation (60 s, 50 mW of 473 nm light delivered via a patch cable connected to a 473 nm diode-pumped solid-state (DPSS) laser, Ultralaser). To test whether the transcranial illuminations led to the activation in the visual system, the blue light transcranial illumination (60 s, 50 mW of 473 nm light delivered via a patch cable connected to a 473 nm DPSS laser, UltraLasers) was followed by an orange light transcranial illumination (100 s, 25 mW of 589 nm light delivered via the same patch cable with the laser end disconnected from the 473 nm laser and reconnected to a 589 nm DPSS laser, UltraLasers) 10 minutes later. 1.5 hr later, the mice were sacrificed. Brain samples were then subjected to c-Fos staining. Images taken were then overlaid with The Mouse Brain in Stereotaxic Coordinates (Paxinos and Franklin, 2004) to locate the LH, dLGN, or V1, and the c-Fos-positive neurons were manually counted by an individual experimenter blind to the experimental groups.

Feeding Behavior Assays

The day prior to testing, CaMKII::SOUL and control mice were placed on the food restriction schedule described above. On the test day, they were placed in a 16"×16" arena with two 2.75" side hexagonal plastic cups placed in contralateral corners. One cup contained standard chow, while the other cup contained no food. Each cup's location was randomized for each animal. Mice then were run through two consecutive sessions: 10 min post-activation session after blue light stimulation (60 s, 50 mW of 473 nm light delivered via a patch cable connected to a 473 nm DPSS laser, UltraLasers), and 10 min post-deactivation session after orange light illumination (100 s, 25 mW of 589 nm light delivered via the same patch cable with the laser end disconnected from the 473 nm laser and reconnected to a 589 nm DPSS laser, UltraLasers) for a total of a 20 min session. Food intake was manually quantified by weighing the amount of food left in the food chamber before vs. after each session. For blinding purposes, all mice used for behavioral experiments were given a unique numerical identifier. Images of the brain sections ±0.5 mm around the LH were taken and then were overlaid with The Mouse Brain in Stereotaxic Coordinates (Paxinos and Franklin, 2004) to locate the LH. Tdtomato fluorescence was used to determine the actual SOUL-1003 expressing region. If the LHs did not have the tdTomato fluorescence or the observed 1004 tomato fluorescence was beyond the region of LH, mice were retroactively excluded from the data set.

Use of SOUL in Parkinson's Disease (PD) Model Mice

The $AAV_9$-EF1α-DIO-SOUL-tdTomato construct was prepared and packaged at the Boston Children's Hospital Viral Core ($1\times10^{13}$ GC $ml^{-1}$ viral titer). For SOUL-mediated stimulation experiments, optic fibers were connected to a 473 nm blue laser for activation and a 600 nm orange laser for inactivation. Laser power was adjusted to 10-15 mW before each experiment. For the forced swim and tail suspension tests, SOUL in PF thalamus was activated using a 60 s blue laser light source (activation) connected to the skull just before the start of the experiment. The optic fiber was then disconnected, and following the completion of the behavior, mice were reconnected via optic fibers to a 90 s orange laser light source (inactivation). For sucrose preference tests, SOUL in PF thalamus was activated similar to the forced swim and tail suspension tests, except that mice remained plugged in to the optic fibers for the entire duration of the behavior and SOUL activation was performed for 5 minutes, followed by 5 minutes of inactivation, repeated for the session.

Macaque Methods

Surgical Procedures

All surgical procedures were performed in a surgery room with aseptic conditions and under general anesthesia. A titanium head post was surgically implanted and fixed to the skull with titanium screws. The head post served to fix the head position during electrophysiological recordings. After recovery was complete, a subsequent surgery was performed to implant two circular cranial chambers over both lateral prefrontal cortices at locations that allowed access to the cortical surface between the arcuate and principal sulci. The chambers (24 mm outer diameter, 19 mm inner diameter) were made of carbon peek and were designed to fit the curvature of the skull at the implantation sites. A circular craniotomy 24 mm in diameter was performed at the target site of each chamber. The chambers perimeters were sealed to the skull using C&B Metabond (Parkell) and fixed with cranial titanium screws and a margin of radiopaque bone cement (Zimmer Surgical, Inc.). The chamber on the left hemisphere had a height of 19 mm above the skull surface. The chamber on the right hemisphere had a height of 5 mm above the skull surface and was custom-designed to facilitate the performance of an initial durotomy and subsequent durotomies upon dura regrowth. A 10 mm tall screwable adaptor chamber was added to this chamber to allow mounting electrophysiological recording towers. On the right hemisphere, the native dura was replaced with an artificial dura made of silicone (Shin-Etsu Inc.) and fabricated using a metallic mold. The hat-shaped dura consisted of a disc 28 mm in diameter and 450 m thick topped by a ring 19 mm in diameter and 2.8 mm tall (FIG. 17). The artificial dura was transparent, allowing daily visualization of the cortical surface as well as optical stimulation with a laser located outside the dura. Its self-sealing properties prevented the dura from ripping during penetration with electrophysiological probes and with 31G needles during virus injections. The artificial dura was implanted during the same surgery as the chambers. After the craniotomy and before chamber implantation, a durotomy 19 mm in diameter was performed on the right side. The artificial dura was then implanted so that its outer edge was under the native dura around the entire circumference of the durotomy. The chamber was subsequently implanted so that the ring-like portion of the artificial dura sat against the inner wall of the chamber. The artificial dura methods and materials were partially based on those reported in Ruiz et al., 2013 (Ruiz et al., 2013).

Anatomical Localization of Recording Sites

Plastic grids were fabricated with 500 μm holes separated by 1 mm. Each grid fit inside each chamber in one orientation. The grid holes served to guide the location of virus injection needles and electrophysiological probes. After cranial implantation, the holes were filled with a solution of 1% Agarose and 0.5% Gadolinium—a contrast agent used to increase the visibility of the grid holes in the MRI scan. The plastic grids were then placed inside the two implanted chambers and an MRI scan was performed. In the resulting images, the trajectory of each grid hole was projected until it intersected the cortex. This allowed determining the cortical location of virus injections and electrophysiological recordings corresponding to each grid hole.

Virus Injections

For macaque experiments, plasmids were used for AAV2/9 viruses encoding hSyn-SOUL-p2A-tdTomato, produced by Boston Children's Hospital Viral Core. The titer was 5×1013 genome copies per mL (gc/mL). Virus injections were made with a 31G needle with its shank embedded into a 23G needle for reinforcement. The needle was mounted on a microdrive tower (NAN Instruments) and was connected to a 100 μm Hamilton syringe via a polyethylene tube. The syringe was mounted on a syringe pump (Harvard Apparatus). After sealing and gluing the syringe, tube and needle, these were back loaded with silicone oil (Sigma) up to the needle tip until no air bubbles were present. Virus injections were performed in a surgery room with aseptic conditions and under general anesthesia. Once the animal was prepared for injections and mounted on a stereotaxic machine, the virus was removed from an ice box, thawed and loaded into the syringe from the needle tip. Injections were made at 3 penetration locations in the left lateral prefrontal cortex, at the dorsal lip of the principal sulcus. At each penetration location, the needle was inserted 6 mm below the dura surface, and injected a total of 7.2 μL at a rate of 1 μL/min at steps of 1.6 or 0.8 μL, retrieving the needle at steps of 1 or 0.5 mm, respectively. This resulted in a total of 21.6 μL injected over 42 sites across all 3 penetrations. On the same day, an equivalent procedure was also performed on the right lateral prefrontal cortex through the artificial dura. On subsequent days, the animal was brought to the lab for chamber cleaning and maintenance. To determine the onset and state of virus expression over time, tdTomato fluorescence was monitored by illuminating the cortex on the artificial dura chamber with green light (510-540 nm) and visualizing and registering images of the cortical surface through a 600 nm long-pass glass filter (FIG. 17). The extent of expression on the cortical surface was determined by thresholding the fluorescence image intensity. The thresholded region was outlined and its surface area of 28 mm2 was measured. The mean radius of expression was estimated by measuring distances between each injection location and the most proximal edge of the expression region, and averaged across the three locations. An estimate of the total expression volume in each prefrontal hemisphere (140 mm3) was obtained by calculating the volume inside a solid prism with the expression area as the base and the range of injection depths as the height.

Electrophysiological Recordings

Electrophysiological signals were recorded from sites in the left lateral prefrontal cortex within the superficial cortical region where virus injections were performed. This region included locations with a maximum distance of 1 mm away from any of the 3 injection sites, ranging 2 mm along the rostral-caudal axis, and 2 mm along the dorsal-ventral axis. Signals were acquired with a 16 or 32-contact linear probe (V-probe, Plexon Inc.) with a distance of 150 or 100 μm between contacts, respectively. The probe was held and micromanipulated with a computer-controlled microdrive tower (NAN Instruments Ltd., Israel) and embedded in a 23G guide tube held by a manually-manipulated holder from the same tower. The guide tube was lowered until its tip penetrated the dura, and the probe was lowered through the guide tube into the cortex. In a few sessions, the same procedure was performed on the right lateral prefrontal cortex, where the artificial dura was implanted. In these sessions, a blunt guide tube was used and lowered in to touch the artificial dura; the probe was then lowered through the guide tube to penetrate the artificial dura before being lowered into the cortex. In each recording session, the monkey sat in a custom non-human primate plexiglass chair and, at the lab, was head-fixed to the chair with a head post holder. The microdrive tower was affixed to the monkey's chamber. The guide tube was first lowered to perforate the dura, and the probe was then lowered through the guide tube into the cortex until clear neuronal spike waveforms were observed in the electrophysiological signals of several probe contacts. The cortical depth of each contact was estimated based on the distance of that contact to the probe tip and on the penetration depth of the probe tip, accounting for the dura thickness (Galashan et al., 2011). The depth of all contacts across all recorded sessions ranged up to 5.6 mm from the cortical surface. Once the probe was positioned, a step-index optical fiber (Thorlabs Inc., 0.2 mm diameter, 0.22 numerical aperture) held by a separate microdrive tower was placed with its tip between 4 and 10 mm above the cortical surface so that the laser would illuminate a region between 1.8 and 4.4 mm in diameter encompassing the recording site (surface area between 2.43 and 15.5 mm2). Notice that this region was smaller than the total region of opsin expression. The fiber was connected interchangeably to two DPSS lasers (blue, 473 nm; orange, 589 nm). Across sessions, the laser light power density at the dura surface was varied between 12 and 173 mW/mm2 (mean of 94 mW/mm2; mean total power of 558 mW). Within this range, there was no relationship between the power density in each session and the resulting percentage of significantly modulated units. Once the optical fiber and probe were positioned, the bottom half of the chamber was filled with saline. This helped buffer the temperature at the dura surface during light stimulation. The top of the chamber was completely sealed with a film of black electrical tape, which ensured that no laser light escaped the chamber. Each recording lasted approximately 60 to 80 minutes and consisted of 16 to 22 consecutive trials of 3.5 minutes each. In each trial, 30s of baseline activity was recorded and 10 s of blue light was then delivered; after an interval of 2 min (post-blue period), 20s of orange light was delivered, after which an additional 30 s before the next trial (post-orange period) was recorded. Both colors of light were delivered through the same fiber. To accomplish this, the optical fiber end connected to the laser was quickly switched between the blue and orange lasers during the periods between stimulation of each trial. Electrophysiological signals were digitized by a digital head stage, amplified by a Front-End Amplifier and received and saved by a Cerebus Neural Signal Processor (Blackrock Microsystems). The voltage signals from each probe contact were high-pass filtered at 250 Hz, and then thresholded in order to extract spike waveforms. The waveforms were then sorted into multiunits and single neurons using Plexon Offline Sorter software, and all spike timestamps were obtained for each unit. To extract local field potential, the signals were sampled at 1 kHz and low-pass filtered at 250 Hz. To measure potential temperature changes inside the cortex due to light stimulation through the native dura, a hypodermic needle probe (Omega Engineering, Inc.) was implanted into lateral prefrontal cortex through a guide tube, as with the electrophysiological probe. The light stimulation paradigm used in the neuronal recording sessions was replicated and temperature measurements over time with 1 Hz sampling using a Digi-Sense thermocouple thermometer (Cole Parmer Instrument Company) were acquired. Measurements were repeated with the temperature probe placed at different depths between the surface and 3 mm inside the cortex.

Data Analysis

Figure 6B:
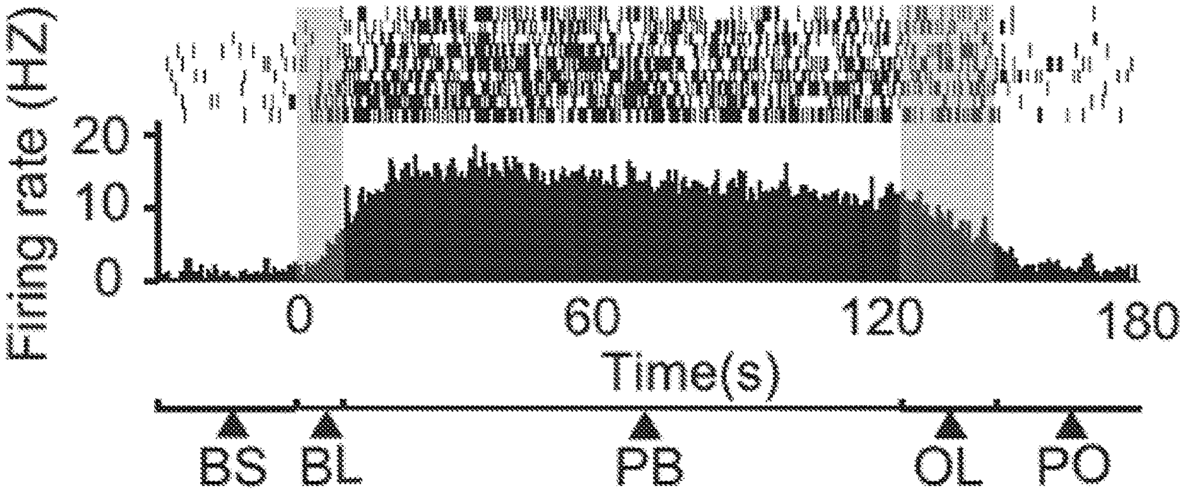
Figure 6C:
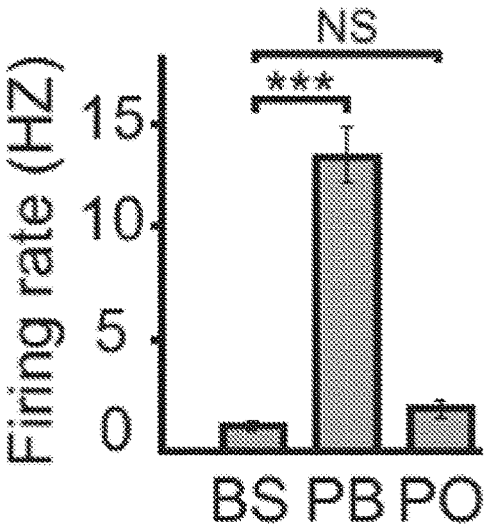
Figure 6D:
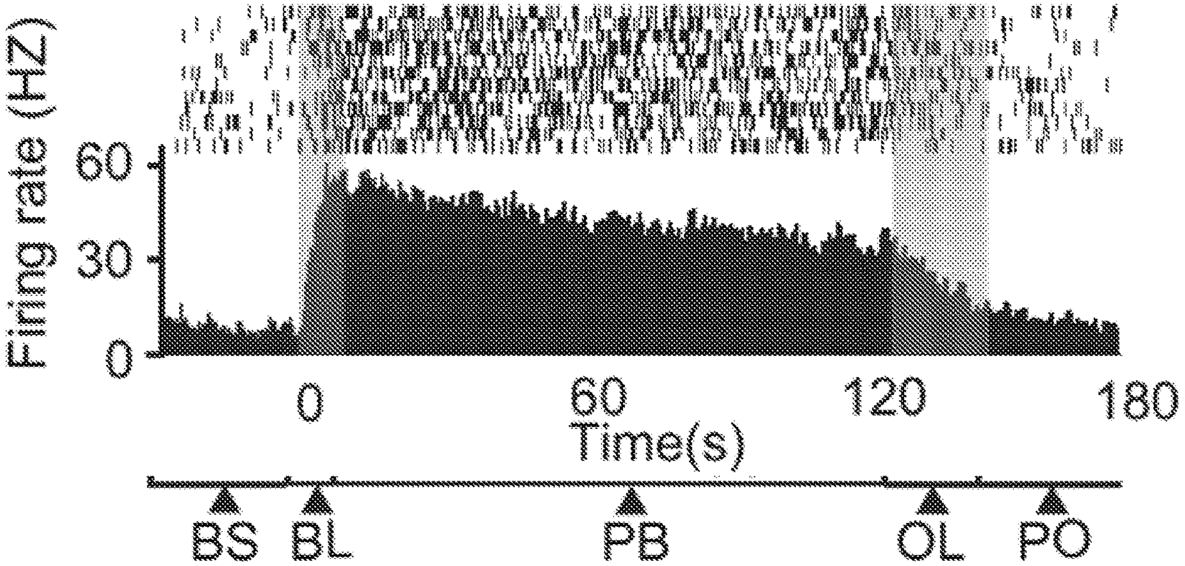
Figure 6E:
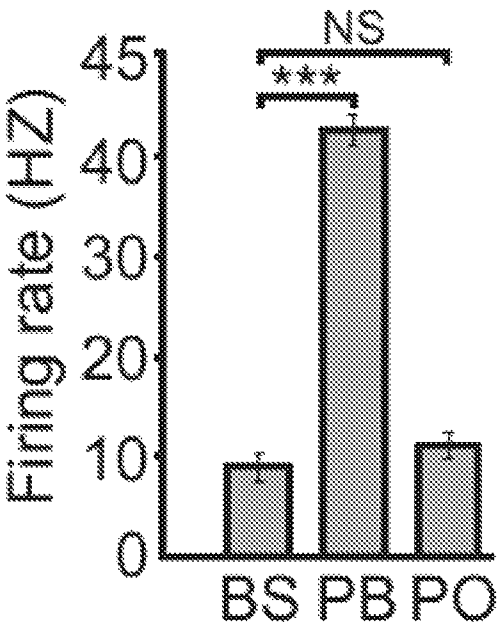
Figure 6F:
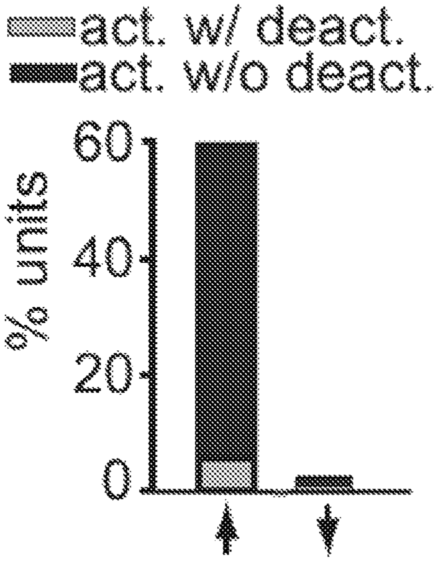
Figure 6G:
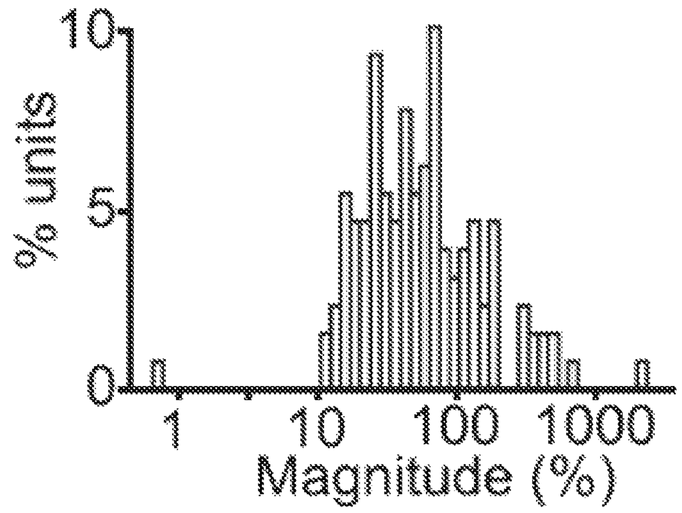
Figure 6H:
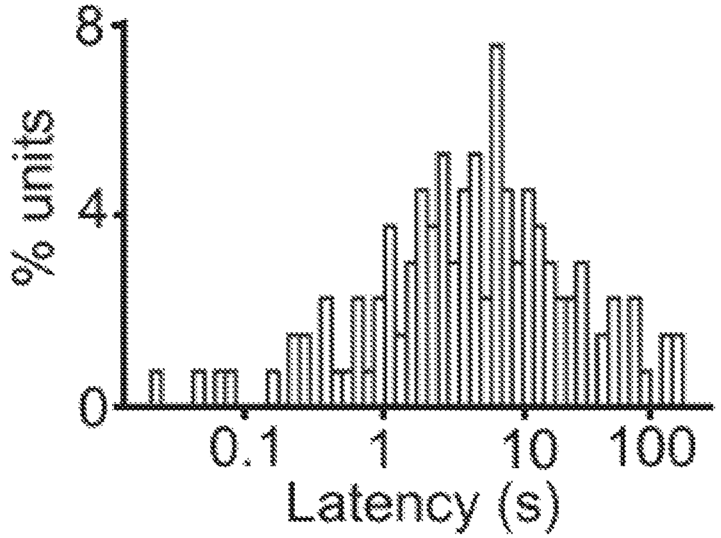
Figure 6I:
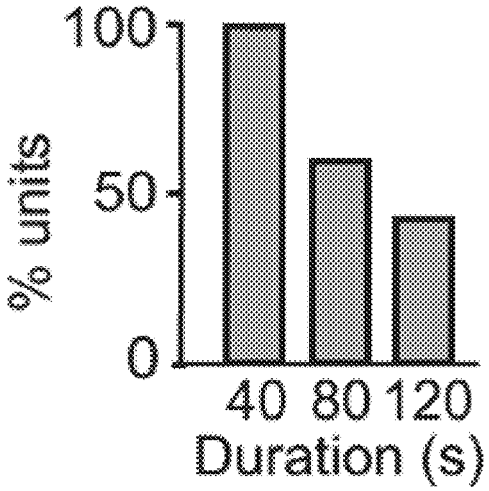
Figure 6J:
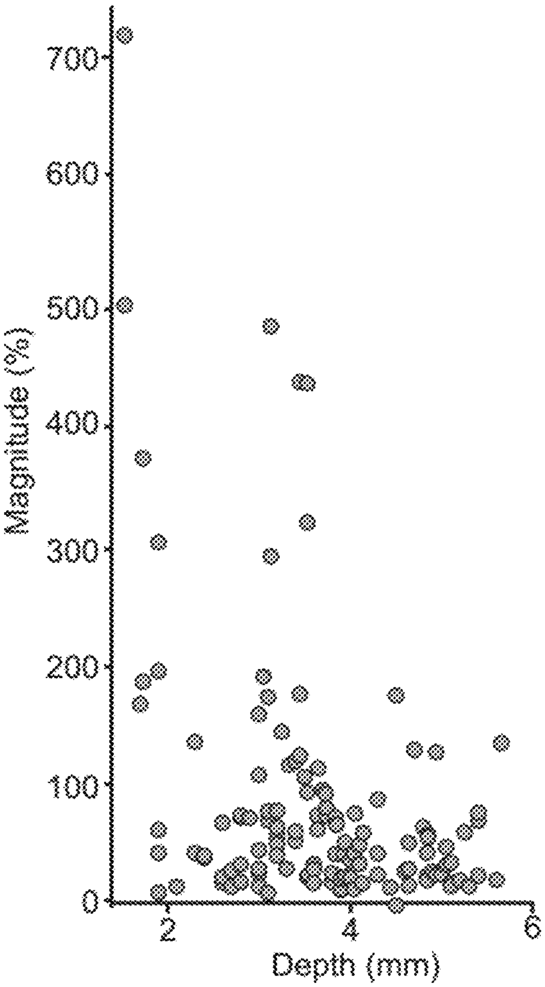
Figure 6K:
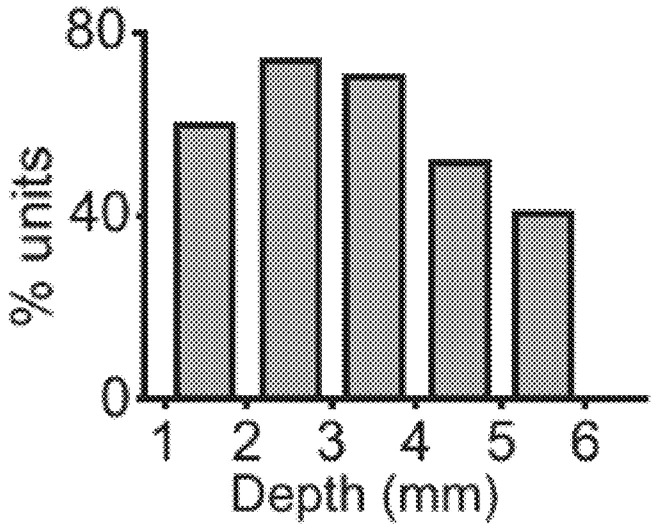

For each single unit and multiunit recorded, the spike timestamps were used to compute the mean firing rate in each 1-s time bin over each entire trial and averaged the time course across trials (FIGS. 6B and 6D). For each of the five trial periods (baseline, blue laser, post-blue, orange laser and post-orange), the mean firing rate across the period in each trial, as well as the mean across trials was computed. To assess whether each unit's firing rate was significantly modulated in the post-blue period, this period was subdivided into three 40 s sub-periods and used paired-sample t-tests to compare the firing rate between baseline and each sub-period. Units were then classified by the duration of the effect based on the number of 40s sub-periods with a significant modulation (FIG. 6I). For significantly modulated units, it was then tested whether the firing rate was restored to baseline levels following orange light stimulation by comparing the mean firing rates in the post-orange and baseline periods using paired-sample t-tests. For each modulated unit, the optogenetic modulation magnitude M (FIG. 6G) was measured as the percent change in firing rate from baseline: M=(FRPB−FRBA)/FRBA, where FRBA is the firing rates in the baseline period and FRPB is the mean firing rate across all significant post-blue sub-periods. The latency of the modulation (FIG. 6H) was estimated by performing the following analysis on each modulated unit: the mean firing rate across trials for each 5-ms time bin was first calculated, and the standard deviation across all 6000 time bins of the baseline period (SDBA) was then computed; the latency was estimated as the time between blue laser onset and the earliest occurrence of 2 consecutive time bins with firing rate exceeding 3*SDBA. Local Field Potentials (LFPs) were analyzed to determine whether oscillatory activity was modulated by SOUL activation. For each individual channel (corresponding to a recording contact in the probe), a time-frequency decomposition using the Fieldtrip data analysis toolbox (Oostenveld et al., 2011) was computed.

The multitaper method (option 'mtconvol') with 4 Hz spectral smoothing to estimate power in 1 Hz intervals from 1 to 250 Hz and at non-overlapping 1 second time intervals. The power from 30 seconds prior to blue laser onset to 27 seconds was calculated after the orange laser offset. Each window of analysis consisted of 1 second of data, giving a frequency resolution of 1 Hz. Two sessions were excluded from further analysis due to excessive high frequency noise, giving a total of 160 channels for LFP analysis. For each individual trial, the power during all trial periods was normalized by the power in the baseline period of that trial. This provided a measure of the percentage change in power elicited by the laser with respect to baseline. For each channel, it was then assessed whether there was significant power modulation by using a non-parametric cluster-based randomization test (Maris and Oostenveld, 2006). The null hypothesis that power in the baseline and power in the laser and post-laser periods (hereafter referred to as the "activation" time period) were the same was then addressed. To this end, time-frequency power estimates between the baseline and activation periods were randomly exchanged, and for each randomization, percent power change over time with respect to baseline was calculated. Therefore, the variable that was randomized was whether a power estimate at a given time and frequency occurred during the activation (laser and post-laser) time period vs. the pre-laser baseline. The largest cluster (continuous tiles in time-frequency space) to pass a first level significance threshold of 20% increase in power from baseline was extracted. This randomization was performed 10,000 times. The empirically observed clusters that deviated by 20% or more power were compared to this randomization distribution to assess significance at $\alpha=0.05$, adjusted for multiple comparisons across channels (N=160). There was large heterogeneity of effects across channels in the presented dataset, which precluded a meaningful average of the time-frequency power modulation. Instead, significance was assessed on an individual channel level, and therefore conducted 160 independent statistical tests (10 sessions×16 channels per probe). A two-sided test was used, considering a priori that activation could either cause increases or decreases in power from baseline. Therefore, to determine significance, a corrected p-value of 0.05/(160 channels*2 for increases/decreases) was used. Once significance on a per-channel level was determined, this was used to calculate the percentage of significantly modulated channels as a function of frequency (FIG. 7D—after smoothing the spectrum +/−7 Hz). The result revealed peaks at several frequencies. The Matlab function findpeaks was used to determine the center and widths for these peaks. Only peaks with a peak height above the mean of the probability spectrum in the 180-250 Hz range, a range which was assumed to contain no oscillatory structure, were considered. This revealed 4 peak frequency bands, which have been labeled as alpha/theta, and gamma 1-3. The center frequency and full width at half the peak height were used for the subsequent analyses (FIGS. 7E to 7G).

For each of the 4 bands, the magnitude of optogenetic modulation of power was calculated by averaging the baseline normalized power spectrum over all frequencies comprising each band; the magnitude mean and standard error across all channels (FIG. 7E) were calculated. Power modulation latency (FIG. 7F) was calculated by taking, for each channel where power was significantly modulated at a particular band, the first time point of the significant time-frequency cluster (provided that cluster contained the respective frequency band). For each channel with significant modulation at a particular frequency, the duration of power modulation (FIG. 7G) was assessed by taking the total duration of the significant time-frequency cluster. For latency and duration, mean and SEM was calculated across all channels having a significant effect in the frequency band of interest.

Quantification and Statistical Analysis

The number of biological replicates in mouse experiments in each group was 7-36 neurons per group for in vitro and ex vivo electrophysiology; 31-36 neurons per group from 2 mice for in vivo recording; 3-5 mice per group for immunohistology; and 4 mice per group for behavior. For macaque experiments in this study, the number of biological replicates was 128-215 units and 176 channels for LFP from one macaque. These numbers were based on previously published studies (Anikeeva et al., 2012; Diester et al., 2011). All statistics were performed in Graph Pad Prism (GraphPad Software, Inc.), unless otherwise indicated. Paired t-test, unpaired t-test, one-way ANOVA, two-way ANOVA, Wilcoxon Signed Rank Tests and cluster-based randomization test were used when appropriate. Bonferroni post hoc comparisons was conducted to detect significant main effects or interactions. In all statistical measures a P value<0.05 was considered statistically significant and it was set as *P<0.05, P<0.01, *P<0.001 and ****P<0.0001; all statistical tests used are indicated in the figure legends.

As described herein, SOUL, a new step-function opsin with ultra-high light sensitivity, was engineered to include a triple mutation (e.g., C128S, D156A, and T159C) to provide a minimally invasive optogenetic tool. The step-function opsin family was chosen as the parental base due to their enhanced capability for photointegration (Mattis et al., 2011), which allows them to be activated by the accumulation of low-intensity light over time. In addition, the new mutation (e.g., T159C) introduced to create SOUL further conveyed enhanced operational photosensitivity Without being bound by theory, it is believed that C128S and D156A mutations lead to step function opsin (e.g., long last opening of light sensitive channels), and that the addition of T159C to the C128S and D156A double mutant combination increases the current of the channel opening. However, the magnitude of the increased sensitivity generated by the triple mutant combination was completely unexpected. Advantageously, the long-lasting opening accumulates much larger current over time, thus very little light is needed to have enough current over time. This was confirmed in a series of experiments comparing the properties of SOUL to those of its parental opsin, SSFO. Taking advantage of this unique photosensitivity, SOUL was able to be activated in the awake mouse brain by a brief pulse of transcranial optical stimulation, causing a long-lasting increase in neuronal spiking activity even in the deepest regions of the mouse brain. While previous studies have developed various methods for noninvasive neuronal activation by optogenetics (Hira et al., 2009; Lin et al., 2013; Tanaka et al., 2012), the results described herein are the first to demonstrate a method for activation of any mouse brain region independent of its location via transcranial opsin stimulation, due to SOUL's superior light sensitivity. The superior photosensitivity of SOUL allows several improvements in the application of optogenetics methods. The noninvasiveness of transcranial optogenetic stimulation conveys the advantage of minimizing the requirements for surgical procedures and avoiding physical and inflammatory damages of neural tissues. Furthermore, because SOUL can be activated by lower-power light, neural tissue heating by light delivery is minimized. In mouse behavioral experiments requiring perturbations of neural activity, optogenetics offers the advantage of higher temporal resolution, yet tissue damage is always a concern. And while chemogenetics is non-invasive, it has the drawback of low temporal resolution (Alexander et al., 2009; Armbruster et al., 2007). Optogenetic stimulation with SOUL offers a solution to both of these limitations, since it can produce reversible neural perturbations noninvasively, like chemogenetics, but with a much higher temporal resolution. In addition, SOUL can also be useful in longitudinal experiments requiring non-invasive perturbations of neuronal activity throughout the developmental stages of mice, since it does not require the chronic implantation of optical fibers in infants, which may lead to severe tissue damage and abnormal brain development. Moreover, SOUL is an ideal tool for experiments requiring activation of multiple brain areas (for instance, activation of left and right mouse LHs), since transcranial illumination can span the entire brain and can therefore activate any number of SOUL-expressing regions; this eliminates complications that arise from the insertion of multiple fibers.

Furthermore, once activated with blue light, SOUL remains in the open state for tens of minutes. Accordingly, the techniques herein make it possible to activate brain regions without the need for inserted/implanted optical fibers, thus facilitating experiments/treatments requiring animals/subjects to be disconnected from all equipment, particularly animals/subjects whose behaviors involve long-range movements.

Prior to the experiments presented in this application, a few studies have contributed in various ways to the development of non-invasive optogenetic stimulation methods (Chen et al., 2018; Hira et al., 2009; Prakash et al., 2012; Tanaka et al., 2012). ReaChR, a fast-cycling opsin, was shown to induce action potentials in mice using particular combinations of target regions and illumination regimes, i.e., activation in superficial regions (motor cortex) by illumination through the closed skull, or in the brainstem by illumination at the opening of the external auditory canal (Lin et al., 2013). Jaws, a recently reported red-shifted crux-halorhodopsin, mediates strong noninvasive neural inhibition in brain structures up to 3 mm deep (Chuong et al., 2014).

In addition to transcranial optogenetic stimulation in mice, the techniques herein also showed optogenetic activation of non-human primate (e.g., macaque monkey) cortical neurons with external illumination through a transparent artificial dura using SOUL. This method was first implemented by previous studies using other opsins (Nassi et al., 2015; Ruiz et al., 2013). Because an artificial dura provides optical access to the cortical surface, it allowed precise localization of the virus injections, electrodes and laser beams with respect to anatomical landmarks, as well as day-by-day visualization of the extent of virus expression on the cortical surface as indicated by epifluorescence. However, the prior art method has several disadvantages including additional surgical procedures for removal of the native dura, implantation of the artificial dura and increased risk of infection and inflammatory reactions. The working examples provided herein describe the results of experiments demonstrate important methodological advances that overcomes these problems, including: taking advantage of the superior photosensitivity of SOUL to enable optogenetic stimulation of the cortex of a non-human primate (e.g., macaque monkey) with external illumination through the intact dura. The methods presented herein offer many of the same benefits in macaques as they do in mice, including the prevention of tissue damage, infection and inflammation due to surgical invasiveness. The demonstration of transcranial optogenetic stimulation in mice raises the possibility of accomplishing the same in macaques. However, a major difference between these species is that the skull is much thinner in the mouse than in the macaque. This may be overcome using methods for skull thinning (Frostig et al., 1990; Schiessl and McLoughlin, 2003) or skull clearing (Zhao et al., 2018) in macaques, although this remains to be tested. In mice, optogenetic effects as deep as 5.5 to 6.2 mm were observed. In the macaque brain, neurons with significant SOUL-induced activation at all recorded depths, up to 5.6 mm were found. On the other hand, a gradual decrease in the proportions of modulated units and the magnitude of effects as a function of depth was observed. Deeper recording experiments may help clarify whether transdural SOUL stimulation can activate non-superficial brain regions such as subcortical structures.

Due to the use of external illumination, the techniques provided herein with respect to non-human primates (e.g., macaques) provide the ability to simultaneously activate neurons within a region of cortex on the scale of hundreds of squared millimeters, a magnitude or two larger than what can be achieved with internal illumination (Acker et al., 2016). Virus injections were performed in three cortical penetrations separated by approximately 2 mm, leading to an expression area of 28.4 mm2 and a volume of 140 mm3. However, the techniques herein provide the ability to activate a much larger volume of surface cortex within the cranial chamber by performing a larger number of injections and increasing the laser beam size. Perturbing activity on the scale of an entire functional region of cortex makes it possible to address more effectively the contribution of the specific functional region to a given brain process or behavior. To date, a major challenge faced by primate optogenetic studies has been the ability to obtain behavioral effects with a magnitude comparable to those observed in mice. This challenge may be due to the limits in the anatomical scale of primate optogenetic effects with internal illumination (Galvan et al., 2017). By increasing the spatial scale of the perturbation, external illumination method offers a putative solution to this challenge.

A few special factors may be taken into consideration to ensure the success of this large-scale optogenetic method. First, while the temperature measurements revealed no systematic temperature increases in the brain with the laser power levels used here, the need to increase the total power to illuminate larger regions could lead to more heating around the illuminated area. Additional tests may measure temperature changes during illumination of larger cortical surfaces, and their potential short-term and long-term effects on the brain, and to help develop cooling methods to prevent such effects if necessary. Second, with the use of higher levels of total light power, it becomes particularly important to ensure that the chamber is completely light-sealed to prevent the laser light from reaching the exterior and causing visually-driven activation of neurons; such confounder, however, is partly controlled for by the fact that the step-function opsin activates neurons beyond the period of optical stimulation. Third, while the working examples provided herein used step-index fibers to maximize the even spread of light across the cortical surface, light scattering might result in an uneven distribution of light, particularly at the beam edges. To prevent this effect at the edges of targeted region, it may be necessary to extend the beam size slightly beyond these edges. Lastly, for large-scale activation of deeper structures of the primate brain, the techniques herein may be modified to ensure that the appropriate amount and spread of light power is provided, accounting for light scattering.

The techniques herein also demonstrated that optogenetically inducing an activated state in prefrontal cortex via SOUL caused neurons to synchronize their activity and generate oscillatory patterns in the LFPs. These oscillations were expressed in both low (theta/alpha) and high (gamma) frequency bands. While the data herein does not clearly determine why SOUL-mediated activation leads to the generation of oscillatory patterns, without being bound by theory, it is believed that a long, sustained increase in the activity of a cortical circuit may be sufficient for neurons to engage in massive synchronization that leads to the emergence of rhythmic activity. While the power modulation was much larger in the theta/alpha frequency range than in the gamma range, there was an inverse relationship between band frequency and modulation latency, with the highest gamma modulation appearing first (an average of 12.4 s after the appearance of the spiking modulation) and the theta/alpha modulation appearing last. This suggests that upon increases in cortical activity, it takes longer for neurons to synchronize their activity into lower-frequency rhythms than high-frequency ones. Why lower-frequency oscillations in the theta/alpha range show such a late onset remains to be determined. Theta and gamma rhythms have previously been related to multiple brain functions, including feedforward information flow, working memory maintenance, decision making, sleep, and visual attention (Dzirasa et al., 2009; Fries, 2015; Schaich Borg et al., 2017). However, almost all of these studies have been correlational, since causal tests require experimentally inducing or perturbing specific oscillations in a systematic and controlled fashion—a major challenge to date.

The techniques herein provide new tools for induction of oscillations at theta and gamma frequencies, which may facilitate causal tests for their role in brain functions and disorders. These techniques offers important advantages. For example, the fact that the induced oscillations emerge following a 10 s square pulse of blue light and remain beyond this period means that they are not generated by rhythmic optical stimulation (Iaccarino et al., 2016), nor do they require the presence of optical stimulation to persist. Instead, they emerge as an intrinsic property of the network in response to activation. Additional studies with cell type-specific activation may help dissect the mechanisms underlying brain rhythms. Besides being a useful tool for understanding the mechanisms underlying certain neurological and psychiatric disorders in animal models, optogenetics also has the potential for clinical use in the treatment of such disorders in humans. Particularly, disorders caused by neuronal activity or neurotransmitter imbalance may be treated by restoring this imbalance using optogenetic stimulation. Examples of this are studies that have used optogenetics in mouse models to control symptoms of absence seizures (Sorokin et al., 2017) and autistic-like behaviors (Yizhar et al., 2011b), Parkinson's disease (Gradinaru et al., 2009) and stroke (Cheng et al., 2014).

Traditional neurological treatments such as deep brain stimulation, pharmacological intervention and surgical ablation are all known to have major side effects due to their limited specificity. Optogenetics, in contrast, allows neuronal manipulation with higher temporal and spatial specificity and has the potential for cell type-specific targeting (El-Shamayleh et al., 2017). However, several goals will need to be accomplished before optogenetics can be considered a viable treatment option (Williams and Denison, 2013): The first and most important will be to carefully evaluate the potential risks of trying such treatments in patients, especially risks associated with transfer and expression of the opsin genes (Frederic et al., 2014); second, to find solutions to excitotoxicity, which may affect the longevity of SOUL-expressing neurons due to undesirable intracellular acidification and/or mitochondria-mediated apoptosis (Maimon et al., 2018); third, to deliver an appropriate amount of light that is high enough to activate the opsin across an entire target region, but low enough to prevent noxious levels of heating; fourth, to ensure that the implanted optical device will cause minimal damage to the patients' brain. The advantageous properties of SOUL make it an excellent tool to accomplish many of these goals. Due to its superior photosensitivity, SOUL can activate a larger volume of cortex with minimal light power. This advantage will be essential, given that the regions to be targeted for treatment are larger than the regions of interest typically targeted in mouse and macaque optogenetic studies. To target superficial cortical regions, it may be possible to deliver light noninvasively from outside the cortical surface or, perhaps, even outside the dura, as shown here for the macaque. To target deeper regions, the higher photosensitivity of SOUL will also be advantageous in that despite the potential need for implantation of an optical fiber, the brain volume receiving enough light for SOUL activation will be larger. Due to these advantages, SOUL-based optogenetics may be explored for minimally invasive treatment for neurological and psychiatric disorders.

REFERENCES

Acker, L., Pino, E. N., Boyden, E. S., and Desimone, R. (2016). FEF inactivation with improved optogenetic methods. P Natl Acad Sci USA 113, E7297-E7306.

Alexander, G. M., Rogan, S. C., Abbas, A. I., Armbruster, B. N., Pei, Y., Allen, J. A., Nonneman, R. J., Hartmann, J., Moy, S. S., Nicolelis, M. A., et al. (2009). Remote Control of Neuronal Activity in Transgenic Mice Expressing Evolved G Protein-Coupled Receptors. Neuron 63, 27-39.

Anikeeva, P., Andalman, A. S., Witten, I., Warden, M., Goshen, I., Grosenick, L., Gunaydin, L. A., Frank, L. M., and Deisseroth, K. (2012). Optetrode: a multichannel readout for optogenetic control in freely moving mice. Nature neuroscience 15, 163-U204.

Aravanis, A. M., Wang, L. P., Zhang, F., Meltzer, L. A., Mogri, M. Z., Schneider, M. B., and Deisseroth, K. (2007). An optical neural interface: in vivo control of rodent motor cortex with integrated fiberoptic and optogenetic technology. Journal of Neural Engineering 4, S143-S156.

Armbruster, B. N., Li, X., Pausch, M. H., Herlitze, S., and Roth, B. L. (2007). Evolving the lock to fit the key to create a family of G protein-coupled receptors potently activated by an inert ligand. P Natl Acad Sci USA 104, 5163-5168.

Bergs, A., Schultheis, C., Fischer, E., Tsunoda, S. P., Erbguth, K., Husson, S. J., Govorunova, E., Spudich, J. L., Nagel, G., Gottschalk, A., and Liewald, J. F. (2018). Rhodopsin optogenetic toolbox v2.0 for light-sensitive excitation and inhibition in *Caenorhabditis elegans*. Plos One 13.

Berndt, A., Schoenenberger, P., Mattis, J., Tye, K. M., Deisseroth, K., Hegemann, P., and Oertner, T. G. (2011). High-efficiency channelrhodopsins for fast neuronal stimulation at low light levels. P Natl Acad Sci USA 108, 7595-7600.

Berndt, A., Yizhar, O., Gunaydin, L. A., Hegemann, P., and Deisseroth, K. (2009). Bi-stable neural state switches. Nature Neuroscience 12, 229-234.

Boyden, E. S., Zhang, F., Bamberg, E., Nagel, G., and Deisseroth, K. (2005). Millisecond-timescale, genetically targeted optical control of neural activity. Nature neuroscience 8, 1263-1268.

Brunetti, P. M., Wimmer, R. D., Liang, L., Siegle, J. H., Voigts, J., Wilson, M., and Halassa, M. M. (2014). Design and Fabrication of Ultralight Weight, Adjustable Multi-electrode Probes for Electrophysiological Recordings in Mice. Jove-J Vis Exp.

Cavanaugh, J., Monosov, I. E., McAlonan, K., Berman, R., Smith, M. K., Cao, V., Wang, K. H., Boyden, E. S., and Wurtz, R. H. (2012). Optogenetic inactivation modifies monkey visuomotor behavior. Neuron 76, 901-907.

Chen, S., Weitemier, A. Z., Zeng, X., He, L. M., Wang, X. Y., Tao, Y. Q., Huang, A. J. Y., Hashimotodani, Y., Kano, M., Iwasaki, H., et al. (2018). Near-infrared deep brain stimulation via upconversion nanoparticle-mediated optogenetics. Science 359, 679-683.

Cheng, M. Y., Wang, E. H., Woodson, W. J., Wang, S., Sun, G. H., Lee, A. G., Arac, A., Fenno, L. E., Deisseroth, K., and Steinberg, G. K. (2014). Optogenetic neuronal stimulation promotes functional recovery after stroke. P Natl Acad Sci USA 111, 12913-12918.

Chow, B. Y., Han, X., Dobry, A. S., Qian, X., Chuong, A. S., Li, M., Henninger, M. A., Belfort, G. M., Lin, Y., Monahan, P. E., and Boyden, E. S. (2010). High-performance genetically targetable optical neural silencing by light-driven proton pumps. Nature 463, 98-102.

Chuong, A. S., Miri, M. L., Busskamp, V., Matthews, G. A. C., Acker, L. C., Sorensen, A. T., Young, A., Klapoetke, N.C., Henninger, M. A., Kodandaramaiah, S. B., et al. (2014). Noninvasive optical inhibition with a red-shifted microbial rhodopsin. Nature neuroscience 17, 1123-1129.

Dawydow, A., Gueta, R., Ljaschenko, D., Ullrich, S., Hermann, M., Ehmann, N., Gao, S., Fiala, A., Langenhan, T., Nagel, G., and Kittel, R. J. (2014). Channelrhodopsin-2-XXL, a powerful optogenetic tool for low-light applications. Proc Natl Acad Sci USA 111, 13972-13977.

Diester, I., Kaufman, M. T., Mogri, M., Pashaie, R., Goo, W., Yizhar, O., Ramakrishnan, C., Deisseroth, K., and Shenoy, K. V. (2011). An optogenetic toolbox designed for primates. Nature neuroscience 14, 387-397.

Dzirasa, K., and Lisanby, S. H. (2012). How does deep brain stimulation work? Biol Psychiatry 72, 892-894.

Dzirasa, K., Santos, L. M., Ribeiro, S., Stapleton, J., Gainetdinov, R. R., Caron, M. G., and Nicolelis, M. A. (2009). Persistent hyperdopaminergia decreases the peak frequency of hippocampal theta oscillations during quiet waking and REM sleep. Plos One 4, e5238.

El-Shamayleh, Y., Kojima, Y., Soetedjo, R., and Horwitz, G. D. (2017). Selective Optogenetic Control of Purkinje Cells in Monkey Cerebellum. Neuron 95, 51-62 e54.

Frederic, G., Alexander, R. H., and Robert, M. I. K. (2014). Controlling Brain Cells With Light: Ethical Considerations for Optogenetic Clinical Trials. AJOB Neuroscience, 3-11.

Fries, P. (2015). Rhythms for Cognition: Communication through Coherence. Neuron 88, 220-235.

Frostig, R. D., Lieke, E. E., Tso, D. Y., and Grinvald, A. (1990). Cortical Functional Architecture and Local Coupling between Neuronal-Activity and the Microcirculation Revealed by Invivo High-Resolution Optical Imaging of Intrinsic Signals. P Natl Acad Sci USA 87, 6082-6086.

Galvan, A., Caiola, M. J., and Albaugh, D. L. (2017). Advances in optogenetic and chemogenetic methods to study brain circuits in non-human primates. J Neural Transm (Vienna).

Gerits, A., and Vanduffel, W. (2013). Optogenetics in primates: a shining future? Trends Genet 29, 403-411.

Gradinaru, V., Mogri, M., Thompson, K. R., Henderson, J. M., and Deisseroth, K. (2009). Optical Deconstruction of Parkinsonian Neural Circuitry. Science 324, 354-359.

Han, X., Qian, X. F., Bernstein, J. G., Zhou, H. H., Franzesi, G. T., Stern, P., Bronson, R. T., Graybiel, A. M., Desimone, R., and Boyden, E. S. (2009). Millisecond-Timescale Optical Control of Neural Dynamics in the Nonhuman Primate Brain. Neuron 62, 191-198.

Hauss-Wegrzyniak, B., Lynch, M. A., Vraniak, P. D., and Wenk, G. L. (2002). Chronic brain inflammation results in cell loss in the entorhinal cortex and impaired LTP in perforant path-granule cell synapses. Exp Neurol 176, 336-341.

Hippenmeyer, S., Vrieseling, E., Sigrist, M., Portmann, T., Laengle, C., Ladle, D. R., and Arber, S. (2005). A developmental switch in the response of DRG neurons to ETS transcription factor signaling. Plos Biol 3, 878-890.

Hira, R., Honkura, N., Noguchi, J., Maruyama, Y., Augustine, G. J., Kasai, H., and Matsuzaki, M. (2009). Transcranial optogenetic stimulation for functional mapping of the motor cortex. Journal of Neuroscience Methods 179, 258-263.

Hososhima, S., Sakai, S., Ishizuka, T., and Yawo, H. (2015). Kinetic Evaluation of Photosensitivity in Bi-Stable Variants of Chimeric Channelrhodopsins. Plos One 10.

Iaccarino, H. F., Singer, A. C., Martorell, A. J., Rudenko, A., Gao, F., Gillingham, T. Z., Mathys, H., Seo, J., Kritskiy, O., Abdurrob, F., et al. (2016). Gamma frequency entrainment attenuates amyloid load and modifies microglia. Nature 540, 230-235.

Jennings, J. H., Rizzi, G., Stamatakis, A. M., Ung, R. L., and Stuber, G. D. (2013). The inhibitory circuit architecture of the lateral hypothalamus orchestrates feeding. Science 341, 1517-1521.

Kim, J. H., Lee, S. R., Li, L. H., Park, H. J., Park, J. H., Lee, K. Y., Kim, M. K., Shin, B. A., and Choi, S. Y. (2011). High cleavage efficiency of a 2A peptide derived from porcine teschovirus-1 in human cell lines, zebrafish and mice. Plos One 6, e18556.

Klapoetke, N.C., Murata, Y., Kim, S. S., Pulver, S. R., Birdsey-Benson, A., Cho, Y. K., Morimoto, T. K., Chuong, A. S., Carpenter, E. J., Tian, Z. J., et al. (2014). Independent optical excitation of distinct neural populations. Nature Methods 11, 338-U333.

Kleinlogel, S., Feldbauer, K., Dempski, R. E., Fotis, H., Wood, P. G., Bamann, C., and Bamberg, E. (2011). Ultra-light-sensitive and fast neuronal activation with the Ca(2)+-permeable channelrhodopsin CatCh. Nature neuroscience 14, 513-518.

Kreutzberg, G. W. (1996). Microglia: a sensor for pathological events in the CNS. Trends Neurosci 19, 312-318.

Liang, L., Oline, S. N., Kirk, J. C., Schmitt, L. I., Komorowski, R. W., Remondes, M., and Halassa, M. M. (2017). Scalable, Lightweight, Integrated and Quick-to-Assemble (SLIQ) Hyperdrives for Functional Circuit Dissection. Front Neural Circuit 11.

Lin, J. Y., Knutsen, P. M., Muller, A., Kleinfeld, D., and Tsien, R. Y. (2013). ReaChR: a red-shifted variant of channelrhodopsin enables deep transcranial optogenetic excitation. Nature neuroscience 16, 1499-508.

Lin, J. Y., Lin, M. Z., Steinbach, P., and Tsien, R. Y. (2009). Characterization of engineered channelrhodopsin variants with improved properties and kinetics. Biophys J 96, 1803-1814.

Luo, X. G., and Chen, S. D. (2012). The changing phenotype of microglia from homeostasis to disease. Transl Neurodegener 1, 9.

Madisen, L., Mao, T. Y., Koch, H., Zhuo, J. M., Berenyi, A., Fujisawa, S., Hsu, Y. W. A., Garcia, A. J., Gu, X., Zanella, S., et al. (2012). A toolbox of Cre-dependent optogenetic transgenic mice for light-induced activation and silencing. Nature neuroscience 15, 793-802.

Maimon, B. E., Diaz, M., Revol, E. C. M., Schneider, A. M., Leaker, B., Varela, C. E., Srinivasan, S., Weber, M. B., and Herr, H. M. (2018). Optogenetic Peripheral Nerve Immunogenicity. Sci Rep-Uk 8.

Mattis, J., Tye, K. M., Ferenczi, E. A., Ramakrishnan, C., O'Shea, D. J., Prakash, R., Gunaydin, L. A., Hyun, M., Fenno, L. E., Gradinaru, V., et al. (2011). Principles for applying optogenetic tools derived from direct comparative analysis of microbial opsins. Nat Methods 9, 159-172.

Nandy, A., Nassi, J. J., Jadi, M. P., and Reynolds, J. (2019). Optogenetically induced low-frequency correlations impair perception. Elife 8.

Nassi, J. J., Avery, M. C., Cetin, A. H., Roe, A. W., and Reynolds, J. H. (2015). Optogenetic Activation of Normalization in Alert Macaque Visual Cortex. Neuron 86, 1504-1517.

Nehme, R., Zuccaro, E., Ghosh, S. D., Li, C. C., Sherwood, J. L., Pietilainen, O., Barrett, L. E., Limone, F., Worringer, K. A., Kommineni, S., et al. (2018). Combining NGN2 Programming with Developmental Patterning Generates Human Excitatory Neurons with NMDAR-Mediated Synaptic Transmission. Cell Rep 23, 2509-2523.

Paxinos, G. (2000). The rhesus monkey brain in stereotaxic coordinates/George Paxinos, Xu-Feng Huang, Arthur Toga (San Diego, Calif.: Academic Press).

Paxinos, G., and Franklin, K. B. J. (2004). The mouse brain in stereotaxic coordinates, Compact 2nd edn (Amsterdam; Boston: Elsevier Academic Press).

Polikov, V. S., Tresco, P. A., and Reichert, W. M. (2005). Response of brain tissue to chronically implanted neural electrodes. J Neurosci Methods 148, 1-18.

Prakash, R., Yizhar, O., Grewe, B., Ramakrishnan, C., Wang, N., Goshen, I., Packer, A. M., Peterka, D. S., Yuste, R., Schnitzer, M. J., and Deisseroth, K. (2012). Two-photon optogenetic toolbox for fast inhibition, excitation and bistable modulation. Nature Methods 9, 1171-Ul 132.

Rossi, J., Balthasar, N., Olson, D., Scott, M., Berglund, E., Lee, C. E., Choi, M. J., Lauzon, D., Lowell, B. B., and Elmquist, J. K. (2011). Melanocortin-4 Receptors Expressed by Cholinergic Neurons Regulate Energy Balance and Glucose Homeostasis. Cell Metab 13, 195-204.

Ruiz, O., Lustig, B. R., Nassi, J. J., Cetin, A., Reynolds, J. H., Albright, T. D., Callaway, E. M., Stoner, G. R., and Roe, A. W. (2013). Optogenetics through windows on the brain in the nonhuman primate. J Neurophysiol 110, 1455-1467.

Schaich Borg, J., Srivastava, S., Lin, L., Heffner, J., Dunson, D., Dzirasa, K., and de Lecea, L. (2017). Rat intersubjective decisions are encoded by frequency-specific oscillatory contexts. Brain Behav 7, e00710.

Schiessl, I., and McLoughlin, N. (2003). Optical imaging of the retinotopic organization of V1 in the common marmoset. Neuroimage 20, 1857-1864.

Schindelin, J., Arganda-Carreras, I., Frise, E., Kaynig, V., Longair, M., Pietzsch, T., Preibisch, S., Rueden, C., Saalfeld, S., Schmid, B., et al. (2012). Fiji: an open-source platform for biological-image analysis. Nature Methods 9, 676-682.

Selimbeyoglu, A., Kim, C. K., Inoue, M., Lee, S. Y., Hong, A. S. O., Kauvar, I., Ramakrishnan, C., Fenno, L. E., Davidson, T. J., Wright, M., and Deisseroth, K. (2017). Modulation of prefrontal cortex excitation/inhibition balance rescues social behavior in CNTNAP2-deficient mice. Sci Transl Med 9.

Sorokin, J. M., Davidson, T. J., Frechette, E., Abramian, A. M., Deisseroth, K., Huguenard, J. R., and Paz, J. T. (2017). Bidirectional Control of Generalized Epilepsy Networks via Rapid Real-Time Switching of Firing Mode. Neuron 93, 194-210.

Szarowski, D. H., Andersen, M. D., Retterer, S., Spence, A. J., Isaacson, M., Craighead, H. G., Turner, J. N., and Shain, W. (2003). Brain responses to micro-machined silicon devices. Brain Res 983, 23-35.

Tanaka, K. F., Matsui, K., Sasaki, T., Sano, H., Sugio, S., Fan, K., Hen, R., Nakai, J., Yanagawa, Y., Hasuwa, H., et al. (2012). Expanding the Repertoire of Optogenetically Targeted Cells with an Enhanced Gene Expression System. Cell Rep 2, 397-406.

Thyagarajan, S., van Wyk, M., Lehmann, K., Lowel, S., Feng, G., and Wassle, H. (2010). Visual function in mice with photoreceptor degeneration and transgenic expression of channelrhodopsin 2 in ganglion cells. J Neurosci 30, 8745-8758.

Ullrich, S., Gueta, R., and Nagel, G. (2013). Degradation of channelopsin-2 in the absence of retinal and degradation resistance in certain mutants. Biol Chem 394, 271-280.

Weaver, F. M., Follett, K. A., Stern, M., Luo, P., Harris, C. L., Hur, K., Marks, W. J., Rothlind, J., agher, O., Moy, C., et al. (2012). Randomized trial of deep brain stimulation for Parkinson disease Thirty-six-month outcomes. Neurology 79, 55-65.

Williams, J. C., and Denison, T. (2013). From Optogenetic Technologies to Neuromodulation Therapies. Sci Transl Med 5.

Xu, H. T., Pan, F., Yang, G., and Gan, W. B. (2007). Choice of cranial window type for in vivo imaging affects dendritic spine turnover in the cortex. Nature neuroscience 10, 549-551.

Yizhar, O., Fenno, L. E., Davidson, T. J., Mogri, M., and Deisseroth, K. (2011a). Optogenetics in Neural Systems. Neuron 71, 9-34.

Yizhar, O., Fenno, L. E., Prigge, M., Schneider, F., Davidson, T. J., O'Shea, D. J., Sohal, V. S., Goshen, I., Finkelstein, J., Paz, J. T., et al. (2011b). Neocortical excitation/inhibition balance in information processing and social dysfunction. Nature 477, 171-178.

Zhao, S., Ting, J. T., Atallah, H. E., Qiu, L., Tan, J., Gloss, B., Augustine, G. J., Deisseroth, K., Luo, M., Graybiel, A. M., and Feng, G. (2011). Cell type-specific channelrhodopsin-2 transgenic mice for optogenetic dissection of neural circuitry function. Nat Methods 8, 745-752.

Zhao, Y. J., Yu, T. T., Zhang, C., Li, Z., Luo, Q. M., Xu, T. H., and Zhu, D. (2018). Skull optical clearing window for in vivo imaging of the mouse cortex at synaptic resolution. Light-Sci Appl 7.

All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

One skilled in the art would readily appreciate that the present disclosure is well adapted to carry out the objects and obtain the ends and advantages mentioned, as well as those inherent therein. The methods and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Embodiments of this disclosure are described herein, including the best mode known to the inventors for carrying out the embodiments presented in the disclosure. Variations of those embodiments may become apparent to those of ordinary skill in the art upon reading the foregoing description.

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the embodiments presented in the disclosure. Thus, it should be understood that although the present disclosure provides preferred embodiments, optional features, modification and variation of the concepts herein disclosed may be resorted to by those skilled in the art, and that such modifications and variations are considered to be within the scope of this disclosure as defined by the description and the appended claims.

It will be readily apparent to one skilled in the art that varying substitutions and modifications can be made to the embodiments presented in the disclosure herein without departing from the scope and spirit of the presented embodiments in the disclosure. Thus, such additional embodiments are within the scope of the present disclosure and the following claims. The present disclosure teaches one skilled in the art to test various combinations and/or substitutions of chemical modifications described herein toward generating conjugates possessing improved contrast, diagnostic and/or imaging activity. Therefore, the specific embodiments described herein are not limiting and one skilled in the art can readily appreciate that specific combinations of the modifications described herein can be tested without undue experimentation toward identifying conjugates possessing improved contrast, diagnostic and/or imaging activity.

The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context. Those skilled in the art will recognize, or be able to ascertain using no more than routine experimentation, many equivalents to the specific embodiments of the disclosure described herein. Such equivalents are intended to be encompassed by the following claims.

We claim:

1. A composition comprising a step-function opsin (SFO) polypeptide comprising at least two stabilized step function mutations and at least one peak amplitude increasing mutation, wherein the at least two stabilized step function mutations comprise C128S and D156A mutations, wherein the at least one peak amplitude increasing mutation comprises a T159C mutation, wherein the SFO polypeptide is encoded by a nucleotide sequence having at least 95% nucleotide identity to SEQ ID NO:3.

2. The composition of claim 1, wherein the SFO polypeptide has an amino acid sequence having at least 95% amino acid identity to a polypeptide encoded by SEQ ID NO: 1.

3. The composition of claim 1, wherein the SFO polypeptide is encoded by a nucleotide sequence having at least 96% nucleotide identity to SEQ ID NO:3.

4. The composition of claim 1, wherein the SFO polypeptide is adapted to:

induce a peak photocurrent amplitude from about 250 pA to about 450 pA; and/or maintain a prolonged open state from about 25 minutes to about 45 minutes.

5. The composition of claim 1, wherein the SFO polypeptide is adapted to induce a peak photocurrent amplitude of about 320 pA, about 330 pA, about 340 pA, about 350 pA, about 360, about 370 pA, or about 380 pA.

6. The composition of claim 1, wherein the SFO polypeptide is adapted to maintain a prolonged open state of about 25 minutes, about 30 minutes, about 35 minutes, about 40 minutes, or about 45 minutes.

7. The composition of claim 1, wherein the SFO is adapted to reversibly depolarize a neuronal cell.

8. The composition of claim 1, wherein the SFO is adapted to be activated by a first wavelength of light and to be deactivated by a second wavelength of light.

9. A composition comprising a step-function opsin (SFO) polypeptide comprising:

at least two stabilized step function mutations, wherein the at least two step function mutations are adapted to prolong the open state of an opsin ion channel of the SFO after a light pulse; and at least one peak amplitude increasing mutation, wherein the at least one peak amplitude increasing mutation is adapted to increase conductance of an opsin ion channel of the SFO after a light pulse, relative to a control, wherein the at least two stabilized step function mutations comprise C128S and D156A mutations, wherein the at least one peak amplitude increasing mutation comprises a T159C mutation, wherein the SFO polypeptide is encoded by a nucleotide sequence having at least 95% nucleotide identity to SEQ ID NO:3.

10. The composition of claim 9, wherein the SFO polypeptide comprises an amino acid sequence having at least 95% amino acid identity to a polypeptide encoded by SEQ ID NO:1.

11. The composition of claim 9, wherein the SFO polypeptide is adapted to induce a peak photocurrent amplitude of about 320 pA, about 330 pA, about 340 pA, about 350 pA, about 360, about 370 pA, or about 380 pA.

12. The composition of claim 9, wherein the SFO polypeptide is adapted to maintain a prolonged open state of about 25 minutes, about 30 minutes, about 35 minutes, about 40 minutes, or about 45 minutes.

13. The composition of claim 9, wherein the SFO polypeptide has an amino acid sequence having at least 965% amino acid identity to a polypeptide encoded by SEQ ID NO: 3.

14. A composition comprising a step-function opsin (SFO) polypeptide comprising C128S, D156A, and T159C mutations, wherein the SFO polypeptide is encoded by a nucleotide sequence having at least 95% nucleotide identity to SEQ ID NO:3.

15. A method for modulating activity of a neuronal cell expressing the composition of claim 1, wherein the method comprises exposing the neuronal cell expressing the composition of claim 1 to one or more wavelengths of light, thereby modulating an activity of the neuronal cell in response to the one or more wavelengths of light.

* * * * *